United States Patent
Ayakar et al.

(10) Patent No.: US 12,077,802 B2
(45) Date of Patent: Sep. 3, 2024

(54) **METABOLIC ENGINEERING OF *E. COLI* FOR THE BIOSYNTHESIS OF CANNABINOID**

(71) Applicant: INMED PHARMACEUTICALS INC., Vancouver (CA)

(72) Inventors: Sonal R. Ayakar, Vancouver (CA); Sandip V. Pawar, Vancouver (CA); Steven J. Hallam, Vancouver (CA); Sazzad Hossain, Richmond (CA); Vikramaditya G. Yadav, Vancouver (CA); Protiva R. Roy, Vancouver (CA); Sarvesh K. Srivastava, Vancouver (CA)

(73) Assignee: INMED PHARMACEUTICALS INC., Vancouver (CA)

( * ) Notice: Subject to any disclaimer, the term of this patent is extended or adjusted under 35 U.S.C. 154(b) by 626 days.

(21) Appl. No.: 16/644,484

(22) PCT Filed: Sep. 5, 2018

(86) PCT No.: PCT/CA2018/051074
§ 371 (c)(1),
(2) Date: Mar. 4, 2020

(87) PCT Pub. No.: WO2019/046941
PCT Pub. Date: Mar. 14, 2019

(65) Prior Publication Data
US 2020/0291434 A1    Sep. 17, 2020

Related U.S. Application Data

(60) Provisional application No. 62/554,494, filed on Sep. 5, 2017.

(51) Int. Cl.
| | |
|---|---|
| *C12P 7/42* | (2006.01) |
| *C12N 9/02* | (2006.01) |
| *C12N 9/10* | (2006.01) |
| *C12N 9/12* | (2006.01) |
| *C12N 9/88* | (2006.01) |
| *C12N 15/70* | (2006.01) |
| *C12P 5/00* | (2006.01) |

(52) U.S. Cl.
CPC ............. *C12P 7/42* (2013.01); *C12N 9/0004* (2013.01); *C12N 9/1007* (2013.01); *C12N 9/1241* (2013.01); *C12N 9/88* (2013.01); *C12N 15/70* (2013.01); *C12P 5/007* (2013.01); *C12Y 121/03007* (2015.07); *C12Y 201/01255* (2015.07); *C12Y 207/0706* (2013.01); *C12Y 402/03027* (2013.01); *C12N 2800/101* (2013.01)

(58) Field of Classification Search
CPC .......... C12P 7/42; C12P 5/007; C12N 9/0004; C12N 9/1007; C12N 9/1241; C12N 9/88; C12N 15/70; C12N 2800/101; C12Y 121/03007; C12Y 201/01255; C12Y 207/0706; C12Y 402/03027
See application file for complete search history.

(56) References Cited

U.S. PATENT DOCUMENTS

| | | | |
|---|---|---|---|
| 9,359,625 B2 | 6/2016 | Winnicki et al. | |
| 9,394,512 B2 | 7/2016 | Bayer et al. | |
| 9,512,391 B2 | 12/2016 | Peet et al. | |
| 9,526,715 B1 | 12/2016 | Winnicki et al. | |
| 9,587,212 B2 | 3/2017 | Winnicki et al. | |
| 2005/0221467 A1 | 10/2005 | Brzostowicz et al. | |
| 2016/0010126 A1 | 1/2016 | Poulos et al. | |

FOREIGN PATENT DOCUMENTS

| | | |
|---|---|---|
| CN | 106148263 A | 11/2016 |
| WO | WO 2004/056975 A2 | 7/2004 |
| WO | WO 2011/127589 A1 | 10/2011 |

OTHER PUBLICATIONS

Gabrielson M et al. Biosynthesis of isoprenoids a bifunctional IspDF enzyme. 2004. European Journal of Biochemistry. 271, 3028-3035. (Year: 2004).*
Singh RK et al. Protein Engineering Approaches in the Post-Genomic Era. 2017. Current Protein and Peptide Science. 18, 1-11. (Year: 2017).*
Zhang M et al. Propagated Perturbations from a Peripheral Mutation Show Interactions Supporting WW Domain Thermostability. 2018. Structure. 26, 1474-1485. (Year: 2018).*
Andre, CM et al., "*Cannabis sativa*: The Plant of the Thousand and One Molecules", Frontiers in Plant Science, vol. 7, No. 19, pp. 1-17 (2016).
Gabrielsen, M et al., "Biosynthesis of isoprenoids. A bifunctional IspDF enzyme from Campylobacter jejuni", Eur. J. Biochem, vol. 271, pp. 3028-3035 (2004).
Lherbet et al., "Absence of Substrate Channeling between Active Sites in the Agrobacterium tumefaciens IspDF and IspE Engzyme of the Methyl Erythritol Phosphate Pathway", Biochemistry, vol. 45, pp. 3548-3553 (2006).
Perez-Gil, J et al., "Cloning andfunctional characterization of an enzyme from Helicobacter pylori that catalyzes two steps of the methylerythritol phosphate pathway for isoprenoid biosynthesis", Biochimica et Biophysica Acta, vol. 1800, pp. 919-928 (2010).
Testa et al, "Cloning and expression of IspDF from Mesorhizobium loti. Characterization of a bifunctional protein that catalyzes non-consecutive steps in the methylerythritol phosphate pathway", Biochimica Et Biophysica Acta (BBA)—Proteins & Proteomics, Elsevier, Netherlands, vol. 1764, No. 1, pp. 1570-9639, (2006).
Yang, J et al., "Biosynthesis of [i-carotene in engineered *E. coli* using the MEP and MVA pathways", Microbial Cell Factories, vol. 13, pp. 1-11 (2014).

(Continued)

*Primary Examiner* — Paul J Holland
(74) *Attorney, Agent, or Firm* — Todd Lorenz

(57) ABSTRACT

Provided herein are methods and compositions for producing terpenoids in a host cell. In some cases, the terpenoids are cannabinoids.

49 Claims, 26 Drawing Sheets

Specification includes a Sequence Listing.

(56) References Cited

OTHER PUBLICATIONS

Yuan, LZ et al., "Chromosomal promoter replacement of the isoprenoid pathway for enhancing carotenoid production in E. coli", Metabolic Engineering, vol. 8, pp. 79-90 (2006).
GenBank Accession No. MEKT01000147, submitted 2016.
GenBank Accession No. MEKW01000028, submitted 2016.
GenBank Accession No. MELC01000063, submitted 2016.
Zhang et al., "Strategies for Improving the Yield of Microbial Synthesis of Terpenoids", Chinese Journal of Bioengineering, 37.1, pp. 97-103, 2017.
Qi et al. "Integration of heterologous 4-hydroxybenzoic acid transport proteins in Rhodobacter sphaeroides for enhancement of coenzyme Q10 production", RSC Adv, 7, Mar. 20, 2017, pp. 17346-17352 (2017).
Zhang et al., "Strategies to improve the production of terpenoids synthesized by microorganisms", and "Strategies for Improving the Yield of Microbial Terpenoids Production", Chinese Journal of Bioengineering, 37(1), pp. 97-103 (2017).

* cited by examiner pACYC duet 1
(~10-20 copies)

pTrc-trGPPS(CO)-LS
(~20-25 copies)

| Strain name | Inducers concentration |
|---|---|
| a | pBAD33_GPPS_CBGAS | Uninduced |
| b | pBAD33_GPPS_CBGAS | 10 mM Arabinose |
| c | pBAD33_GPPS_CBGAS | 15 mM Arabinose |
| d | pBAD33_GPPS_CBGAS | 20 mM Arabinose |
| e | pBAD33_GPPS_CBGAS + pTRC_RDE | Uninduced |
| f | pBAD33_GPPS_CBGAS + pTRC_RDE | 10 mM Arabinose + 0.5 mM IPTG |
| g | pBAD33_GPPS_CBGAS + pTRC_RDE | 15 mM Arabinose+ 0.1 mM IPTG |
| h | pBAD33_GPPS_CBGAS + pTRC_RDE | 15 mM Arabinose+ 0.1 mM IPTG |
| i | pBAD33_GPPS_CBGAS + pTRC_RDE | 10 mM Arabinose+ 0.025 mM IPTG |
| j | pBAD33_GPPS_CBGAS + pTRC_RDE | 0.025 mM IPTG and after 4 hours 10 mM Arabinose |

Fig. 14

```
meta-ispDF    MIALQRSLSMHVTAIIAAAGEGRRLGAPLPKQLLDIGGRSTLERSVMAFARHERIDDVIVVLPPALAAA
CJ-ispDF      MSE------MSLTMLAAGNSTRFNTKVKKQFLRLGNDPLWLYATKNLSSFYPRKIVTSSNI-T-Y
ispD-ispF     MATT----HLDVCAVVPAAGFGRRMQTECPKQYLSIGNQTLLEHSVHALLAHPRVRGRVVIAISPGDSRF
cons          *         :   :***   *      *    *  :*..:.:          ::.        :

meta-ispDF    PPDWIAASGRVPAVHVVSGGERRQDSVANAFDRVPAQSDVVLVHDAARPFVTAELISRAIDGAM-OHGA
CJ-ispDF      MKKF------TKNYEFIEGGDTRAESLKKALEL--IDSEFVMVSDVARVLVSKNLFDRLIENLD-KADC
ispD-ispF     AQLPL---ANHPQITVWDGGDERADSVLAGLKAA-GDAQWVLVHDAARPCLHQDDLARLLALSETSRTG
cons                     :..   *:  :  ***.* .*  :   ::  . *  :  :: :*  :

meta-ispDF    ALVAVPVRDTVKRVDPDGEHPVTTGTIPPDTIYLAQTPQAFRRDVLGA----AVALGRSGVSATDEAML
CJ-ispDF      ITPALKVADTTLFD-------NEALQREKIKLIQTPQISKTKLLKK----AL---DQNLEFTDDSTA
ispD-ispF     GILAAPVRDTMKRAEPGK--NATAHTVDRNGLMHALTPQFFPRELLHDCLTRAL---NEGATTTDEASA
cons                          :        :    : *:*  ::*             :   *:* meta-ispDF    AEQAGHRVHVVEGDRANVKITTSADLDDARQRLRS----AVAARIGTGVDLHRLIEGRPLIIGGV.AVPC
CJ-ispDF      IAAMGGKTNFVEGEENARKLTFKEDLKKLDLP-TP---SFELFTGNGFDVHEFGENRPLLLAGVQIHP
ispD-ispF     LEYCGFHPQLVEGRADMIKVTRPEDLALAEFYLTRITHQENTMRIGHGFDVHAFGGEGPIIIGGVRIPY
cons               :.****   *:    **   : :                 .:*:*  :*   *::.*.

meta-ispDF    DKGALGHSDADVACHAVIDALLGAAGAGNVGQHYPDTDPRMKGASSIGILLRDALRLVQERGFTVENVDV
CJ-ispDF      TMGLKAHSDGDVLAHSLTDAILGAAGLGDIGELYPDTDMKFKNANSMELLKQAYDKVREIGFELINIDI
ispD-ispF     EKGLLAHSDGDVALHALTDALLGAAALGDIGKLFPDTDPAFKGADSRELLREAWRRIQAKGYTLGNVDV
cons              .***.**.   : ::*.:******  *   :: ****.* *.:. ::**   :*   :   :

meta-ispDF    CVVLERPKIAPFIPEIRARIAGALGIDPERVSVKGKTNEGVDAVGRGEAIAAHAVALLSE----S
CJ-ispDF      CVMAQSPKLVDFKQAMQSNIAHTLDLDEFRINVKAITTEKLGFIGRKEGHA.VLSSVNLKYFDWTRL
ispD-ispF     TIIAQAPKMLPHTPQMRVFTAEDLGCHMDQVNVKATTTEKLGFTGRGEGTACEAVALLIK-ATK-
cons          :: :  *: .:             :     *  ::***  *.* **    ::::*

Fig. 19
```

IspDF1
MIALQRSLSMHVTAIIAAAGEGRRLGAPLPKQLLDIGGRSILERSVMAFARHERIDDVIVVLPPALAAAPPDWIAASGRVPAVHVVSGGERRQDSV
ANAFDRVPAQSDVVLVHDAARPFVTAELISRAIDGAMQHGAAIVAVPVRDTVKRVDPDGEHPVITGTIPRDTIYLAQTPQAFRRDVLGAAVALGR
SGVSATDEAMLAEQAGHRVHVVEGDPANVKITTSADLDQARQRLRSAVAARIGTGYDLHRLIEGRPLIIGGVAVPCDKGALGHSDADVACHAVID
ALLGAAGAGNVGQHYPDTDPRWKGASSIGLLRDALRLVQERGFTVENVDVCVVLERPKIAPFIPEIRARIAGALGIDPERVSVKGKTNEGVDAVG
RGEAIAAHAVALLSES

IspDF2
MQVTAIIAAGGRGRRFGGGVPKQLVGVGGRPILERTVAAFLGHPAIHEVVVALPAELMADPPAYLRAAPKPIRLVAGGVQRQDSVRQAFQAANE
QSDVIVIHDAARPFASADLISRTIAAAAEGGAALAAVPARDTVKRGAFAAGRTGPAGRQAVEGAPLLVVAETLPRDSIYLAQTPQAFRRDVLRDAL
ALGEAGSEATDEATLAERAGHIVRLVEGEPANIKITTPDDLLVAEAIARGTGERAVGERAAFRIGAGYDLHRLVEGRPLVLGGVTIPFERGLLGHSDA
DAICHAVTDAVLGAAAAGDIGRHFPDSDPKWRDWSSIDLLRRASAIVKGRGYAIANVDAVVIAERPKLAPFLDEMRANVAGAIGIAVDAVGIKGK
TNEGLGELGRGEAIAVHAVALLHL

IspDF3
MVHVSAIIAAGGRGERFGGPQPKQLLLLGGVPILKRTVDAFLRGYPFIEVIVALPAEFVANPPDYLDDVIVVEGGARRQDSVANAFRAVAPSAQVV
VIHDAARPLVTPSLIERTVDAAVKHGAAIAALRATDTVKRGDASRVIRGTLPRDEIFLAQTPQAFRAGVLRDALALAASAADATDEAMLAEQAGH
HVRLVDGDPRNLKITTPEDLEMAERLIGARNTAGAMRIGNGYDLHRLVTGRPLVLGGVTIPFEKGLQGHSDADAVCHAITDAILGAASAGDIGRH
FPDTDPAWKDAKSIVLLQQAAQIVSRAGYAIANLDVVVIAQQPKLVPHIDAIRHSVAHALGIDVQQVSVKGKTNEGVDSMGAGESIAVHAVALLQ
HS

Fig. 26

METABOLIC ENGINEERING OF E. COLI FOR THE BIOSYNTHESIS OF CANNABINOID

CROSS-REFERENCE TO RELATED APPLICATIONS

This application claims priority to U.S. Provisional Patent Application No. 62/554,494, the contents of which are hereby incorporated by reference in the entirety and for all purposes.

SEQUENCE LISTING

The instant application contains a Sequence Listing which has been submitted electronically in ASCII format and is hereby incorporated by reference in its entirety. Said ASCII copy, created on Oct. 17, 2018, is named NMD-003_PCT_SL.txt and is 109,691 bytes in size.

BACKGROUND OF THE INVENTION

The glandular trichomes of the plant *Cannabis sativa* accumulate a variety of terpenophenolic chemical compounds (Cannabinoids). These plant derived natural products are capable of interacting directly to the cannabinoid receptors (CB1 and CB2) found throughout the animal and human body. CB-1 receptors are primarily found in the nervous system and CB-2 receptors are predominantly found in the immune system, or immune-derived cells.

Cannabinoids, and derivatives thereof, have several properties with therapeutic potential. Activation or blocking of CB-1 and/or CB-2 receptors with a cannabinoid can regulate downstream signalling and metabolic pathways and subsequently influence synaptic transmission, including transmission of pain and other sensory signals in the periphery, immune response, and inflammation. Thus, there is an interest in use of natural or synthetic cannabinoids for therapeutic purposes. However, low extraction yields, and high separation costs have rendered the use of naturally-derived cannabinoids uneconomical. Similarly, fully synthetic methods of cannabinoid production are hampered by the complexity of these compounds.

Heterologous systems for production of cannabinoids known in the art rely on eukaryotic host organisms for production and secretion of cannabinoid synthase enzymes, which are then used to produce a cannabinoid product in an in vitro enzyme-catalyzed reaction. For example, U.S. Pat. Nos. 9,587,212; 9,512,391; 9,394,512; 9,526,715; 9,359,625 each describe methods and compositions and bioreactors for making cannabinoids using a recombinant Pichia pastoris that secretes THCA synthase or CBDA synthase. Unfortunately, however, this system requires additional means to generate a suitable substrate for the secreted enzyme. Thus, there is a long felt and unmet need to develop a cost-effective heterologous system for the production of cannabinoids in vivo.

SUMMARY OF THE INVENTION

Described herein are methods, compositions, and host cells for production of cannabinoids, and terpenoids.

In one aspect, the present invention provides an expression cassette comprising a heterologous promoter operably linked to a nucleic acid encoding a bifunctional ispDF enzyme. In some embodiments, the expression cassette increases the flux through the MEP pathway in a host cell in which the expression cassette is present. The increased flux through the MEP pathway can increase the production of isoprenoid precursors suitable for increasing downstream production of geranyl phosphate (GPP), farnesyl pyrophosphate (FPP), geranylgeranyl pyrophosphate (GGPP), terpenoids, isoprene, lycopene, cannabinoid (e.g., CBGA), monoterpenes, sesquiterpenes, diterpenes, and/or carotenoids. Accordingly, in some embodiments, the expression cassette optionally comprises components of a lycopene synthesis pathway (e.g., crtE, crtI, and/or crtB), an isoprene synthase, a GPP synthase (e.g., ispA or a plant derived GPP synthase), a monoterpene synthase, and/or a cannabinoid synthase.

In some embodiment, the bifunctional ispDF enzyme differs by at least one amino acid from the following ispDF enzymes: *H. pylori* HP1020, *H. pylori* J99 jhp0404, *H. pylori* HPAG1 HPAG1_0427, *H. hepaticas* HH1582, *H. acinonychis* st. Sheeba Hac_1124, *W. succinogenes* DSM 1740 WS1940, *S. denitrificans* DSM 1251 Suden_1487, *C. jejuni* subsp. *jejuni* NCTC 11168 Cj1607, *C. jejuni* RM1221 CJE1779, *C. jejuni* subsp. *jejuni* 81-176 CJJ81176_1594, and *C. fetus* subsp. *fetus* 82-40 CFF8240_0409. In some cases, the bifunctional ispDF enzyme is no more than 25%, 30%, 35%, 40%, 45%, 50%, 55%, 60%, 70%, 75%, 80%, 90%, or 95% identical to any one of the following ispDF enzymes: *H. pylori* HP1020, *H. pylori* J99 jhp0404, *H. pylori* HPAG1 HPAG1_0427, *H. hepaticas* HH1582, *H. acinonychis* st. Sheeba Hac_1124, *W. succinogenes* DSM 1740 WS1940, *S. denitrificans* DSM 1251 Suden_1487, *C. jejuni* subsp. *jejuni* NCTC 11168 Cj1607, *C. jejuni* RM1221 CJE1779, *C. jejuni* subsp. *jejuni* 81-176 CJJ81176_1594, and *C. fetus* subsp. *fetus* 82-40 CFF8240_0409. In some embodiments, the bifunctional ispDF enyme is no more than 35%, 34%, 33%, 32%, 31%, 30%, 29%, 28%, 27%, 26%, or 25% similar to CJ-ispDF using default BLAST 2.7.0 protein:protein alignment settings.

In some embodiments, the promoter operably linked to the nucleic acid encoding the bifunctional ispDF enzyme is an inducible promoter. In some embodiments, the promoter operably linked to the nucleic acid encoding the bifunctional ispDF enzyme is a constitutive promoter. In some embodiments, the bifunctional ispDF enzyme comprises an amino acid sequence at least 50%, 55%, 60%, 65%, 70%, 75%, 80%, 85%, 90%, 95%, or 99% identical, or identical, to 25, 50, 75, 100, 125, 150, 175, 200, 225, 250, 275, or 300 contiguous amino acids of SEQ ID No. 1, SEQ ID No. 2, or SEQ ID No. 3. In some embodiments, the bifunctional ispDF enzyme comprises an amino acid sequence at least 50%, 55%, 60%, 65%, 70%, 75%, 80%, 85%, 90%, 95%, or 99% identical, or identical, to SEQ ID No. 1, SEQ ID No. 2, or SEQ ID No. 3.

In some embodiments, the nucleic acid encoding the bifunctional ispDF enzyme is codon optimized. In some embodiments, the expression cassette further comprises a nucleic acid encoding one or more, two or more, or all of the enzymes selected from the group consisting of dxs, idi, and ispE. In some embodiments, the expression cassette further comprises a nucleic acid encoding dxs and idi, and optionally a GPP synthase (e.g., ispA or a plant derived GPP synthase), a monoterpene synthase, and/or a cannabinoid synthase. In some embodiments, the expression cassette further comprises a nucleic acid encoding dxs, idi, and ispE, and optionally a GPP synthase (e.g., ispA or a plant derived GPP synthase), a monoterpene synthase, and/or a cannabinoid synthase. In some embodiments, the cannabinoid synthase is CBGA synthase, preferably *Cannabis* CBGA synthase.

In some embodiments, the cannabinoid synthase is a truncated cannabinoid synthase selected from the group consisting of a THCA synthase, CBDA synthase, and CBCA synthase, wherein the truncation is a deletion of all or part of a signal peptide.

In one aspect, the present invention provides a plasmid comprising at least one, two, three, or more expression cassettes according to any of the expression cassette aspects, embodiments, cases, or examples described herein, or fragment(s) thereof. In another aspect, the present invention provides a plurality of plasmids comprising at least two, three, four, or more expression cassettes according to any one of the expression cassette aspects, embodiments, cases, or examples described herein, or fragment(s) thereof.

In some embodiments, the plasmid or plasmids comprise an expression cassette comprising a nucleic acid encoding an isoprene synthase (ispS). In some embodiments, the plasmid or plasmids comprise an expression cassette comprising a nucleic acid encoding a GPP synthase. In some embodiments, the GPP synthase is a GPP synthase derived from a eukaryote. In some embodiments, the GPP synthase is a plant-derived GPP synthase. In some embodiments, the GPP synthase is codon optimized, e.g., for expression in the host cell.

In some embodiments, the plasmid or plasmids comprise a nucleic acid encoding one or more components of a lycopene synthesis pathway (e.g., crtE, crtI, and/or crtB), a diterpene synthase, a sesquiterpene synthase, or a monoterpene synthase. In some embodiments, the plasmid or plasmids comprise a nucleic acid encoding carene synthase, myrcene synthase, or limonene synthase. In some embodiments, the plasmid or plasmids comprise a nucleic acid encoding a cannabinoid synthase.

In some cases, the cannabinoid synthase is selected from the group consisting of a CBGA synthase, THCA synthase, CBDA synthase, and CBCA synthase. In some embodiments, the cannabinoid synthase is selected from the group consisting of a *Cannabis* CBGA synthase, THCA synthase, CBDA synthase, and CBCA synthase. In some embodiments, the cannabinoid synthase is, e.g., *Cannabis*, CBGA synthase. In some embodiments, In some embodiments, the cannabinoid synthase is a truncated cannabinoid synthase selected from the group consisting of a THCA synthase, CBDA synthase, and CBCA synthase, wherein the truncation is a deletion of all or part of a signal peptide.

In one aspect, the present invention provides a host cell comprising any one or more of the expression cassette(s) described herein, and/or any one or more of the plasmid(s) described herein. In some embodiments, one or more, or all, of the one or more expression cassette(s) of the host cell are integrated into the genome of the host cell in one locus, or a plurality of loci.

In one aspect, the present invention provides a host cell comprising: a). an expression cassette comprising a promoter operably linked to a nucleic acid encoding a bifunctional ispDF enzyme; and b.) an expression cassette comprising a promoter operably linked to a nucleic acid encoding a terpenoid synthase. In some embodiments: i.) the cannabinoid synthase, the ispDF, or one or both of the promoters is heterologous to the host cell; ii.) the nucleic acid encoding the bifunctional ispDF enzyme is heterologous to the operably linked promoter; and/or iii.) the nucleic acid encoding the cannabinoid synthase is heterologous to the operably linked promoter.

In some embodiments, the terpenoid synthase is an isoprene synthase. In some embodiments, the terpenoid synthase is a component of a lycopene synthase pathway (e.g., crtI, crtE, or crtB). In some embodiments, the host cell comprising a nucleic acid encoding a component of a lycopene synthesis pathway comprises one or more nucleic acid(s) encoding crtI, crtE, and crtB, wherein crtI, crtE, and crtB are in the same or different expression cassettes.

In some embodiments, the terpenoid synthase is a cannabinoid synthase. In some embodiments, the cannabinoid synthase is selected from the group consisting of CBGA synthase, THCA synthase, CBDA synthase, and CBCA synthase. In some embodiments, the cannabinoid synthase is selected from the group consisting of a *Cannabis* CBGA synthase, THCA synthase, CBDA synthase, and CBCA synthase. In some embodiments, the cannabinoid synthase is a *Cannabis sativa* cannabinoid synthase. In some embodiments, the host cell comprises a nucleic acid encoding CBGA synthase and a nucleic acid encoding another cannabinoid synthase selected from the group consisting of THCA synthase, CBDA synthase, and CBCA synthase, or a combination of one or more nucleic acids encoding two or all thereof.

In some embodiments, where the host cell comprises the expression cassette comprising a promoter operably linked to a nucleic acid encoding a cannabinoid synthase, the cannabinoid synthase is CBGA synthase. In some cases, the host cell comprising the CBGA synthase expression cassette further comprises a nucleic acid encoding a THCA synthase, CBDA synthase, and/or CBCA synthase each cannabinoid synthase independently operably linked to a promoter in the same or a different expression cassette.

In some embodiments, the cannabinoid synthase, or at least one encoded cannabinoid synthase, is a truncated cannabinoid synthase selected from the group consisting of a THCA synthase, CBDA synthase, and CBCA synthase, wherein the truncation is a deletion of all or part of a signal peptide. In some embodiments, the cannabinoid synthase comprises a deletion of all or part of a transmembrane or membrane-associated region, such that the cannabinoid synthase is not membrane-associated.

In some embodiments, the host cell comprises an expression cassette comprising a heterologous promoter operably linked to a nucleic acid encoding a GPP synthase. In some embodiments, the expression cassette of a) or b) further comprises a nucleic acid encoding a GPP synthase. In some embodiments, the host cell does not comprise a heterologous nucleic acid encoding ispC, ispE, ispG, ispH, or a combination thereof, or all thereof. In some embodiments, the host cell does not comprise a heterologous nucleic acid encoding ispC, ispG, ispH, a combination thereof, or all thereof.

In some embodiments, the host cell is a prokaryote, such as a prokaryote of the genus *Escherichia*, *Panteoa*, *Bacillus*, *Corynebacterium*, or *Lactococcus*. In some embodiments, the cell is *Escherichia coli* (*E. coli*), *Panteoa citrea*, *C. glutamicum*, *Bacillus subtilis*, or *L. lactis*.

In some embodiments, the expression cassette of a) and/or b) is integrated into the genome of the host cell. In some embodiments, the expression cassette of a) is integrated into the genome of the host cell and the expression cassette of b) is not integrated, or is integrated at a different locus in the genome of the host cell. In some embodiments, the expression cassette of b) is integrated into the genome of the host cell and the expression cassette of a) is not integrated, or is integrated at a different locus in the genome of the host cell. In some embodiments, the expression cassette of a) and the expression cassette of b) are integrated into the genome of the host cell at the same, or a different, locus.

In some embodiments, the expression cassette of a) and/or b) resides on a plasmid in the host cell. In some embodiments, the expression cassette of a) and the expression cassette of b) resides on a plasmid in the host cell. In some embodiments, the host cell comprises a plasmid comprising the expression cassette of a) and/or b). In some embodiments, the host cell comprises a plasmid comprising the expression cassette of a), and/or a plasmid comprising the expression cassette of b). In some embodiments, the expression cassette of a) and the expression cassette of b) are in the same plasmid. In some embodiments, the expression cassette of a) is in a different plasmid than the expression cassette of b).

In some embodiments, the expression cassette comprising the promoter operably linked to a nucleic acid encoding a bifunctional ispDF enzyme also comprises the same promoter operably linked to a nucleic acid encoding a cannabinoid synthase. In some cases, the cannabinoid synthase is CBGA synthase. In some embodiments, the host cell comprises a nucleic acid encoding a cannabinoid synthase (e.g., CBGA synthase) operably linked to a constitutive promoter. In some embodiments, the host cell comprises a nucleic acid encoding a cannabinoid synthase (e.g., CBGA synthase) operably linked to an inducible promoter.

In some embodiments, the promoter operably linked to the nucleic acid encoding the bifunctional ispDF enzyme is a constitutive promoter. In some embodiments, the promoter operably linked to the nucleic acid encoding the bifunctional ispDF enzyme is an inducible promoter. In some embodiments, where the host cell comprises two or more expression cassettes comprising different cannabinoid synthases, each expression cassette comprising a constitutive promoter operably linked to a cannabinoid synthase, each expression cassette comprising an inducible promoter operably linked to a cannabinoid synthase, or one or more expression cassette(s) comprising a constitutive promoter operably linked to a cannabinoid synthase and one expression cassette(s) comprising an inducible promoter operably linked to a cannabinoid synthase.

In some embodiments, where the host cell comprises two or more expression cassettes comprising different cannabinoid synthases, each expression cassette comprises an inducible promoter operably linked to a cannabinoid synthase. In some embodiments, where the host cell comprises two or more expression cassettes comprising different cannabinoid synthases, at least one expression cassette comprises an inducible promoter operably linked to a cannabinoid synthase. In some embodiments, where the host cell comprises two or more expression cassettes comprising different cannabinoid synthases, at least one expression cassette comprises a constitutive promoter operably linked to a cannabinoid synthase.

In some embodiments, the bifunctional ispDF enzyme comprises an amino acid sequence at least 50%, 55%, 60%, 65%, 70%, 75%, 80%, 85%, 90%, 95%, or 99% identical, or identical, to 25, 50, 75, 100, 125, 150, 175, 200, 225, 250, 275, or 300 contiguous amino acids of SEQ ID No. 1, SEQ ID No. 2, or SEQ ID No. 3. In some embodiments, the bifunctional ispDF enzyme comprises an amino acid sequence at least 50%, 55%, 60%, 65%, 70%, 75%, 80%, 85%, 90%, 95%, or 99% identical, or identical, to SEQ ID No. 1, SEQ ID No. 2, or SEQ ID No. 3.

In some embodiment, the bifunctional ispDF enzyme differs by at least one amino acid from the following ispDF enzymes: *H. pylori* HP1020, *H. pylori* J99 jhp0404, *H. pylori* HPAG1 HPAG1_0427, *H. hepaticus* HH1582, *H. acinonychis* st. Sheeba Hac_1124, *W. succinogenes* DSM 1740 WS1940, *S. denitrificans* DSM 1251 Suden_1487, *C. jejuni* subsp. *jejuni* NCTC 11168 Cj1607, *C. jejuni* RM1221 CJE1779, *C. jejuni* subsp. *jejuni* 81-176 CJJ81176_1594, and *C. fetus* subsp. *fetus* 82-40 CFF8240_0409. In some cases, the bifunctional ispDF enzyme is no more than 50%, 80%, 90%, or 95% identical to any one of the following ispDF enzymes: *H. pylori* HP1020, *H. pylori* J99 jhp0404, *H. pylori* HPAG1 HPAG1_0427, *H. hepaticus* HH1582, *H. acinonychis* st. Sheeba Hac_1124, *W. succinogenes* DSM 1740 WS1940, *S. denitrificans* DSM 1251 Suden_1487, *C. jejuni* subsp. *jejuni* NCTC 11168 Cj1607, *C. jejuni* RM1221 CJE1779, *C. jejuni* subsp. *jejuni* 81-176 CJJ81176_1594, and *C. fetus* subsp. *fetus* 82-40 CFF8240_0409.

In some embodiments, the host cell comprises or further comprises an expression cassette comprising a promoter operably linked to a nucleic acid encoding one or more MEP pathway enzymes selected from the group consisting of dxs, ispC, ispD, ispE, ispF, ispG, ispH, and idi. In some cases, the expression cassette comprising the bifunctional ispDF enzyme further comprises a nucleic acid encoding one or more MEP pathway enzymes selected from the group consisting of dxs, ispC, ispD, ispE, ispF, ispG, ispH, and idi. In some cases, the expression cassette comprising the bifunctional ispDF enzyme further comprises a nucleic acid encoding dxs and idi. In some cases, the expression cassette comprising the bifunctional ispDF enzyme further comprises a nucleic acid encoding ispE. In some cases, the expression cassette comprising the bifunctional ispDF enzyme further comprises dxs, idi, and ispE. In some cases, the expression cassette comprising the bifunctional ispDF enzyme does not comprise a nucleic sequence acid encoding one or more, or all, of ispC, ispE, ispF, ispG, or ispH. In some cases, the expression cassette comprising the bifunctional ispDF enzyme does not comprise a nucleic sequence acid encoding one or more, or all, of ispC, ispF, ispG, or ispH.

In some cases, the host cell comprises a higher level of expression of one or more MEP pathway genes as compared to a control cell that does not comprise the expression cassette comprising the bifunctional ispDF enzyme. In some cases, the host cell comprises a higher level of expression of dxs and idi as compared to a control cell that does not comprise the expression cassette comprising the bifunctional ispDF enzyme. In some cases, the host cell exhibits higher flux through the MEP pathway as compared to a control cell that does not comprise at least one of the one or more expression cassette(s) and/or one or more plasmid(s) described herein.

In some embodiments, the host cell comprises an expression cassette comprising a promoter operably linked to a nucleic acid encoding GPP synthase. In some cases, the expression cassette of a) further comprises the nucleic acid encoding GPP synthase. In some cases, the expression cassette of b) further comprises the nucleic acid encoding GPP synthase. In some cases, the expression cassette of a) and the expression cassette of b) are different expression cassettes. In some cases, the expression cassette of a) and the expression cassette of b) are the same expression cassette.

In some embodiments, the host cell further comprises olivetolic acid (OA). In some cases, the olivetolic acid is exogenous to the host cell. For example, the OA can be exogenously applied to a culture media in which the host cell is cultured.

In some embodiments, the host cell comprises an expression cassette comprising a promoter operably linked to a nucleic acid encoding one or more glycosylation pathway genes, wherein: a) the glycosylation pathway genes are heterologous to the host cell; b) the promoter is heterologous to the host cell; c) the promoter is heterologous to one or more of the one or more glycosylation pathway genes; or d) the expression cassette is heterologous to the host cell. In some embodiments, the host cell comprises a deletion in 1, 2, 3, 4, 5, 6, 7, 8, or all of the genes selected from the group consisting of ackA-pta, poxB, ldhA, dld, adhE, pps, and atoDA.

In a second aspect, the present invention provides a host cell comprising an expression cassette comprising a heterologous promoter operably linked to a nucleic acid encoding a bifunctional ispDF enzyme, wherein the bifunctional ispDF enzyme comprises an amino acid sequence at least 50%, 55%, 60%, 65%, 70%, 75%, 80%, 85%, 90%, 95%, or 99% identical, or identical, to 25, 50, 75, 100, 125, 150, 175, 200, 225, 250, 275, or 300 contiguous amino acids of SEQ ID No. 1, SEQ ID No. 2, or SEQ ID No. 3. In some embodiments, the bifunctional ispDF enzyme comprises an amino acid sequence at least 50%, 55%, 60%, 65%, 70%, 75%, 80%, 85%, 90%, 95%, or 99% identical, or identical, to SEQ ID No. 1, SEQ ID No. 2, or SEQ ID No. 3.

In some embodiments, the host cell further comprises an expression cassette comprising a promoter operably linked to a nucleic acid encoding one or more MEP pathway enzymes selected from the group consisting of dxs, ispC, ispD, ispE, ispF, ispG, ispH, and idi, wherein: a) the promoter is heterologous to the one or more MEP pathway enzymes; or b) the promoter or the one or more MEP pathway enzymes is heterologous to the host cell. In some embodiments, the host cell further comprises an expression cassette comprising a promoter operably linked to a nucleic acid encoding dxs and idi. In some embodiments, the host cell further comprises an expression cassette comprising a promoter operably linked to a nucleic acid encoding dxs, idi, and ispE.

In some embodiments, the host cell further comprises an expression cassette comprising a promoter operably linked to a nucleic acid encoding an ispS enzyme. In some embodiments, the host cell further comprises an expression cassette comprising a promoter operably linked to a nucleic acid encoding a GPP synthase enzyme. In some embodiments, the host cell comprises a deletion in 1, 2, 3, 4, 5, 6, 7, 8, or all of the genes selected from the group consisting of ackA-pta, poxB, ldhA, dld, adhE, pps, and atoDA. In some embodiments, the host cell further comprises a cannabinoid synthase.

In some embodiments, the host cell is a prokaryote, such as a prokaryote of the genus *Escherichia, Panteoa, Bacillus, Corynebacterium,* or *Lactococcus*. In some embodiments, the cell is *Escherichia coli (E. coli), Panteoa citrea, C. glutamicum, Bacillus subtilis,* or *L. lactis*.

In another aspect, the present invention provides a method of obtaining a target metabolic product (e.g., a terpenoid or a cannabinoid), the method comprising culturing a host cell according to any one of the aspects, embodiments, cases, or examples described herein in a suitable culture medium under conditions suitable to induce expression in one or more host cell expression cassettes, and then harvesting the cultured cells or spent medium, thereby obtaining the target metabolic product. In some embodiments, the method comprises culturing a host cell according to any one of the aspects, embodiments, cases, or examples, described herein and the metabolic product is a cannabinoid. In some embodiments, the cannabinoid is THCA, CBDA, CBCA, CBN, THC, CBD, or CBC, or a mixture of one or more thereof. In some embodiments, the method comprises culturing a host cell according to any one of the aspects, embodiments, cases, or examples described herein and the metabolic product is a terpenoid or is isoprene. In some embodiments, the method comprises harvesting and lysing the cultured cells, thereby producing cell lysate. In some embodiments, the method comprises purifying the target metabolic product from the cell lysate, thereby producing a purified target metabolic product. In some embodiments, the method comprises purifying the target metabolic product from the spent culture medium, thereby producing a purified target metabolic product.

In some embodiments, the purified target metabolic product is a cannabinoid and the method comprises formulating the cannabinoid in a pharmaceutical composition. In some embodiments, the purified target metabolic product is a cannabinoid and the method comprises forming a salt, prodrug, or solvate of the purified cannabinoid.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE FIGURES

FIG. 14 shows a table of optimized inducer concentrations for the indicated expression constructs in *E. coli*.

FIG. 19 illustrates a protein sequence alignment of a bifunctional ispDF enzyme identified from a metagenomics screening assay (ispDF1) (SEQ ID NO: 1) with native ispD and ispF (ispD-ispF) (SEQ ID NO: 42) and *C. jejuni* ispDF (CJ-ispDF) (SEQ ID NO: 41).

FIG. 26 illustrates peptide sequences of the bifunctional enzymes ispDF1, ispDF2, and ispDF3. SEQ ID NOs: 1-3 are disclosed in order of appearance.

DETAILED DESCRIPTION OF THE INVENTION

Described herein is a metabolic engineering strategy for increased production of terpenoids by altering the mevalonate-independent (MEP) pathway. The MEP, or terpenoid, pathway produces geranyl pyrophosphate (GPP), a product that can be used in a variety of downstream processes to produce commercially valuable terpenoids and other compounds.

Also described herein is a bifunctional enzyme ispDF that can catalyze both of the reactions performed by native *E. coli* ispD and ispF. The bifunctional enzyme can be used in a variety of in vitro or in vivo isoprene, terpenoid, or cannabinoid production systems. In some embodiments, a metabolic engineering strategy described herein, with or without ispDF can be used to increase the production of isoprene, GPP, or a downstream terpenoid in a heterologous host cell.

Figure 1:
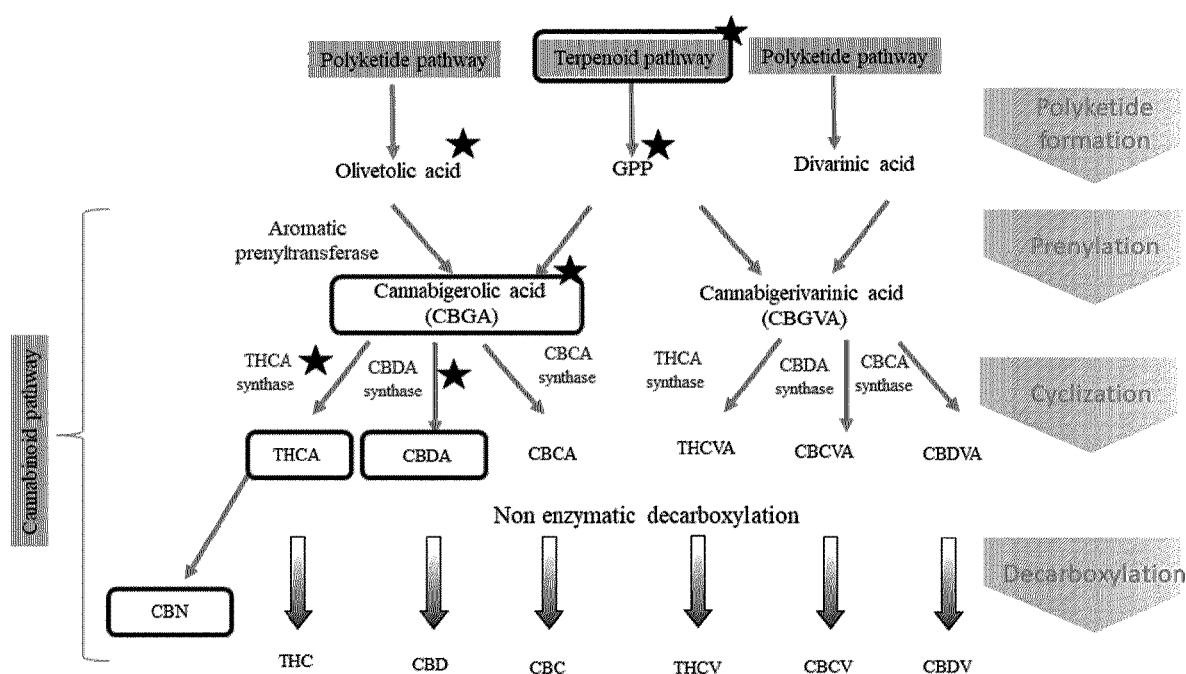
FIG. 1 is a diagram showing an overview of cannabinoid synthesis in *Cannabis sativa*.

GPP is a substrate for the first enzyme of cannabinoid pathway, cannabigerolic acid synthase (CBGAS), an aromatic prenyltransferase enzyme (FIG. 1). CBGAS uses the substrates GPP and olivetolic acid (OA) to produce cannabigerolic acid (CBGA). In some cases, the CBGA can be used as a substrate for further in vitro or in vivo enzyme-catalyzed reactions, such as to produce $\Delta^9$-tetrahydrocannabinolic acid (THCA) via a reaction catalyzed by THCA synthase (THCAS) or cannabidiolic acid (CBDA) via a reaction catalyzed by CBDA synthase (CBDAS). Additional pathways for production of cannabinoids include, but are not limited to, those described in Thakur et al., Life Sciences, 78 (2005) 454-466. Thakur et al., is herein incorporated by reference in the entirety and for all purposes, including but not limited to, the enzymes, products, enzyme substrates, pathways and portions thereof, and synthetic schemes described therein.

In some embodiments, products of down-stream enzyme-catalyzed reactions involving the substrate CBGA, THCA, CBDA, CBCA, THCVA, CBCVA, CBDVA, and combinations thereof, can be decarboxylated in vitro or in vivo using chemical, enzymatic, or thermal means to produce various cannabinoids, for example as depicted in FIG. 1.

Definitions

The following abbreviations are used herein: "G3P" means glyceraldehyde 3-phosphate; "DOXP" means 1-Deoxy-D-xylulose 5-phosphate; "MEP" means 2-C-methylerythritol 4-phosphate; "CDP-ME" means 4-diphosphocytidyl-2-C-methylerythritol; "CDP-MEP" means 4-diphosphocytidyl-2-C-methyl-D-erythritol 2-phosphate; "MECPP" means 2-C-methyl-D-erythritol 2,4-cyclodiphosphate; "HMBPP" means (E)-4-Hydroxy-3-methyl-but-2-enyl pyrophosphate; "IPP" means isopentenyl disphosphate; "DMAPP" means dimethylallyl diphosphate; "GPP" means geranyl pyrophosphate.

"DXP pathway" and "MEP pathway" refer to the non-mevalonate pathway, also known as the mevalonate-independent pathway. The genes of the MEP pathway are dxs, ispC, ispD, ispE, ispF, ispG, ispH, and idi. In reference to DXP or MEP pathway genes or gene products, or a nucleic acid encoding same, the gene can be a native gene of a host cell in which the, e.g., heterologous nucleic acid resides, a codon optimized version thereof, a gene derived (e.g., codon optimized) from a different organism, or an orthologue thereof.

"dxs" refers to DOXP synthase; "ispC" refers to DOXP reductase; "ispD" refers to 2-C-methyl-D-erythritol 4-phosphate cytidylyltransferase; "ispE" refers to 4-diphosphocytidyl-2-C-methyl-D-erythritol kinase; "ispF" refers to 2-C-methyl-D-erythritol 2,4-cyclodiphosphate synthase; "ispG" refers to HMB-PP synthase; "ispH" refers to HMB-PP reductase; "idi" refers to isopentenyl/dimethylallyl diphosphate isomerase; "ispA" refers to farnesyl diphosphate synthase, also known as "GPP synthase," which can convert DMAPP+IPP to GPP and GPP+IPP to farnesyl pyrophosphate.

The term "ispDF" refers to a bifunctional single-chain enzyme having two different active sites and exhibiting ispD activity (EC 2.7.7.60) and ispF activity (EC 4.6.1.12). Typically, ispDF is a naturally occurring bifunctional enzyme or a derivative of a naturally occurring bifunctional enzyme having one or more modifications such as a deletion, insertion, or substitution of one or more amino acids. In some cases, the gene is plant-derived, or a *Cannabis* gene. In some cases, the gene is an *E. coli* gene, or an orthologue thereof.

"OA" refers to olivetolic acid; "CBGA" refers to cannabigerolic acid; "CBNA" refers to cannabinerolic acid; "cannabinol" or "CBN" refers to 6,6,9-trimethyl-3-pentylbenzo[c]chromen-1-ol; "CBGVA" refers to cannabigerivarinic acid; "THCA" refers to tetrahydrocannabinolic acid, including the $\Delta^9$ isomer; "CBDV" refers to cannabidivarin; "CBC" refers to cannabichromene; "CBCA" refers to cannabichromenic acid; "CBCV" refers to cannabichromevarin; "CBG refers to cannabigerol; "CBGB" refers to cannabigerovarin; "CBE" refers to cannabielsoin; "CBL" refers to cannabicyclol; "CBV" refers to cannabivarin; "CBT" refers to cannabitriol; "THCV" refers to tetrahydrocannibivarin (THCV); "THC" refers to tetrahydrocannabinol, and "$\Delta^9$-THC" refers to $\Delta^9$-tetrahydrocannabinol; "CBDA" refers to cannabidiolic acid.

As used herein "increased flux through the MEP pathway" refers to an increased production of IPP and/or DMAPP. Typically, production of IPP and/or DMAPP is determined indirectly by detecting product formed by the action of a reporter enzyme that utilizes IPP and/or DMAPP as a reactant. For example, increased flux through the MEP pathway can be detected as increased isoprene production by using isoprene synthase (ispS) as a reporter. As another example, increased flux through the MEP pathway can be detected as increased GPP production by using GPP synthase as a reporter. In some cases, the GPP production is detected using a reporter enzyme. For example, increased GPP production can be detected by detecting increased lycopene production using a GPP synthase enzyme and a lycopene synthase reporter enzyme, thereby detecting increased flux through the MEP pathway. As another example, increased GPP production can be detected by detecting increased monoterpene (e.g., limonene, carene, myrcene) production using a GPP synthase enzyme and a monoterpene (e.g., limonene, carene, myrcene) synthase reporter enzyme, thereby detecting increased flux through the MEP pathway. As another example, increased GPP production can be detected by detecting increased cannabinoid (e.g., CBGA) production using a GPP synthase enzyme and a cannabinoid (e.g., CBGA) synthase reporter enzyme, thereby detecting increased flux through the MEP pathway. Typically, the increase is at least 10% as compared to a control strain lacking one or more heterologous expression cassettes in the test strain. In some cases, the increase is at least 2-fold as compared to a control strain lacking one or more heterologous expression cassettes in the test strain.

As used herein, the terms "cannabidiol," "CBD," or "cannabidiols" refer to one or more of the following compounds, and, unless a particular other stereoisomer or stereoisomers are specified, includes the compound "$\Delta^2$-cannabidiol." These compounds are: (1) $\Delta^5$-cannabidiol (2-(6-isopropenyl-3-methyl-5-cyclohexen-1-yl)-5-pentyl-1,3-benzenediol); (2) $\Delta^4$-cannabidiol (2-(6-isopropenyl-3-methyl-4-cyclohexen-1-yl)-5-pentyl-1,3-benzenediol); (3) $\Delta^3$-cannabidiol (2-(6-isopropenyl-3-methyl-3-cyclohexen-1-yl)-5-pentyl-1,3-benzenediol); (4) $\Delta^{3,7}$-cannabidiol (2-(6-isopropenyl-3-methylenecyclohex-1-yl)-5-pentyl-1,3-benzenediol); (5) $\Delta^2$-cannabidiol (2-(6-isopropenyl-3-methyl-2-cyclohexen-1-yl)-5-pentyl-1,3-benzenediol); (6) $\Delta^1$-cannabidiol (2-(6-isopropenyl-3-methyl-1-cyclohexen-1-yl)-5-pentyl-1,3-benzenediol); and (7) $\Delta^6$-cannabidiol (2-(6-isopropenyl-3-methyl-6-cyclohexen-1-yl)-5-pentyl-1,3-benzenediol).

These compounds have one or more chiral centers and two or more stereoisomers as stated below: (1) (1) $\Delta^5$-cannabidiol has 2 chiral centers and 4 stereoisomers; (2) $\Delta^4$-cannabidiol has 3 chiral centers and 8 stereoisomers; (3) $\Delta^3$-cannabidiol has 2 chiral centers and 4 stereoisomers; (4) $\Delta^{3,7}$-cannabidiol has 2 chiral centers and 4 isomers; (5) $\Delta^2$-cannabidiol has 2 chiral centers and 4 stereoisomers; (6) $\Delta^1$-cannabidiol has 2 chiral centers and 4 stereoisomers; and (7) $\Delta^6$-cannabidiol has 1 chiral center and 2 stereoisomers. In a preferred embodiment, canabidiol is specifically $\Delta^2$-cannabidiol. Unless specifically stated, a reference to "cannabidiol," "CBD," or "cannabidiols" or to any of specific cannabidiol compounds (1)-(7) as referred to above includes all possible stereoisomers of all compounds included by the reference. In one embodiment, "$\Delta^2$-cannabidiol" can be a mixture of the $\Delta^2$-cannabidiol stereoisomers that are partially or entirely produced in a heterologous system.

The term "isoprenoid" or "terpenoid" refers to any compound comprising one or more five-carbon isoprene building blocks, including linear and cyclic terpenoids. As used herein, the term "terpene" is interchangeable with terpenoid and isoprenoid. When terpenes are modified chemically, such as by oxidation or rearrangement of the carbon chain, the resulting compounds are generally referred to as terpenoids, also called isoprenoids.

Terpenoids can be named according to the number of carbon atoms present, using groups of 5 and 10 carbons as a reference. For example a hemiterpenoid (C5) has one isoprene unit (a half-terpenoid); a monoterpenoid (C10) has two isoprene units (one terpenoid); a sesquiterpenoid (C15) has three isoprene units (1.5 terpenoids); and a diterpenoid (C20) has four isoprene units (or two terpenoids). Typically, a monoterpenoid is produced in nature from the C10 terpenoid precursor geranyl pyrophosphate (GPP). Similarly, a "cyclic monoterpene" refers to a cyclic or aromatic terpenoid (i.e., comprising a ring structure). It is made from two isoprene building blocks, typically from GPP. Linear monoterpenes include but are not limited to geraniol, linalool, ocimene, and myrcene. Cyclic monoterpenes (monocyclic, bicyclic and tricyclic) include, but are not limited to, limonene, pinene, carene, terpineol, terpinolene, phellandrene, thujene, tricyclene, borneol, sabinene, and camphene.

A "terpenoid synthase" refers to an enzyme capable of catalyzing the conversion of one terpenoid or terpenoid precursor to another terpenoid or terpenoid precursor. For example, a GPP synthase is an enzyme that catalyzes the formation of GPP, e.g. from the terpenoid precursors IPP and DMAPP. Similarly, an FPP synthase is an enzyme that catalyzes the production of FPP, e.g. from GPP and IPP. Terpene synthases are enzymes that catalyze the conversion of a prenyl diphosphate (such as GPP) into an isoprenoid or an isoprenoid precursor. The term includes both linear and cyclic terpene synthases.

A "cyclic terpenoid synthase" refers to an enzyme capable of catalyzing a reaction that modifies a terpenoid or terpenoid precursor to provide a ring structure. For example, a cyclic monoterpenoid synthase refers to an enzyme capable of using a linear monoterpene as a substrate to produce a cyclic or aromatic (ring-containing) monoterpenoid compound. One example would be sabinene synthase, which is capable of catalyzing the formation of the cyclic monoterpene sabinene from the linear monoterpene precursor GPP. As used herein, the term "terpene synthase" is interchangeable with terpenoid synthase.

A prenyl transferase or isoprenyl transferase enzyme, also called a prenyl or isoprenyl synthase is an enzyme capable of catalyzing the production of a pyrophosphate precursor of a terpenoid or isoprenoid compound. An exemplary prenyl transferase or isoprenyl transferase enzyme is ispA, which is capable of catalyzing the formation of geranyl diphosphate (GPP) or farnesyl diphosphate (FPP) in the presence of a suitable substrate.

A "cannabinoid synthase" refers to an enzyme that catalyzes one or more of the following activities: cyclization of CBGA to THCA, CBDA, or CBCA; cyclization of CBGVA to THCVA, CBCVA, CBDVA, prenylation of olivetolic acid to form CBGA, and combinations thereof. Exemplary cannabinoid synthases include, but are not limited to those found naturally occurring in a plant of the genus *Cannabis*, such as THCA synthase, CBDA synthase, and CBCA synthase of *Cannabis sativa*.

Exemplary isoprenoid, terpenoid, cannabinoid, and MEP pathway polypeptides and nucleic acids include those described in the KEGG database. The KEGG database contains the amino acid and nucleic acid sequences of numerous exemplary isoprenoid, terpenoid, cannabinoid, and MEP pathway polypeptides and nucleic acids (see, for example, the world-wide web at "genomejp/kegg/pathway/map/map00100.html" and the sequences therein, which are each hereby incorporated by reference in their entireties, particularly with respect to the amino acid and nucleic acid sequences of isoprenoid, terpenoid, cannabinoid, and MEP pathway polypeptides and nucleic acids). Polypeptides described herein that contain a signal peptide, and nucleic acids that encode them, are understood to further describe a truncated version in which a signal peptide is removed or otherwise absent.

As used herein, the term "heterologous" refers to any two components that are not naturally found together. For example, a nucleic acid encoding a gene that is heterologous to an operably linked promoter is a nucleic acid having expression that is not controlled in its natural state (e.g., within a non-genetically modified cell) by the promoter to which it is operably linked in a particular genome. As provided herein, all genes operably linked to non-naturally occurring promoters are considered "heterologous." Similarly, a gene that is "heterologous" to a host cell is a gene that is not found in a non-genetically modified cell of a particular organism or that is found in a different genomic or non-genomic (e.g., plasmid) location, or operably linked to a different promoter in the non-genetically modified cell. Additionally, a promoter that is "heterologous" to a host cell is a promoter that is not found in a non-genetically modified cell of a particular organism or that is found in a different genomic or non-genomic (e.g., plasmid) location, or operably linked to a different nucleic acid in the non-genetically modified cell.

As used herein, an "expression cassette" refers to the polynucleotide sequences comprising a promoter polynucleotide operably linked to at least one target gene, wherein the promoter is heterologous to at least one operably-linked gene, the promoter is heterologous to a host cell in which it resides, or at least one operably-linked gene is heterologous to the host cell, or a combination thereof.

"Salt" refers to acid or base salts of the compounds used in the methods of the present invention. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

As used herein, the term "solvate" means a compound formed by solvation (the combination of solvent molecules with molecules or ions of the solute), or an aggregate that consists of a solute ion or molecule, i.e., a compound of the invention, with one or more solvent molecules. When water is the solvent, the corresponding solvate is "hydrate." Examples of hydrate include, but are not limited to, hemihydrate, monohydrate, dihydrate, trihydrate, hexahydrate, and other water-containing species. It should be understood by one of ordinary skill in the art that the pharmaceutically acceptable salt, and/or prodrug of a compound may also exist in a solvate form. The solvate is typically formed via hydration which is either part of the preparation of a compound or through natural absorption of moisture by an anhydrous compound of the present invention. In general, all physical forms are intended to be within the scope of the present invention.

Thus, when a therapeutically active agent made in a method according to the present invention or included in a composition according to the present invention, such as, but not limited to, a cannabinoid or a terpenoid, possesses a sufficiently acidic, a sufficiently basic, or both a sufficiently acidic and a sufficiently basic functional group, these group or groups can accordingly react with any of a number of inorganic or organic bases, and inorganic and organic acids, to form a pharmaceutically acceptable salt. Exemplary pharmaceutically acceptable salts include those salts prepared by reaction of the pharmacologically active compound with a mineral or organic acid or an inorganic base, such as salts including sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, isobutyrates, caproates, heptanoates, propiolates, oxalates, malonates, succinates, suberates, sebacates, fumarates, maleate s, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, β-hydroxybutyrates, glycolates, tartrates, methane-sulfonates, propanesulfonates, naphthalene-1-sulfonates, naphthalene-2-sulfonates, and mandelates. If the pharmacologically active compound has one or more basic functional groups, the desired pharmaceutically acceptable salt may be prepared by any suitable method available in the art, for example, treatment of the free base with an inorganic acid, such as hydrochloric acid, hydrobromic acid, sulfuric acid, nitric acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha-hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the pharmacologically active compound has one or more acidic functional groups, the desired pharmaceutically acceptable salt may be prepared by any suitable method available in the art, for example, treatment of the free acid with an inorganic or organic base, such as an amine (primary, secondary or tertiary), an alkali metal hydroxide or alkaline earth metal hydroxide, or the like. Illustrative examples of suitable salts include organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

"Composition" as used herein is intended to encompass a product comprising the specified ingredients in the specified amounts, as well as any product that results from combination of the specified ingredients in the specified amounts. By "pharmaceutically acceptable" it is meant the carrier, diluent or excipient must be compatible with the other ingredients of the formulation and not deleterious to the recipient thereof.

"Pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

In some cases, protecting groups can be included in compounds used in methods according to the present invention or in compositions according to the present invention. The use of such a protecting group is to prevent subsequent hydrolysis or other reactions that can occur in vivo and can degrade the compound. Groups that can be protected include alcohols, amines, carbonyls, carboxylic acids, phosphates, and terminal alkynes. Protecting groups useful for protecting alcohols include, but are not limited to, acetyl, benzoyl, benzyl, β-methoxyethoxyethyl ether, dimethoxytrityl, methoxymethyl ether, methoxytrityl, p-methoxybenzyl ether, methylthiomethyl ether, pivaloyl, tetrahydropyranyl, tetrahydrofuran, trityl, silyl ether, methyl ether, and ethoxyethyl ether. Protecting groups useful for protecting amines include carbobenzyloxy, p-methoxybenzy lcarbonyl, t-butyloxycarbonyl, 9-fluorenylmethyloxycarbonyl, acetyl, benzoyl, benzyl, carbamate, p-methoxybenzyl, 3,4-dimethoxybenzyl, p-methoxyphenyl, tosyl, trichloroethyl chloroformate, and sulfonamide Protecting groups useful for protecting carbonyls include acetals, ketals, acylals, and dithianes Protecting groups useful for protecting carboxylic acids include methyl esters, benzyl esters, t-butyl esters, esters of 2,6-disubstituted phenols, silyl esters, orthoesters, and oxazoline. Protecting groups useful for protecting phosphate groups include 2-cyanoethyl and methyl. Protecting groups useful for protecting terminal alkynes include propargyl alcohols and silyl groups. Other protecting groups are known in the art.

As used herein, the term "prodrug" refers to a precursor compound that, following administration, releases the biologically active compound in vivo via some chemical or physiological process (e.g., a prodrug on reaching physiological pH or through enzyme action is converted to the biologically active compound). A prodrug itself may either lack or possess the desired biological activity. Thus, the term "prodrug" refers to a precursor of a biologically active compound that is pharmaceutically acceptable. n certain cases, a prodrug has improved physical and/or delivery properties over a parent compound from which the prodrug has been derived. The prodrug often offers advantages of solubility, tissue compatibility, or delayed release in a mammalian organism (H. Bundgard, *Design of Prodrugs* (Elsevier, Amsterdam, 1988), pp. 7-9, 21-24). A discussion of prodrugs is provided in T. Higuchi et al., "Pro-Drugs as Novel Delivery Systems," *ACS Symposium Series,* Vol. 14 and in E. B. Roche, ed., *Bioreversible Carriers in Drug Design* (American Pharmaceutical Association & Pergamon Press, 1987). Exemplary advantages of a prodrug can include, but are not limited to, its physical properties, such as enhanced drug stability for long-term storage.

The term "prodrug" is also meant to include any covalently bonded carriers which release the active compound in vivo when the prodrug is administered to a subject. Prodrugs of a therapeutically active compound, as described herein, can be prepared by modifying one or more functional groups present in the therapeutically active compound, including cannabinoids, terpenoids, and other therapeutically active compounds used in methods according to the present invention or included in compositions according to the present invention, in such a way that the modifications are cleaved, either in routine manipulation or in vivo, to yield the parent therapeutically active compound. Prodrugs include compounds wherein a hydroxy, amino, or mercapto group is covalently bonded to any group that, when the prodrug of the active compound is administered to a subject, cleaves to form a free hydroxy, free amino, or free mercapto group, respectively. Examples of prodrugs include, but are not limited to, formate or benzoate derivatives of an alcohol or acetamide, formamide or benzamide derivatives of a therapeutically active agent possessing an amine functional group available for reaction, and the like.

For example, if a therapeutically active agent or a pharmaceutically acceptable form of a therapeutically active agent contains a carboxylic acid functional group, a prodrug can comprise an ester formed by the replacement of the hydrogen atom of the carboxylic acid group with a group such as $C_{1-8}$ alkyl, $C_{2-12}$ alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N($C_1$-$C_2$)alkylamino($C_2$-$C_3$)alkyl (such as (3-dimethylaminoethyl), carbamoyl-($C_1$-$C_2$)alkyl, N,N-di ($C_1$-$C_2$)alkylcarbamoyl-($C_1$-$C_2$)alkyl and piperidino-, pyrrolidino-, or morpholino($C_2$-$C_3$)alkyl.

Similarly, if a disclosed compound or a pharmaceutically acceptable form of the compound contains an alcohol functional group, a prodrug can be formed by the replacement of the hydrogen atom of the alcohol group with a group such as ($C_1$-$C_6$)alkanoyloxymethyl, 1-(($C_1$-$C_6$))alkanoyloxy) ethyl, 1-methyl-1-(($C_1$-$C_6$)alkanoyloxy)ethyl ($C_1$-$C_6$) alkoxycarbonyloxymethyl, N($C_1$-$C_6$)alkoxycarbonylaminomethyl, succinoyl, ($C_1$-$C_6$)alkanoyl, α-amino($C_1$-$C_4$)

alkanoyl, arylacyl and α-aminoacyl, or α-aminoacyl-α-aminoacyl, where each α-aminoacyl group is independently selected from the naturally occurring L-amino acids, P(O)(OH)$_2$, P(O)(O(C$_1$-C$_6$)alkyl)$_2$ or glycosyl (the radical resulting from the removal of a hydroxyl group of the hemiacetal form of a carbohydrate).

If a disclosed compound or a pharmaceutically acceptable form of the compound incorporates an amine functional group, a prodrug can be formed by the replacement of a hydrogen atom in the amine group with a group such as R-carbonyl, RO-carbonyl, NRR'-carbonyl where R and R' are each independently (C$_1$-C$_{10}$)alkyl, (C$_3$-C$_7$)cycloalkyl, benzyl, or R-carbonyl is a natural α-aminoacyl or natural α-aminoacyl-natural α-aminoacyl, C(OH)C(O)OY$^1$ wherein Y$^1$ is H, (C$_1$-C$_6$)alkyl or benzyl, C(OY$^2$)Y$^3$ wherein Y$^2$ is (C$_1$-C$_4$) alkyl and Y$^3$ is (C$_1$-C$_6$)alkyl, carboxy(C$_1$-C$_6$)alkyl, amino(C$_1$-C$_4$)alkyl or mono-N or di-N,N(C$_1$-C$_6$)alkylaminoalkyl,C(Y$^4$)Y$^5$ wherein Y$^4$ is H or methyl and Y$^5$ is mono-N or di-N,N(C$_1$-C$_6$)alkylamino, morpholino, piperidin-1-yl or pyrrolidin-1-yl.

The use of prodrug systems is described in T. Järvinen et al., "Design and Pharmaceutical Applications of Prodrugs" in *Drug Discovery Handbook* (S. C. Gad, ed., Wiley-Interscience, Hoboken, N.J., 2005), ch. 17, pp. 733-796. Other alternatives for prodrug construction and use are known in the art. When a method or pharmaceutical composition according to the present invention, uses or includes a prodrug of a cannabinoid, terpenoid, or other therapeutically active agent, prodrugs and active metabolites of a compound may be identified using routine techniques known in the art. See, e.g., Bertolini et al., J. Med. Chem., 40, 2011-2016 (1997); Shan et al., J. Pharm. Sci., 86 (7), 765-767; Bagshawe, Drug Dev. Res., 34, 220-230 (1995); Bodor, Advances in Drug Res., 13, 224-331 (1984); Bundgaard, Design of Prodrugs (Elsevier Press 1985); Larsen, Design and Application of Prodrugs, Drug Design and Development (Krogsgaard-Larsen et al., eds., Harwood Academic Publishers, 1991); Dear et al., J. Chromatogr. B, 748, 281-293 (2000); Spraul et al., J. Pharmaceutical & Biomedical Analysis, 10, 601-605 (1992); and Prox et al., Xenobiol., 3, 103-112 (1992).

Cannabinoids

Cannabinoids are a group of chemicals known to activate cannabinoid receptors in cells throughout the human body, including the skin. Phytocannabinoids are the cannabinoids derived from cannabis plants. They can be isolated from plants or produced synthetically. Endocannabinoids are endogenous cannabinoids found in the human body. Canonical phytocannabinoids are ABC tricyclic terpenoid compounds bearing a benzopyran moiety.

Cannabinoids exert their effects by interacting with cannabinoid receptors present on the surface of cells. To date, two types of cannabinoid receptor have been identified, the CB1 receptor and the CB2 receptor. These two receptors share about 48% amino acid sequence identity, and are distributed in different tissues and also have different signaling mechanisms. They also differ in their sensitivity to agonists and antagonists.

Accordingly, in vitro and in vivo methods are described herein for screening for and identifying genes, promoters, and expression cassettes for in vivo production of cannabinoids.

Typically, the methods and compositions described herein can be used for production, or increased production of one or more terpenoids, such as cannabinoids in a host cell, or production of one or more terpenoid or cannabinoid precursors in a host cell. In some cases, the terpenoids or cannabinoids or precursors thereof, can be purified, derivatized (e.g., to form a prodrug, solvate, or salt, or to form the target terpenoid or cannabinoid from the precursor), and/or formulated in a pharmaceutical composition.

The cannabinoids that can be produced according to the methods and/or using the compositions of the present invention include but are not limited to phytocannabinoids. In some cases the cannabinoids include but are not limited to, cannabinol, cannabidiols, $\Delta^9$-tetrahydrocannabinol ($\Delta^9$-THC), the synthetic cannabinoid HU-210 (6aR,10aR)-9-(hydroxymethyl)-6,6-dimethyl-3-(2-methyloctan-2-yl)-6H, 6aH,7H,10H,10aH-benzo[c]isochromen-1-ol), cannabidivarin (CBDV), cannabichromene (CBC), cannabichromevarin (CBCV), cannabigerol (CBG), cannabigerovarin (CBGV), cannabielsoin (CBE),cannabicyclol (CBL), cannabivarin (CBV), and cannabitriol (CBT). Still other cannabinoids include, including tetrahydrocannibivarin (THCV) and cannabigerol monomethyl ether (CBGM). Additional cannabinoids include cannabichromenic acid (CBCA), $\Delta^9$-tetrahydrocannabinolic acid (THCA); and cannabidiolic acid (CBDA); these additional cannabinoids are characterized by the presence of a carboxylic acid group in their structure.

Still other cannabinoids include nabilone, rimonabant, JWH-018 (naphthalen-1-yl-(1-pentylindol-3-yl)methanone), JWH-073 naphthalen-1-yl-(1-butylindol-3-yl)methanone, CP-55940 (2-[(1R,2R,5R)-5-hydroxy-2-(3-hydroxypropyl) cyclohexyl]-5-(2-methyloctan-2-yl)phenol), dimethylheptylpyran, HU-331 (3-hydroxy-2-[(1R)-6-isopropenyl-3-methyl-cyclohex-2-en-1-yl]-5-pentyl-1,4-benzoquinone), SR144528 (5-(4-chloro-3-methylphenyl)-1-[(4-methylphenyl)methyl]-N-[(1S,2S,4R)-1,3,3-trimethylbicyclo[2.2.1]heptan-2-yl]-1H-pyrazole-3-carboxamide), WIN 55,212-2 ((11R)-2-methyl-11-[(morpholin-4-yl)methyl]-3-(naphthalene-1-carbonyl)-9-oxa-1-azatricyclo[6.3.1.0$^{4,12}$] dodeca-2,4(12),5,7-tetraene), JWH-133 ((6aR,10aR)-3-(1,1-dimethylbutyl)-6a,7,10,10a-tetrahydro-6,6,9-trimethyl-6H-dibenzo[b,d]pyran), levonatradol, and AM-2201 (1-[(5-fluoropentyl)-1H-indol-3-yl]-(naphthalen-1-yl)methanone). Other cannabinoids include $\Delta^8$-tetrahydrocannabinol ($\Delta^8$-THC), 11-hydroxy-$\Delta^9$-tetrahydrocannabinol, $\Delta^{11}$-tetrahydrocannabinol, and 11-hydroxy-tetracannabinol.

In another alternative, analogs or derivatives of these cannabinoids can be obtained by production of cannabinoid precursors and further derivatization, e.g., by synthetic means. Synthetic cannabinoids include, but are not limited to, those described in U.S. Pat. No. 9,394,267 to Attala et al.; U.S. Pat. No. 9,376,367 to Herkenroth et al.; U.S. Pat. No. 9,284,303 to Gijsen et al.; U.S. Pat. No. 9,173,867 to Travis; U.S. Pat. No. 9,133,128 to Fulp et al.; U.S. Pat. No. 8,778,950 to Jones et al.; U.S. Pat. No. 7,700,634 to Adam-Worrall et al.; U.S. Pat. No. 7,504,522 to Davidson et al.; U.S. Pat. No. 7,294,645 to Barth et al.; U.S. Pat. No. 7,109,216 to Kruse et al.; U.S. Pat. No. 6,825,209 to Thomas et al.; and U.S. Pat. No. 6,284,788 to Mittendorf et al.

In another alternative, the cannabinoid can be an endocannabinoid or a derivative or analog thereof. Endocannabinoids include but are not limited to anandamide, 2-arachidonoylglycerol, 2-arachidonyl glyceryl ether, N-arachidonoyl dopamine, and virodhamine A number of analogs of endocannabinoids are known, including 7,10,13,16-docosatetraenoylethanolamide, oleamide, stearoylethanolamide, and homo-γ-linolenoylethanolamine, are also known.

Cannabinoids produced in methods and compositions according to the present invention can be either selective for the CB2 cannabinoid receptor or non-selective for the two cannabinoid receptors, binding to either the CB1 cannabinoid receptor or the CB2 cannabinoid receptor. In some cases, cannabinoids produced in methods and compositions according to the present invention are selective for the CB2 cannabinoid receptor. In some cases, the cannabinoids, or one of the cannabinoids in a mixture of cannabinoids is an antagonist (e.g., selective or non-selective antagonist) of CB2. In some cases, cannabinoids produced in methods and compositions according to the present invention are selective for the CB2 cannabinoid receptor. In some cases, the cannabinoids, or one of the cannabinoids in a mixture of cannabinoids is an antagonist (e.g., selective or non-selective antagonist) of CB1.

Expression Cassettes

Described herein are expression cassettes suitable for expressing one or more target genes in a host cell. The expression cassettes described herein can be a component of a plasmid or integrated into a host cell genome. A single plasmid can contain one or more expression cassettes described herein. As used herein, where two or more expression cassettes are described, it is understood that alternatively at least two of the two or more expression cassettes can be combined to reduce the number of expression cassettes. Similarly, where multiple target genes are described as operably linked to a single promoter and thus described as components of a single expression cassette, it is understood that the single expression cassette can be sub-divided into two or more expression cassettes containing overlapping or non-overlapping subsets of the single described expression cassette.

An expression cassette described herein can contain a suitable promoter as known in the art. In some cases, the promoter is a constitutive promoter. In other cases, the promoter is an inducible promoter. In preferred embodiments, the promoter is a T5 promoter, a T7 promoter, a Trc promoter, a Lac promoter, a Tac promoter, a Trp promoter, a tip promoter, a $\lambda P_L$ promoter, a $\lambda P_R$ promoter, a $\lambda P_R P_L$ promoter, an arabinose promoter (araBAD), and the like. In some embodiments, the promoter is selected from the group consisting of the E. coli promoters described in Zaslaver et al., Nat Methods. 2006 August; 3(8):623-8, which is hereby incorporated by reference in the entirety, particularly with respect to promoters, expression cassettes, including plasmids, for the expression of nucleic acids of interest, target genes, host cells, and combinations thereof described therein. Promoters, which are useful to drive expression of one or more target genes in various host cells are numerous and familiar to those skilled in the art (see, for example, WO 2004/033646; U.S. Pat. Nos. 8,507,235; 8,715,962; and WO 2011/017798, and references cited therein, which are each hereby incorporated by reference in their entireties, particularly with respect to promoters, expression cassettes, including plasmids, for the expression of nucleic acids of interest, target genes, host cells, and combinations thereof described therein.

Methods and compositions described herein can be used for expression of one or more genes of the MEP pathway, and/or production of one or more products of the MEP pathway in a suitable host cell. In some embodiments, MEP pathway flux is increased by overexpression of one or more endogenous components of the host cell by amplification of gene copy number and/or operably linking an endogenous gene (or copy thereof) to a strong constitutive or inducible heterologous promoter. Accordingly, in one embodiment, an expression cassette comprising a promoter operably linked to a nucleic acid encoding one or more genes of the MEP pathway is provided. In E. coli, endogenous MEP pathway genes are dxs, ispC, ispD, ispE, ispF, ispG, ispH, and idi.

In some cases, the promoter of the expression cassette is operably linked to a nucleic acid encoding two or more genes of the MEP pathway. In some cases, the promoter of the expression cassette is operably linked to a nucleic acid encoding three or more genes of the MEP pathway. In some cases, the promoter of the expression cassette is operably linked to a nucleic acid encoding four, five, six, or all eight genes of the MEP pathway. In some cases, the genes of the MEP pathway provided in the expression cassette are E. coli genes. In other cases, one or more of the genes of the MEP pathway provided in the expression cassette are genes that are heterologous to wild-type E. coli. In some cases, one or more genes of the MEP pathway are provided in a first expression cassette and one or more genes of the MEP pathway are provided in a second expression cassette. In a preferred embodiment, an expression cassette comprising a promoter operably linked to dxs and idi is provided.

In some cases, an expression cassette is provided that comprises a promoter operably linked to a nucleic acid encoding one or more genes of the MEP pathway and further encoding a GPP synthase, a cannabinoid synthase, or an isoprene synthase. In some cases, an expression cassette is provided that comprises a promoter operably linked to a nucleic acid encoding one or more genes of the MEP pathway and further encoding THCA synthase. In some cases, an expression cassette is provided that comprises a promoter operably linked to a nucleic acid encoding one or more genes of the MEP pathway and further encoding CBGA synthase. In some cases, an expression cassette is provided that comprises a promoter operably linked to a nucleic acid encoding one or more genes of the MEP pathway and further encoding CBCA synthase. In some cases, an expression cassette is provided that comprises a promoter operably linked to a nucleic acid encoding one or more genes of the MEP pathway and further encoding CBDA synthase.

In some embodiments, an expression cassette containing a promoter operably linked to a nucleic acid encoding a bifunctional ispDF enzyme is provided. The ispDF gene can be used in addition to, or as an alternative to, overexpression of native ispD and/or ispF in the host cell. In some cases, the nucleic acid encodes an ispDF protein having the following amino acid sequence (SEQ ID NO. 1):

MIALQRSLSMHVTAIIAAAGEGRRLGAPLPKQLLDIGGRSILERSVMAFAR

HERIDDVIVVLPPALAAAPPDWIAASGRVPAVHVVSGGERRQDSVANAFDR

VPAQSDVVLVHDAARPFVTAELISRAIDGAMQHGAAIVAVPVRDTVKRVDP

DGEHPVITGTIPRDTIYLAQTPQAFRRDVLGAAVALGRSGVSATDEAMLAE

QAGHRVHVVEGDPANVKITTSADLDQARQRLRSAVAARIGTGYDLHRLIEG

RPLIIGGVAVPCDKGALGHSDADVACHAVIDALLGAAGAGNVGQHYPDTDP

RWKGASSIGLLRDALRLVQERGFTVENVDVCVVLERPKIAPFIPEIRARIA

GALGIDPERVSVKGKTNEGVDAVGRGEAIAAHAVALLSES.

In other embodiments, the ispDF nucleic acid encodes an ispDF protein having at least 32%, 40%, 45%, 50%, 52%, 55%, 60%, 65%, 70%, 80%, 85%, 90%, 95%, or 99% identity with respect to SEQ ID NO.1. In yet other embodiments, the ispDF nucleic acid encodes an ispDF protein having at least 32%, 40%, 45%, 50%, 52%, 55%, 60%, 65%, 70%, 80%, 85%, 90%, 95%, or 99% identity with respect to at least 300 contiguous amino acids of SEQ ID NO.1.

In some cases, the bifunctional ispDF has a primary amino acid sequence that is no more than 75% identical to at least 300 contiguous amino acids of *H. pylori* HP1020, *H. pylori* HP1020, *H. pylori* J99 jhp0404, *H. pylori* HPAG1 HPAG1_0427, *H. hepaticus* HH1582, *H. acinonychis* st. Sheeba Hac_1124, *W. succinogenes* DSM 1740 WS1940, *S. denitrificans* DSM 1251 Suden_1487, *C. jejuni* subsp. *jejuni* NCTC 11168 Cj1607, *C. jejuni* RM1221 CJE1779, *C. jejuni* subsp. *jejuni* 81-176 CJJ81176_1594, and *C. fetus* subsp. *fetus* 82-40 CFF8240_0409. In some cases, the bifunctional ispDF is not *H. pylori* HP1020, *H. pylori* HP1020, *H. pylori* J99 jhp0404, *H. pylori* HPAG1 HPAG1_0427, *H. hepaticus* HH1582, *H. acinonychis* st. Sheeba Hac_1124, *W. succinogenes* DSM 1740 WS1940, *S. denitrificans* DSM 1251 Suden_1487, *C. jejuni* subsp. *jejuni* NCTC 11168 Cj1607, *C. jejuni* RM1221 CJE1779, *C. jejuni* subsp. *jejuni* 81-176 CJJ81176_1594, or *C. fetus* subsp. *fetus* 82-40 CFF8240_0409.

The bifunctional ispDF can be encoded by a nucleic acid within a plasmid. Alternatively, the bifunctional ispDF can be encoded by a nucleic acid that is integrated into the genome of a heterologous host cell. In some cases, a heterologous promoter is operably linked to the nucleic acid encoding the bifunctional ispDF. Additionally or alternatively, a host cell can be heterologous to the nucleic acid encoding the bifunctional ispDF.

The nucleic acid encoding the bifunctional ispDF can be in an MEP pathway expression cassette such as any one of the foregoing expression cassettes that contain a nucleic acid encoding an MEP pathway gene. In some cases, the nucleic acid encoding the bifunctional ispDF can be in an expression cassette that contains a nucleic acid encoding a cannabinoid synthase. In some cases, the nucleic acid encoding the bifunctional ispDF can be in an expression cassette that contains a nucleic acid encoding GPP synthase. In some cases, the nucleic acid encoding the bifunctional ispDF can be in an expression cassette that contains a nucleic acid encoding an isoprene synthase.

Methods and compositions described herein can be used for production of GPP from precursors produced in the MEP pathway in a suitable host cell. Accordingly, in some embodiments, an expression cassette comprising a promoter operably linked to a nucleic acid encoding GPP synthase is provided. The GPP synthase can be in an expression cassette that also contains nucleic acid encoding a gene of the MEP pathway. Additionally, or alternatively, the GPP synthase can be in an expression cassette that also contains nucleic acid encoding a cannabinoid synthase. In some cases, the promoter of the expression cassette that is operably linked to a nucleic acid encoding GPP synthase is also operably linked to a cannabinoid synthase. Additionally, or alternatively, the GPP synthase can be in an expression cassette that also contains nucleic acid encoding a GPP synthase. Additionally, or alternatively, the GPP synthase can be in an expression cassette that also contains nucleic acid encoding an isoprene synthase.

Methods and compositions described herein can be used for production of cannabinoids in a host cell. Accordingly, in some embodiments, an expression cassette comprising a promoter operably linked to a nucleic acid encoding a cannabinoid synthase is provided. The cannabinoid synthase can be a cannabinoid synthase endogenous to a plant of the genus *Cannabis,* or an orthologue thereof. In some cases, the cannabinoid synthase is a cannabinoid synthase endogenous to *Cannabis sativa* or *Cannabis indica,* or an orthologue thereof. In some cases, the cannabinoid synthase is CBGA synthase, THCA synthase, CBDA synthase, or CBCA synthase (e.g., endogenous to a plant of the genus *Cannabis,* or an orthologue thereof).

The cannabinoid synthase can be modified for expression in a host. For example, one or more transmembrane or signal peptide domains can be truncated. Additionally, or alternatively, one or more glycosylation sites can be deleted (e.g., by mutation of the primary amino acid sequence). Similarly, one or more or all cysteines found in an intramolecular disulfide bond in the native protein in its native host can be mutated, e.g., to serine. Similarly, one or more or all cysteines found in an intermolecular disulfide bond in the native protein in its native host can be mutated, e.g., to serine.

Host Cells

Any of the foregoing expression cassettes, and combinations thereof, can be introduced into a suitable host cell and used for production of a target terpenoid or cannabinoid. Suitable host cells include, but are not limited to prokaryotes, such as a prokaryote of the genus *Escherichia, Panteoa, Corynebacterium, Bacillus,* or *Lactococcus.* Preferred prokaryote host cells include, but are not limited to, *Escherichia coli* (*E. coli*), *Panteoa citrea, C. glutamicum, Bacillus subtilis,* and *Lactococcus lactis.* In some embodiments, the expression cassettes described herein comprise a promoter (e.g., heterologous promoter) operably linked to a nucleic acid that encodes one or more target genes (e.g., a MEP pathway gene, a cannabinoid synthase gene, ispA, ispS, ispDF, or GPP synthase), wherein the nucleic acid encoding the one or more target genes is codon optimized for the host cell that comprises the expression cassette.

In some cases, the host cell comprises one or more products of the MEP pathway, such as DMAPP and/or IPP. For example, a host cell containing an MEP pathway expression cassette as described herein can comprise an increased amount of an MEP pathway product such as DMAPP and/or IPP as compared to a host cell that does not contain an MEP pathway expression cassette.

In some cases, the host cell can comprise one or more products that are downstream of the MEP pathway. For example, a host cell comprising a GPP synthase expression cassette can comprise an increased amount of GPP as compared to a host cell lacking the GPP synthase expression cassette. As another example, a host cell comprising an isoprene synthase expression cassette can comprise an increased amount of isoprene as compared to a host cell lacking the isoprene synthase expression cassette.

As yet another example, a host cell comprising a cannabinoid synthase expression cassette can comprise an increased amount of cannabinoid as compared to a host cell lacking the cannabinoid synthase expression cassette. In some cases, the cannabinoid is CBGA. In some cases, the cannabinoid is CBCA. In some cases, the cannabinoid is CBDA. In some cases, the cannabinoid is THCA. In some cases, the cannabinoid is CBN. In some cases, the cannabinoid is CBD. In some cases, the cannabinoid is THC. In some cases, the cannabinoid is CBC. In some cases, the cannabinoid is THCV. In some cases, the cannabinoid is CBDV. In some cases, the cannabinoid is CBCV.

Similarly, the host cell can comprise an elevated amount of a product of one or more enzymes encoded by an expression cassette in the host cell when the host cell is cultured under conditions suitable to induce expression from the expression cassette as compared to non-inducing conditions. For example, the host cell can exhibit increased DMAPP and/or IPP when induced as compared to the same host cell cultured in the absence of an inducer (e.g., in the absence of IPTG, arabinose, etc.). As another example, the host cell can exhibit increased GPP when induced as compared to the same host cell cultured in the absence of an inducer (e.g., in the absence of IPTG, arabinose, etc.). As another example, the host cell can exhibit increased isoprene when induced as compared to the same host cell cultured in the absence of an inducer (e.g., in the absence of IPTG, arabinose, etc.). As another example, the host cell can exhibit increased cannabinoid when induced as compared to the same host cell cultured in the absence of an inducer (e.g., in the absence of IPTG, arabinose, etc.).

In some embodiments, the host cell comprises olivetolic acid (OA). OA can be introduced into the host cell by culturing the host cell in a medium containing OA. In some embodiments, the host cell comprises divarinic acid (DVA). DVA can be introduced into the host cell by culturing the host cell in a medium containing DVA.

In some embodiments, the host cell is genetically modified to delete or reduce the expression of one or more genes that encode an endogenous enzyme that reduces flux through the MEP pathway. In some embodiments, the host cell is genetically modified to delete or reduce the amount or activity of an endogenous enzyme that reduces flux through the MEP pathway. For example, pyruvate and glyceraldehyde-3 phosphate (G3P) are the substrates of the initial enzyme of the MEP pathway dxs. Endogenous pathways that consume pyruvate and G3P can be modified to increase the amount of pyruvate and G3P thus increasing the flux through the MEP pathway. In some cases, one or more host cell endogenous genes or gene products selected from the group consisting of ackA-pta, poxB, ldhA, dld, adhE, pps, and atoDA are modified to increase pyruvate or G3P levels.

Culture Methods

The present invention furthermore provides a process for culturing a host cell according to the present invention in a suitable medium under induction conditions, resulting in production of a target metabolic product. The target metabolic product can be a cannabinoid, a terpenoid, or a precursor thereof. The method can include concentrating the metabolite in the spent medium and/or in the host cells.

The microorganisms produced may be cultured continuously—as described, for example, in WO 05/021772—or discontinuously in a batch process (batch cultivation) or in a fed-batch or repeated fed-batch process for the purpose of producing the desired organic-chemical compound. A summary of a general nature about known cultivation methods is available in the textbook by Chmiel (BioprozeStechnik 1: Einfiihrung in die Bioverfahrenstechnik (Gustav Fischer Verlag, Stuttgart, 1991)) or in the textbook by Storhas (Bioreaktoren and periphere Einrichtungen (Vieweg Verlag, Braunschweig/Wiesbaden, 1994)).

The culture medium or fermentation medium to be used must in a suitable manner satisfy the demands of the respective strains. Descriptions of culture media for various microorganisms are present in the "Manual of Methods for General Bacteriology" of the American Society for Bacteriology (Washington D.C., USA, 1981). The terms culture medium and fermentation medium are interchangeable.

It is possible to use, as carbon source, sugars and carbohydrates such as, for example, glucose, sucrose, lactose, fructose, maltose, molasses, sucrose-containing solutions from sugar beet or sugar cane processing, starch, starch hydrolysate, and cellulose; oils and fats such as, for example, soybean oil, sunflower oil, groundnut oil and coconut fat; fatty acids such as, for example, palmitic acid, stearic acid, and linoleic acid; alcohols such as, for example, glycerol, methanol, and ethanol; and organic acids such as, for example, acetic acid or lactic acid.

It is possible to use, as nitrogen source, organic nitrogen-containing compounds such as peptones, yeast extract, meat extract, malt extract, corn steep liquor, soybean flour, and urea; or inorganic compounds such as ammonium sulfate, ammonium chloride, ammonium phosphate, ammonium carbonate, and ammonium nitrate. The nitrogen sources can be used individually or as a mixture.

It is possible to use, as phosphorus source, phosphoric acid, potassium dihydrogen phosphate or dipotassium hydrogen phosphate or the corresponding sodium-containing salts.

The culture medium may additionally comprise salts, for example in the form of chlorides or sulfates of metals such as, for example, sodium, potassium, magnesium, calcium and iron, such as, for example, magnesium sulfate or iron sulfate, which are necessary for growth. Finally, essential growth factors such as amino acids, for example homoserine and vitamins, for example thiamine, biotin or pantothenic acid, may be employed in addition to the abovementioned substances.

Said starting materials may be added to the culture in the form of a single batch or be fed in during the cultivation in a suitable manner.

The pH of the culture can be controlled by employing basic compounds such as sodium hydroxide, potassium hydroxide, ammonia, or aqueous ammonia; or acidic compounds such as phosphoric acid or sulfuric acid in a suitable manner. The pH is generally adjusted to a value of from 6.0 to 8.5, preferably 6.5 to 8. To control foaming, it is possible to employ antifoams such as, for example, fatty acid polyglycol esters. To maintain the stability of plasmids, it is possible to add to the medium suitable selective substances such as, for example, antibiotics. The culturing is preferably carried out under aerobic conditions. In order to maintain these conditions, oxygen or oxygen-containing gas mixtures such as, for example, air are introduced into the culture. It is likewise possible to use liquids enriched with hydrogen peroxide. The culturing is carried out, where appropriate, at elevated pressure, for example at an elevated pressure of from 0.03 to 0.2 MP a. The temperature of the culture is normally from 20° C. to 45° C. and preferably from 25° C. to 40° C., particularly preferably from 30° C. to 37° C. In batch or fed-batch processes, the cultivation is preferably continued until an amount of the desired organic-chemical compound sufficient for being recovered has formed. This aim is normally achieved within 10 hours to 160 hours. In continuous processes, longer cultivation times are possible. The activity of the microorganisms results in a concentration (accumulation) of the organic-chemical compound in the fermentation medium and/or in the cells of said microorganisms.

Examples of suitable culture media can be found inter alia in the patents U.S. Pat. Nos. 5,770,409, 5,990,350, 5,275, 940, WO 2007/012078, U.S. Pat. No. 5,827,698, WO 2009/043803, U.S. Pat. Nos. 5,756,345 and 7,138,266.

Analysis of target metabolic products to determine the concentration at one or more time(s) during the culturing can take place by separating the metabolites by means of chromatography, preferably reverse-phase chromatography.

Detection can be carried out carried out photometrically (absorption, fluorescence).

The performance of the culture methods using a host cell containing one or more expression cassettes according to the invention, in terms of one or more of the parameters selected from the group of concentration (target metabolic product formed per unit volume), yield (target metabolic product formed per unit carbon source consumed), formation (target metabolic product formed per unit volume and time) and specific formation (target metabolic product per unit dry cell matter or dry biomass and time or compound formed per unit cellular protein and time) or else other process parameters and combinations thereof, can be increased by at least 0.5%, at least 1%, at least 1.5%, at least 2%, at least 3%, at least 4%, at least 5%, at least 10%, at least 20%, at least 30%, at least 40%, at least 50%, at least 60%, at least 70%, at least 80%, at least 90%, or at least 100% based on culture methods using host cells that do not contain the expression cassettes according to the invention. This is considered to be very worthwhile in terms of a large-scale industrial process.

A product containing the target metabolic product can then be provided or produced or recovered in liquid or solid form.

Spent medium means a culture medium in which a host cell has been cultured for a certain time and at a certain temperature. The culture medium or the media employed during culturing comprise(s) all the substances or components which ensure production of the desired target metabolic product and typically propagation and viability. When the culturing is complete, the resulting spent medium accordingly comprises: a) the biomass (cell mass) of the microorganism, said biomass having been produced due to propagation of the cells of said microorganism; b) the desired target metabolic product formed during the culturing; c) the organic byproducts possibly formed during the culturing; and d) the constituents of the culture medium employed or of the starting materials, such as, for example, vitamins such as biotin or salts such as magnesium sulfate, which have not been consumed in the culturing.

The organic byproducts include substances which are produced by the microorganisms employed in the culturing in addition to the particular desired compound and are optionally secreted. The spent medium can be removed from the culture vessel or fermentation tank, collected where appropriate, and used for providing a product containing the target metabolic product in liquid or solid form. In the simplest case, the target metabolic product-containing spent medium itself, which has been removed from the fermentation tank, constitutes the recovered product.

In some cases, recovering the target metabolic product (e.g., terpenoid, cannabinoid, or precursor thereof) includes, but is not limited to, one or more of the measures selected from the group consisting of a) partial (>0% to <80%) to complete (100%) or virtually complete (>80%, >90%, >95%, >96%, >97%, >98%, or >99%) removal of the water; b) partial (>0% to <80%) to complete (100%) or virtually complete (>80%, >90%, >95%, >96%, >97%, >98%, or >99%) removal of the biomass, the latter being optionally inactivated before removal; c) partial (>0% to <80%) to complete (100%) or virtually complete (>80%, >90%, >95%, >96%, >97%, >98%, >99%, >99.3%, or >99.7%) removal of the organic byproducts formed during culturing; and d) partial (>0%) to complete (100%) or virtually complete (>80%, >90%, >95%, >96%, >97%, >98%, >99%, >99.3%, or >99.7%) removal of the constituents of the fermentation medium employed or of the starting materials, which have not been consumed in the culturing, from the spent medium achieves concentration or purification of the desired target metabolic product. Compositions having a desired content of said target metabolic product are isolated in this way.

The partial (>0% to <80%) to complete (100%) or virtually complete (>80% to <100%) removal of the water (measure a)) is also referred to as drying.

In one variant of the process, complete or virtually complete removal of the water, of the biomass, of the organic byproducts and of the unconsumed constituents of the fermentation medium employed results in pure (>80% by weight, >90% by weight) or high-purity (>95% by weight, >97% by weight, or >99% by weight) product forms of the desired target metabolic product. An abundance of technical instructions for measures a), b), c) and d) are available in the prior art.

Depending on requirements, the biomass can be removed wholly or partly from the spent medium by separation methods such as, for example, centrifugation, filtration, decantation or a combination thereof, or be left completely therein. Where appropriate, the biomass or the biomass-containing spent medium is inactivated during a suitable process step, for example by thermal treatment (heating) or by addition of alkaline or acid.

In one procedure, the biomass is completely or virtually completely removed so that no (0%) or at most 30%, at most 20%, at most 10%, at most 5%, at most 1% or at most 0.1% biomass remains in the prepared product. In a further procedure, the biomass is not removed, or is removed only in small proportions, so that all (100%) or more than 70%, 80%, 90%, 95%, 99% or 99.9% biomass remains in the product prepared. In one process according to the invention, accordingly, the biomass is removed in proportions of from >0% to <100%. Finally, the fermentation broth obtained after the fermentation can be adjusted, before or after the complete or partial removal of the biomass, to an acidic pH with an inorganic acid such as, for example, hydrochloric acid, sulfuric acid, or phosphoric acid; or organic acid such as, for example, propionic acid, so as to improve the handling properties of the final product (GB 1,439,728 or EP 1 331220). It is likewise possible to acidify the fermentation broth with the complete content of biomass. Finally, the broth can also be stabilized by adding sodium bisulfite (NaHCO3, GB 1,439,728) or another salt, for example ammonium, alkali metal, or alkaline earth metal salt of sulfurous acid.

During the removal of the biomass, any organic or inorganic solids present in the spent medium can be partially or completely removed. The organic byproducts dissolved in the spent medium, and the dissolved unconsumed constituents of the fermentation medium (starting materials), can remain at least partly (>0%), in some cases to an extent of at least 25%, in some cases to an extent of at least 50% and in some cases to an extent of at least 75% in the product. Where appropriate, they also remain completely (100%) or virtually completely, meaning >95% or >98% or >99%, in the product.

Subsequently, water can be removed from the spent medium, or said spent medium can be thickened or concentrated, by known methods such as, for example, using a rotary evaporator, thin-film evaporator, falling-film evaporator, by reverse osmosis or by nanofiltration. This concentrated spent medium can then be worked up to free-flowing products, in particular to a fine powder or preferably coarse granules, by methods of freeze drying, spray drying, spray granulation or by other processes such as in the circulating fluidized bed, as described for example according to PCT/EP2004/006655.

Pharmaceutical Compositions

The target metabolic product can be formulated into a pharmaceutical composition. In some cases spent medium or concentrated spent medium, or a partially or entirely purified target metabolic product from the spent medium or biomass obtained in the culturing methods described herein, is formulated into a pharmaceutical composition.

Pharmaceutical compositions according to the present invention can include one or more excipients. Such excipients that are suitable for use in topical compositions intended for application to the skin include, but are not limited to: preservatives; thickening agents; buffers; liquid carriers; isotonic agents; wetting, solubilizing, and emulsifying agents; acidifying agents; antioxidants; alkalinizing agents; carrying agents; chelating agents; complexing agents; solvents; suspending or viscosity-increasing agents; oils; penetration enhancers; polymers; stiffening agents; proteins; carbohydrates; and bulking agents.

As is generally known in the art of pharmaceutical formulation, a particular excipient can fulfill one or more of these functions in a particular pharmaceutical composition, depending on the concentration of the excipient, the other excipients in the composition, the physical form of the composition, the concentration of active agent in the composition, the intended route of administration of the composition, and other factors. The recitation of a particular excipient in a category below is not intended to exclude the possible use of the excipient in another category or categories.

The liquid carrier can be, but is not limited to, a liquid carrier selected from the group consisting of saline, phosphate buffered saline, glycerol, and ethanol A thickening agent can be, but is not limited to, a thickening agent selected from the group consisting of glycerol and propylene glycol.

An isotonic agent can be, but is not limited to: a polyalcohol selected from the group consisting of mannitol and sorbitol; sodium chloride; and potassium chloride.

The wetting, solubilizing, or emulsifying agent is generally a surfactant. Typically, the surfactant is selected from the group consisting of benzalkonium chloride, benzethonium chloride, cetylpyridinium chloride, docusate sodium, nonoxynol 9, nonoxynol 10, octoxynol 9, poloxamer, polyoxyl 35 castor oil, polyoxyl 40, hydrogenated castor oil, polyoxyl 50 stearate, polyoxyl 10 oleyl ether, polyoxyl 20, cetostearyl ether, polyoxyl 40 stearate, polysorbate 20, polysorbate 40, polysorbate 60, polysorbate 80, sodium lauryl sulfate, sorbitan monolaureate, sorbitan monooleate, sorbitan monopalmitate, sorbitan monostearate, tyloxapol, acacia, cholesterol, diethanolamine, glyceryl monostearate, lanolin alcohols, lecithin, mono- and di-glycerides, monoethanolamine (adjunct), oleic acid (adjunct), oleyl alcohol (stabilizer), poloxamer, polyoxyethylene 50 stearate, polyoxyl 35 castor oil, polyoxyl 40 hydrogenated castor oil, polyoxyl 10 oleyl ether, polyoxyl 20 cetostearyl ether, polyoxyl 40 stearate, polysorbate 20, polysorbate 40, polysorbate 60, polysorbate 80, propylene glycol diacetate, propylene glycol monostearate, sodium lauryl sulfate, sodium stearate, sorbitan monolaurate, sorbitan monooleate, sorbitan monopalmitate, sorbitan monostearate, stearic acid, triethanolamine, emulsifying wax, cetomacrogol, and cetyl alcohol.

The pharmaceutical composition for topical application can include an emollient. As used herein, the term "emollient" refers to a hydrophobic agent that softens, smoothens and improves lipid content of the skin or other mucous membranes. Examples of suitable emollients for use include isostearic acid derivatives, isopropyl palmitate, lanolin oil, diisopropyl dimerate, diisopropyl adipate, dimethyl isosorbide, maleated soybean oil, octyl palmitat, isopropyl isostearate, cetyl alcohol, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl lanolate, pentaerythrityl tetrastearate, neopentylglycol dicaprylate/dicaprate, hydrogenated coco-glycerides, isononyl isononanoate, isotridecyl isononanoate, myristyl myristate, triisocetyl citrate, octyl dodecanol, octyl hydroxystearate, grape seed oil, one or more ceramides, cyclomethicone, and mixtures thereof. Other examples of other suitable emollients can also be found in the Cosmetic Bench Reference, pp. 1.19-1.22 (1996). One of skill in the art will appreciate that other emollients are useful in the present invention.

The preservative can be selected from the group consisting of benzalkonium chloride, benzalkonium chloride solution, benzethonium chloride, benzoic acid, benzyl alcohol, butylparaben, cetylpyridinium chloride, chlorobutanol, chlorocresol, cresol, dehydroacetic acid, diazolidinyl urea, ethylparaben, methylparaben, methylparaben sodium, phenol, phenylethyl alcohol, phenylmercuric acetate, phenylmercuric nitrate, potassium benzoate, potassium sorbate, propylparaben, propylparaben sodium, sodium benzoate, sodium dehydroacetate, sodium propionate, sorbic acid, thimerosal, and thymol.

The composition can include a buffer selected from the group consisting of acetic acid, ammonium carbonate, ammonium phosphate, boric acid, citric acid, lactic acid, phosphoric acid, potassium citrate, potassium metaphosphate, potassium phosphate monobasic, sodium acetate, sodium citrate, sodium lactate solution, dibasic sodium phosphate, monobasic sodium phosphate, sodium bicarbonate, Tris (Tris(hydroxymethyl)aminomethane), MOPS (3-(N-morpholino)propanesulfonic acid), HEPES (N-(2-hydroxyethyl)piperazine-N'-(2-ethanesulfonic acid), ACES (2-[(2-amino-2-oxoethyl)amino]ethanesulfonic acid), ADA (N-(2-acetamido)2-iminodiacetic acid), AMPSO (3-[(1,1-dimethyl-2-hydroxyethylamino]-2-propanesulfonic acid), BES (N,N-bis(2-hydroxyethyl)-2-aminoethanesulfonic acid, Bicine (N,N-bis(2-hydroxyethylglycine), Bis-Tris (bis-(2-hydroxyethyl)imino-tris(hydroxymethyl)methane, CAPS (3-(cyclohexylamino)-1-propanesulfonic acid), CAPSO (3-(cyclohexylamino)-2-hydroxy-1-propanesulfonic acid), CHES (2-(N-cyclohexylamino)ethanesulfonic acid), DIPSO (3-[N,N-bis(2-hydroxyethylamino]-2-hydroxy-propanesulfonic acid), HEPPS (N-(2-hydroxyethylpiperazine)-N'-(3-propanesulfonic acid), HEPPSO (N-(2-hydroxyethyl) piperazine-N'-(2-hydroxypropanesulfonic acid), MES (2-(N-morpholino)ethanesulfonic acid), triethanolamine, imidazole, glycine, ethanolamine, phosphate, MOPSO (3-(N-morpholino)-2-hydroxypropanesulfonic acid), PIPES (piperazine-N,N'-bis(2-ethanesulfonic acid), POPSO (piperazine-N,N'-bis(2-hydroxypropaneulfonic acid), TAPS (N-tris[hydroxymethyl)methyl-3-aminopropanesulfonic acid), TAPSO (3-[N-tris(hydroxymethyl)methylamino]-2-hydroxy-propanesulfonic acid), TES (N-tris(hydroxymethyl)methyl-2-aminoethanesulfonic acid), tricine (N-tris (hydroxymethyl)methylglycine), 2-amino-2-methyl-1,3-propanediol, and 2-amino-2-methyl-1-propanol.

Typically, the acidifying agent is selected from the group consisting of acetic acid, citric acid, fumaric acid, hydrochloric acid, diluted hydrochloric acid, malic acid, nitric acid, phosphoric acid, diluted phosphoric acid, sulfuric acid, and tartaric acid.

Typically, the antioxidant is selected from the group consisting of ascorbic acid, ascorbyl palmitate, butylated hydroxyanisole, butylated hydroxytoluene, hypophosphorous acid, monothioglycerol, propyl gallate, sodium ascorbate, sodium bisulfite, sodium formaldehyde sulfoxylate, sodium metabisulfite, sodium thiosulfate, sulfur dioxide, and tocopherol.

Typically, the alkalinizing agent is selected from the group consisting of strong ammonia solution, ammonium carbonate, diethanolamine, diisopropanolamine, potassium hydroxide, sodium bicarbonate, sodium borate, sodium carbonate, sodium hydroxide, and trolamine.

The carrying agent can be selected from the group consisting of corn oil, mineral oil, peanut oil, sesame oil, bacteriostatic sodium chloride and bacteriostatic water.

The chelating agent can be selected from the group consisting of edetate disodium, ethylenediaminetetraacetic acid, citric acid, and salicylates.

The complexing agent can be selected from the group consisting of ethylenediaminetetraacetic acid, salts of ethylenediaminetetraacetic acid, gentisic acid ethanolamide, and oxyquinoline sulfate.

The solvent can be selected from the group consisting of acetone, ethanol, diluted alcohol, amylene hydrate, benzyl benzoate, butyl alcohol, carbon tetrachloride, chloroform, corn oil, cottonseed oil, ethyl acetate, glycerol, hexylene glycol, isopropyl alcohol, methyl isobutyl ketone, mineral oil, oleic acid, peanut oil, polyethylene glycol, propylene carbonate, propylene glycol, sesame oil, water, sterile water, and purified water.

Typically, the suspending and/or viscosity-increasing agent is selected from the group consisting of acacia, agar, alginic acid, aluminum monostearate, bentonite, purified bentonite, magma bentonite, carbomers, carbomer 934p, carboxymethylcellulose calcium, carboxymethylcellulose sodium, carboxymethycellulose sodium 12, carrageenan, microcrystalline and carboxymethylcellulose sodium cellulose, dextrin, gelatin, guar gum, hydroxyethyl cellulose, hydroxypropyl cellulose, hydroxypropyl methylcellulose, magnesium aluminum silicate, methylcellulose, pectin, polyethylene oxide, polyvinyl alcohol, povidone, propylene glycol alginate, silicon dioxide, colloidal silicon dioxide, sodium alginate, tragacanth, Veegum, and xanthan gum.

Typically, the oil is selected from the group consisting of arachis oil, mineral oil, olive oil, sesame oil, cottonseed oil, safflower oil, corn oil, and soybean oil.

Typically, the penetration enhancer is selected from the group consisting of monohydroxy or polyhydroxy alcohols, mono- or polyvalent alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones, and ureas.

Typically, the polymer is selected from the group consisting of cellulose acetate, alkyl celluloses, hydroxy alkylcelluloses, acrylic polymers and copolymers, polyesters, polycarbonates, and polyanhydrides.

Typically, the stiffening agent is selected from the group consisting of hydrogenated castor oil, cetostearyl alcohol, cetyl alcohol, cetyl esters wax, hard fat, paraffin, polyethylene excipient, stearyl alcohol, emulsifying wax, white wax, and yellow wax.

Typically, the protein is selected from the group consisting of bovine serum albumin, human serum albumin (HSA), recombinant human albumin (rHA), gelatin, and casein.

Typically, the carbohydrate is selected from the group consisting of fructose, maltose, galactose, glucose, D-mannose, sorbose, lactose, sucrose, trehalose, cellobiose, raffinose, melezitose, maltodextrins, dextrans, starches, mannitol, maltitol, lactitol, xylitol, sorbitol, and myoinositol.

Typically, the bulking agent is selected from the group consisting of polypeptides and amino acids.

The composition can further comprise a a topical soothing agent for the skin, a topical anti-inflammatory agent, a topical anti-bacterial agent, a topical anti-fungal agent, a topical steroid, and a topical antioxidant.

Topical soothing agents for the skin typically include chamomile and aloe; other topical soothing agents are known in the art and can be used.

Topical anti-inflammatory agents typically include diclofenac, ketoprofen, ibuprofen, piroxicam, and indomethacin; other topical anti-inflammatory agents are known in the art and can be used.

Topical anti-bacterial agents typically include bacitracin, polymyxin B, erythromycin, sodium sulfacetamide, silver sulfadiazine, retapamulin, mupirocin, neomycin, and pramoxine; other topical anti-bacterial agents are known in the art and can be used.

Topical anti-fungal agents typically include benzoic acid, salicylic acid, undecylenic acid, ketoconazole, nystatin, naftifine, tolnaftate, miconazole, econazole, ciclopirox, oxiconazole, sertaconazole, efinaconazole, terbinafine, tavaborole, clotrimazole, sulconazole, and butenafine; other topical anti-fungal agents are known in the art and can be used.

Topical steroids typically include hydrocortisone, triamcinolone, fluocinolone, prednicarbate, desonide, betamethasone, halcinonide, diflorasone, fluocinolone, clobetasol, desoxymetasone, mometasone, clocortolone, fluticasone, fluocinonide, flurandrenolide, alclometasone, and halobetasol; other topical steroids are known in the art and can be used.

Topical antioxidants typically include vitamin C, vitamin E, and L-selenomethionine; other topical antioxidants are known in the art and can be used.

Other active agents can be included.

In an alternative, a number of these additional agents, such as a topical anti-inflammatory agent, a topical anti-bacterial agent, a topical anti-fungal agent, a topical steroid, and a topical anti-oxidant, can be administered separately, such as in one or more additional pharmaceutical compositions including one or more excipients as described above.

In some alternatives, including the use of prodrugs as described above, therapeutically active compounds used in methods and compositions according to the present invention, including but not limited to cannabinoids and terpenoids, are formed by covalently cross-linking one or more conjugation partners to the therapeutically active compound. Suitable reagents for cross-linking many combinations of functional groups are known in the art.

For example, electrophilic groups can react with many functional groups, including those present in proteins or polypeptides. Various combinations of reactive amino acids and electrophiles are known in the art and can be used. For example, N-terminal cysteines, containing thiol groups, can be reacted with halogens or maleimides. Thiol groups are known to have reactivity with a large number of coupling agents, such as alkyl halides, haloacetyl derivatives, maleimides, aziridines, acryloyl derivatives, arylating agents such as aryl halides, and others. These are described in G. T. Hermanson, "Bioconjugate Techniques" (Academic Press, San Diego, 1996), pp. 146-150.

The reactivity of the cysteine residues can be optimized by appropriate selection of the neighboring amino acid residues. For example, a histidine residue adjacent to the cysteine residue will increase the reactivity of the cysteine residue. Other combinations of reactive amino acids and electrophilic reagents are known in the art. For example, maleimides can react with amino groups, such as the ε-amino group of the side chain of lysine, particularly at higher pH ranges. Aryl halides can also react with such amino groups. Haloacetyl derivatives can react with the imidazolyl side chain nitrogens of histidine, the thioether group of the side chain of methionine, and the .epsilon.-amino group of the side chain of lysine. Many other electrophilic reagents are known that will react with the ε-amino group of the side chain of lysine, including, but not limited to, isothiocyanates, isocyanates, acyl azides, N-hydroxysuccinimide esters, sulfonyl chlorides, epoxides, oxiranes, carbonates, imidoesters, carbodiimides, and anhydrides. These are described in G. T. Hermanson, "Bioconjugate Techniques" (Academic Press, San Diego, 1996), pp. 137-146.

Additionally, electrophilic reagents are known that will react with carboxylate side chains such as those of aspartate and glutamate, such as diazoalkanes and diazoacetyl compounds, carbonyldiimidazole, and carbodiimides. These are described in G. T. Hermanson, "Bioconjugate Techniques" (Academic Press, San Diego, 1996), pp. 152-154. Furthermore, electrophilic reagents are known that will react with hydroxyl groups such as those in the side chains of serine and threonine, including reactive haloalkane derivatives. These are described in G. T. Hermanson, "Bioconjugate Techniques" (Academic Press, San Diego, 1996), pp. 154-158. In another alternative embodiment, the relative positions of electrophile and nucleophile (i.e., a molecule reactive with an electrophile) are reversed so that the protein has an amino acid residue with an electrophilic group that is reactive with a nucleophile and the targeting molecule includes therein a nucleophilic group. This includes the reaction of aldehydes (the electrophile) with hydroxylamine (the nucleophile), described above, but is more general than that reaction; other groups can be used as electrophile and nucleophile. Suitable groups are well known in organic chemistry and need not be described further in detail.

Additional combinations of reactive groups for cross-linking are known in the art. For example, amino groups can be reacted with isothiocyanates, isocyanates, acyl azides, N-hydroxysuccinimide (NHS) esters, sulfonyl chlorides, aldehydes, glyoxals, epoxides, oxiranes, carbonates, alkylating agents, imidoesters, carbodiimides, and anhydrides. Thiol groups can be reacted with haloacetyl or alkyl halide derivatives, maleimides, aziridines, acryloyl derivatives, acylating agents, or other thiol groups by way of oxidation and the formation of mixed disulfides. Carboxy groups can be reacted with diazoalkanes, diazoacetyl compounds, carbonyldiimidazole, carbodiimides. Hydroxyl groups can be reacted with epoxides, oxiranes, carbonyldiimidazole, N,N'-disuccinimidyl carbonate, N-hydroxysuccinimidyl chloroformate, periodate (for oxidation), alkyl halogens, or isocyanates. Aldehyde and ketone groups can react with hydrazines, reagents forming Schiff bases, and other groups in reductive amination reactions or Mannich condensation reactions. Still other reactions suitable for cross-linking reactions are known in the art. Such cross-linking reagents and reactions are described in G. T. Hermanson, "Bioconjugate Techniques" (Academic Press, San Diego, 1996).

The amount of a given therapeutically active agent, such as, but not limited to, a cannabinoid or terpenoid as described above, that is included in a unit dose of a pharmaceutical composition according to the present invention will vary depending upon factors such as the particular compound, disease condition and its severity, the identity (e.g., weight) of the subject in need of treatment, but can nevertheless be routinely determined by one skilled in the art. The selected dosage level depends upon a variety of pharmacokinetic factors including the activity of the particular therapeutic agent, the route of administration, the time of administration, the rate of excretion of the particular compound being employed, the severity of the condition, other health considerations affecting the subject, and the status of liver and kidney function of the subject.

It also depends on the duration of the treatment, other drugs, compounds and/or materials used in combination with the particular therapeutic agent employed, as well as the age, weight, condition, general health and prior medical history of the subject being treated, and like factors. Methods for determining optimal dosages are described in the art, e.g., Remington: *The Science and Practice of Pharmacy*, Mack Publishing Co., 20$^{th}$ ed., 2000. Optimal dosages for a given set of conditions can be ascertained by those skilled in the art using conventional dosage-determination tests in view of the experimental data for an agent.

The compositions of the invention or compositions employed according to the present invention may be manufactured using techniques generally known for preparing pharmaceutical compositions, e.g., by conventional techniques such as mixing, dissolving, granulating, dragee-making, levitating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations.

Pharmaceutical compositions according to the present invention are usually administered to the subjects on multiple occasions. Intervals between single dosages can be weekly, monthly or yearly. Intervals can also be irregular as indicated by therapeutic response or other parameters well known in the art. Alternatively, the pharmaceutical composition can be administered as a sustained release formulation, in which case less frequent administration is required. Dosage and frequency vary depending on the half-life in the subject of the pharmacologically active agent included in a pharmaceutical composition. The dosage and frequency of administration can vary depending on whether the treatment is prophylactic or therapeutic.

In prophylactic applications, a relatively low dosage is administered at relatively infrequent intervals over a long period of time. Some subjects may continue to receive treatment for the rest of their lives. In therapeutic applications, a relatively high dosage at relatively short intervals is sometimes required until progression of the disease is reduced or terminated, and preferably until the subject shows partial or complete amelioration of symptoms of disease. Thereafter, the subject can be administered a prophylactic regime.

U.S. Pat. No. 6,573,292 to Nardella, U.S. Pat. No. 6,921,722 to Nardella, U.S. Pat. No. 7,314,886 to Chao et al., and U.S. Pat. No. 7,446,122 by Chao et al., which disclose methods of use of various pharmacologically active agents and pharmaceutical compositions in treating a number of diseases and conditions, including cancer, and methods of determining the therapeutic effectiveness of such pharmacologically active agents and pharmaceutical compositions, are all incorporated herein by this reference.

REFERENCES

The following publications are incorporated herein by this reference. These publications are referred to herein by the numbers provided below. The inclusion of any publication in this list of publications is not to be taken as an admission that any publication referred to herein is prior art.

*JAMA.* 2006; 295(7): 761-775
*Comput Struct Biotechnol* J, 2012, 3, 1-11
*Biotechnol. Bioeng.* 2004 88, 909-915.
*Science* 2002, 298 (5599), 1790-3.

EXAMPLES

Example 1

Engineering the MEP Pathway in *E. coli*

The MEP pathway was selected for its thermodynamic favourability and the availability of a suitable bacterial host system. The MEP pathway is native to the host *E. coli*. *E. coli* BL21 (DE3) was chosen as the expression host in this experiment. Genes that encode rate-limiting enzymes in the MEP pathway were over expressed to maximize the production of cannabinoid precursor.

Figure 2:
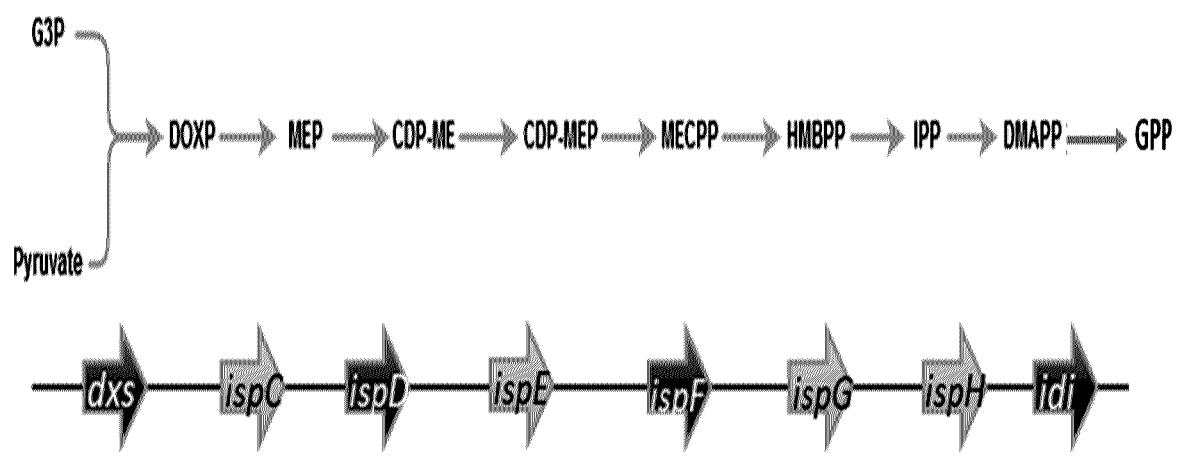
FIG. 2 is an illustration of the mevalonate-independent (MEP) pathway for biosynthesis of isoprenoid precursors in *E. coli*. Substrates and products are illustrated at top as follows: G3P (glyceraldehyde 3-phosphate), DOXP (1-Deoxy-D-xylulose 5-phosphate), MEP (2-C-methylerythritol 4-phosphate), CDP-ME (4-diphosphocytidyl-2-C-methylerythritol), CDP-MEP (4-diphosphocytidyl-2-C-methyl-D-erythritol 2-phosphate), MECPP (2-C-methyl-D-erythritol 2,4-cyclodiphosphate), HMBPP ((E)-4-Hydroxy-3-methylbut-2-enyl pyrophosphate), IPP (isopentenyl disphosphate), DMAPP (dimethylallyl diphosphate), GPP (geranyl pyrophosphate). Corresponding enzymes are illustrated at bottom as follows: dxs (DOXP synthase), ispC (DOXP reductase), ispD (2-C-methyl-D-erythritol 4-phosphate cytidylyltransferase), ispE (4-diphosphocytidyl-2-C-methyl-D-erythritol kinase), ispF (2-C-methyl-D-erythritol 2,4-cyclodiphosphate synthase), ispG (HMB-PP synthase), ispH (HMB-PP reductase), and idi (isopentenyl/dimethylallyl diphosphate isomerase).

Four steps in MEP pathway are slowest and suffer from low flux. Overexpression of the enzymes that catalyze these rate-limiting steps has been reported to improve flux through MEP pathway and increase downstream terpenoid biosynthesis. For maximizing the production of the precursors isopentenyl diphosphate (IPP) and dimethylallyl diphosphate (DMAPP) for a cannabinoid (FIG. 1), lycopene, monoterpene, or isoprene pathway, the non-mevalonate pathway was therefore engineered to introduce extra copies of the 4 different rate-limiting genes dxs, ispD, ispF and idi (FIG. 2).

Figure 3A:
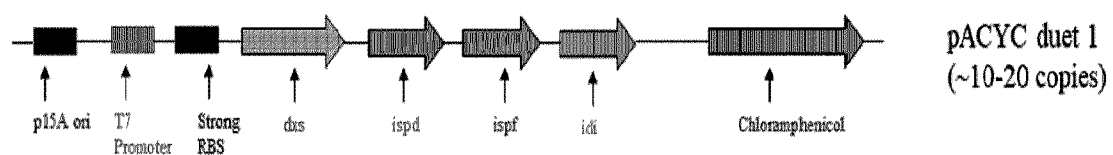
FIG. 3A-B is an illustration of two different expression cassettes for MEP pathway overexpression in a host cell.
Figure 3B:
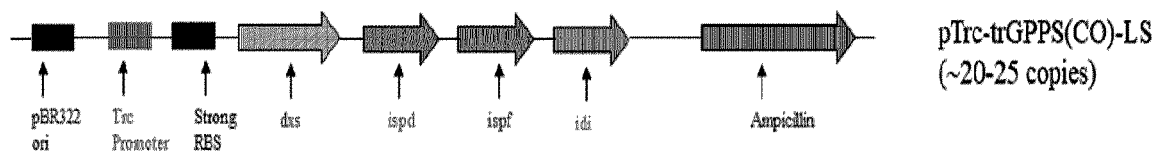
Figure 4:
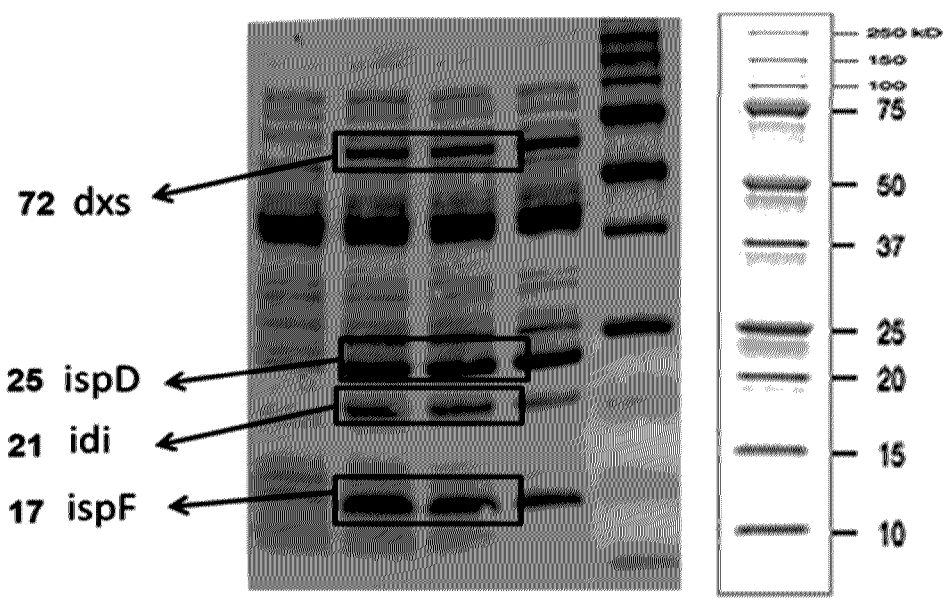
FIG. 4 illustrates an SDS-PAGE gel showing heterologous expression of dxs, ispD, idi, and ispF in a host cell.

This process was done in stepwise manner through polymerase chain reaction (PCR) and cloning into a vector backbone having a T7 promoter and p15A origin of replication, via restriction digestion and ligation, to construct a gene cassette with proper orientation. The entire gene cassette was then sub-cloned into a pTrc-trGPPS(CO)-LS plasmid (FIG. 3) with Trc promoter and pBR322 origin of replication to get a broad window to control the gene expression and thus the production of isoprenoid precursors. The gene cassette along with the pTrc promoter and selection marker gene was then be integrated into the *E. coli* chromosome as an inducible extra copy to provide overproduction of isoprenoid precursors. Schematic maps of the MEP pathway expression cassettes are shown in FIG. 3. The overexpression of rate limiting enzymes is confirmed by SDS Page analysis (FIG. 4).

Similarly, GPP synthase is cloned from, e.g., a plant source, and expressed in *E. coli* to produce GPP, a substrate of the cannabinoid synthase CBGA synthase and a substrate of monoterpene synthases such as carene, myrcene, or limonene synthase. Moreover, the polyketide pathway for synthesis of olivetolic acid, a substrate of CBGA synthase, is cloned and expressed in *E. coli*, or olivetolic acid is supplied exogenously. Thus, a pathway for production of CBGA is reproduced in a prokaryote host cell.

Example 2

Cloning and Expression of Downstream Pathway Cannabinoid Synthase Genes in *E. coli*

Introduction:

Cannabigerolic acid (CBGA) is the parent compound for the synthesis of other cannabinoids. CBGA is produced by the enzymatic reaction from olivetolic acid (OA) and geranyl pyrophosphate (GPP) catalyzed by CBGA synthase (an enzyme from aromatic prenyltransferase family). Cyclization of this prenylated product (CBGA) further gives three different cannabinoid products catalyzed by three different oxidocyclases. $\Delta^9$-tetrahydrocannabinolic acid (THCA) synthase, cannabidiolic (CBDA) synthase, and cannabichromenic acid (CBCA) synthase catalyzes the formation of $\Delta^9$-tetrahydrocannabinolic acid (THCA), cannabidiolic acid (CBDA) and cannabichromenic acid (CBCA), respectively. Biosynthesis of these cannabinoid products in microbial host (*E. coli*) involves cloning, expression, and activity determination of THCA synthase, CBGA synthase, CBCA synthase, CBDA synthase, and combinations thereof. Typically, cannabinoid products are produced in a microbial host expressing at least CBGA synthase, optionally in combination with one or more of THCA synthase, CBCA synthase, and CBDA synthase.

CBGA Synthase

Figure 5:
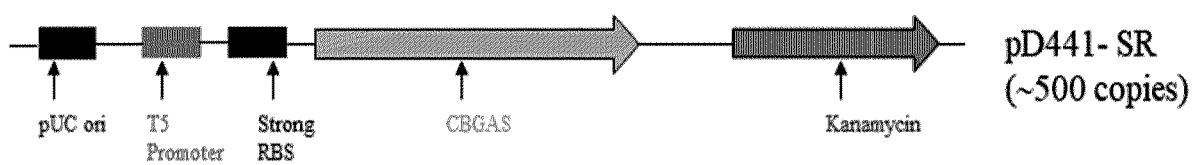
FIG. 5 illustrates an expression cassette for heterologous expression of cannabigerolic acid synthase (CBGAS) in a host cell.
Figure 6:
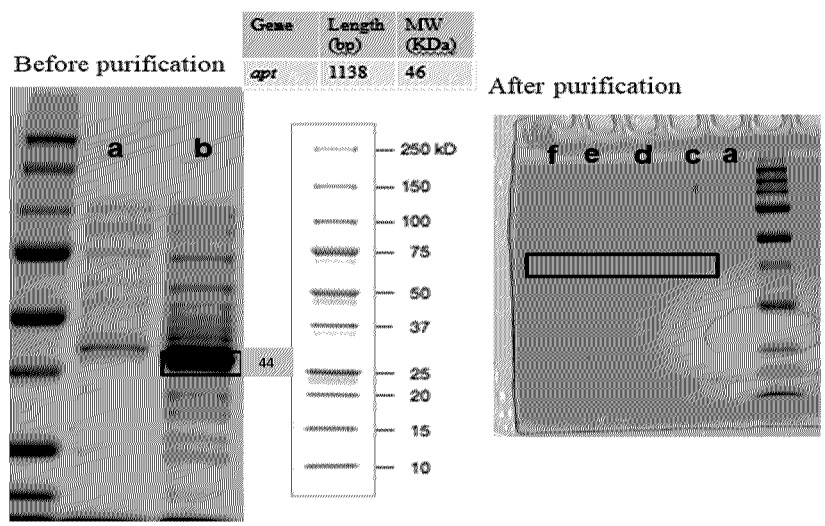
FIG. 6 illustrates an SDS PAGE gel showing expression and purification of a polyhistidine (6x-His)-tagged aromatic prenyltransferase ("6x-His" disclosed as SEQ ID NO: 43) in an *E. coli* host cell. Clarified cell lysate was loaded without purification. a: uninduced cell lysate; b-f: lysate of cells induced with 1 mM IPTG; c-f: Nickel-NTA column flow through fractions.
Figure 7:
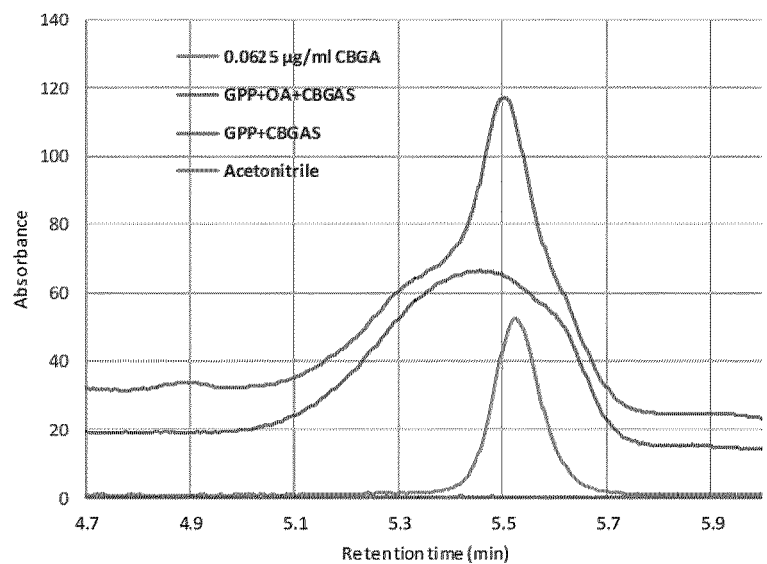
FIG. 7 is a chromatogram showing in vitro production of cannabigerolic acid (CBGA). The a line is a chromatogram for a CBGA standard at 0.0625 µg/mL; b is a reaction mixture containing CBGAS-induced cell lysate, olivetolic acid (OA), and GPP, c is the same reaction mixture but without GPP.

The CBGA synthase gene from *Cannabis sativa*, codon optimized for *E. coli*, was successfully cloned into a plasmid vector operably linked to a strong IPTG inducible T5 promoter. The plasmid contains the high copy pUC origin of replication, and is Kanamycin resistant. The plasmid construction for CBGA synthase is shown in FIG. 5. The expression of the CBGA synthase in *E. coli*. was confirmed by SDS PAGE analysis (FIG. 6). After confirming the expression of CBGAS, the activity of enzyme was determined by exogenously adding the substrates (OA and GPP) to the enzyme solution and the product profiling was done using in-house developed HPLC method. The prenylation reaction was carried out by adding clarified cell lysate to the mixture of OA and GPP at 37° C. and the reaction mixture was extracted by using ethyl acetate and ran on HPLC to measure the product formation. (FIG. 7) The results indicated that CBGAS can be expressed in *E. coli* and is capable of catalyzing a prenylation reaction with substrates OA and GPP to CBGA.

Figure 8:
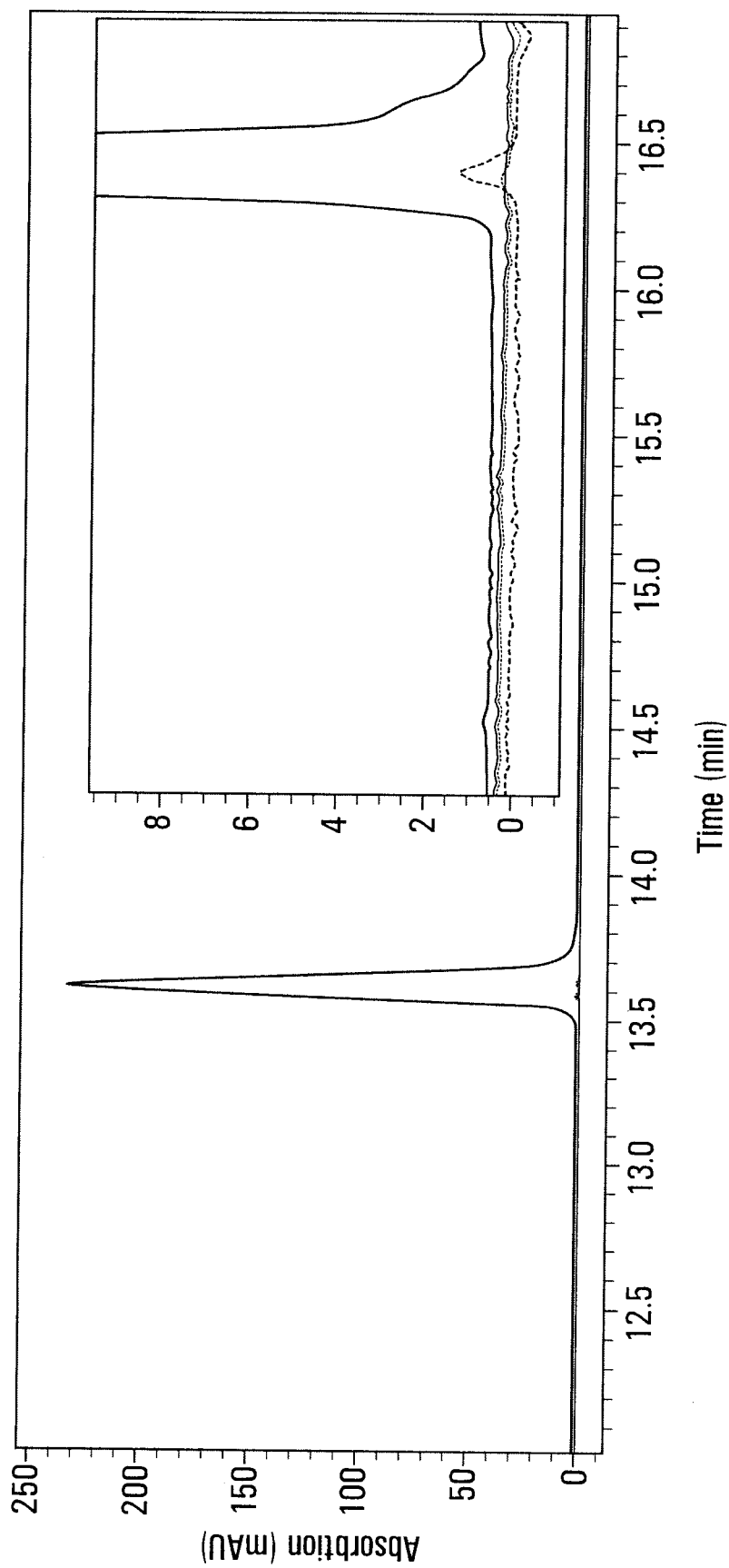
FIG. 8 is a chromatogram showing in vivo production of cannabigerolic acid (CBGA) in *E. coli*. The a line is a chromatogram for a CBGA standard at 0.5 µg/mL; b is spent culture media from growth of CBGAS-expressing *E. coli* supplemented with OA and GPP, c is the same reaction mixture but without OA.

In another experiment, the CBGA activity was tested in vivo. In this experiment, host cells containing the CBGAS expression plasmid were cultured and induced upon reaching log-phase growth ($OD_{600}$=0.6) by addition of IPTG. Cells were fed with GPP and OA during the induction phase and were allowed to grow overnight. The cell suspensions were then centrifuged and the supernatant was then injected into HPLC to confirm CBGA formation. FIG. 8 shows the HPLC chromatogram for the detection of CBGA produced in *E. coli* (using low copy plasmid, pBAD33). The concentration of produced CBGA was roughly calculated as 1.2 μg/ml from 5 mL culture.

THCA Synthase (THCAS)

Figure 9:
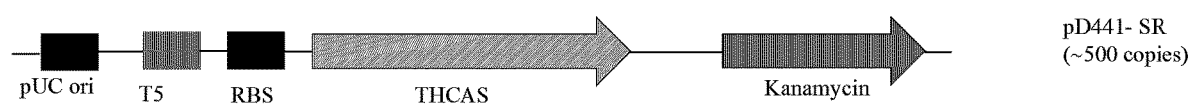
FIG. 9 is an illustration of an expression cassette for production of Δ(9)-Tetrahydrocannabinolic acid synthase (THCAS) in *E. coli*.

The THCA synthase gene was also cloned into a high copy, Kanamycin resistant, plasmid under the control of the strong IPTG inducible T5 promoter. The gene insertion was confirmed by PCR and gene sequencing. A schematic diagram of the resulting expression cassette for THCA synthase gene is shown in FIG. 9. The expression of THCA synthase was carried out by IPTG induction and cell lysate was analyzed by SDS page to confirm the expression. However, the THCA synthase was not expressed successfully into *E. coli*.

Figure 10:
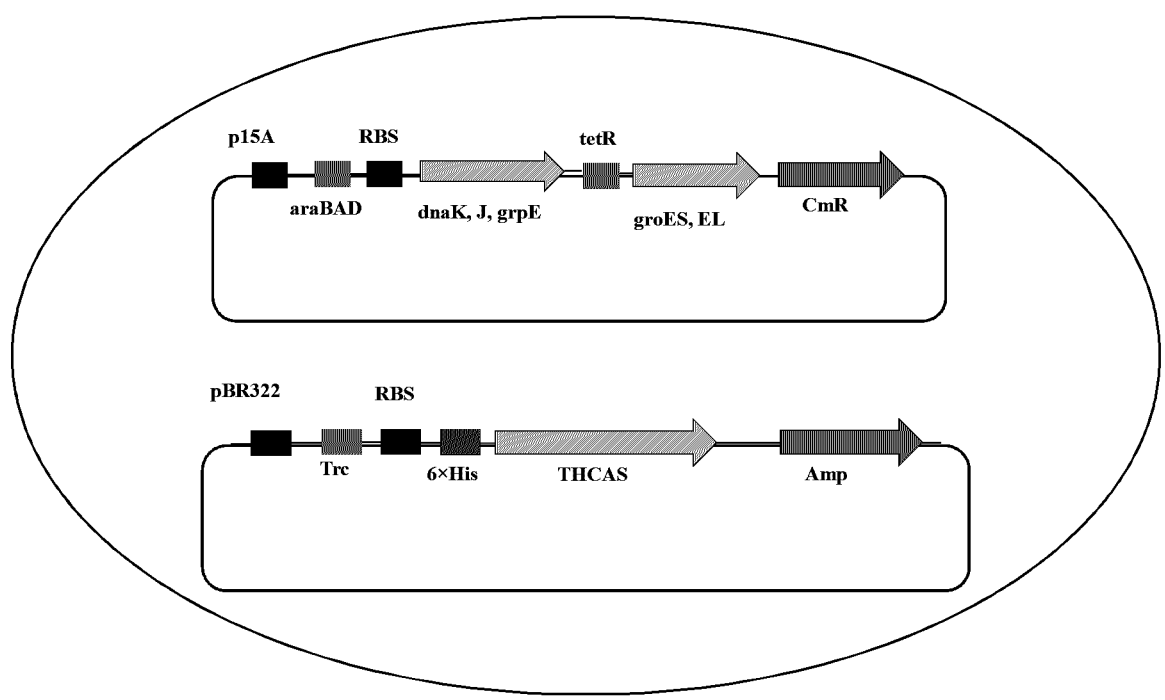
FIG. 10 is an illustration of an host cell containing a THCAS expression cassette and a chaperone co-expression cassette.

The THCA synthase gene encodes a flavinylated oxidase class of protein with eight glycosylation sites and a 28 amino acid signal peptide at the N terminal end. These limitations of *E. coli* for production of glycosylated transmembrane proteins makes it difficult to express the active form of THCA synthase class of proteins. To overcome this limitation a multi-factor strategy has been designed to express the gene without signal peptide to ensure the protein expression happens in cytosol, co-express the gene with modular chaperonins to assist the protein folding and increase production of active protein (e.g., FIG. 10), and co-expression with glycosylation machinery to assist the protein folding (e.g., FIG. 11). CBDA synthase (CBDAS) also falls into the same class of protein family so the same strategy will be applied to express the CBDA synthase as well. Similarly, CBCA synthase (CBCAS) is a glycosylated protein having a native signal sequence and therefore the same strategy will be applied to express the CBCA synthase as well. This part of study is under progress and following approaches are taken into consideration with regard to THCAS, and one of skill in the art will appreciate these approaches can also be applied to CBDAS and CBCAS.

Truncated THCAS

THCAS is truncated by removing 28 amino acids from the encoded N terminal end (84 bp from 5' end of the gene sequence).

Co-Expression with Chaperonin Plasmid

Figure 11:
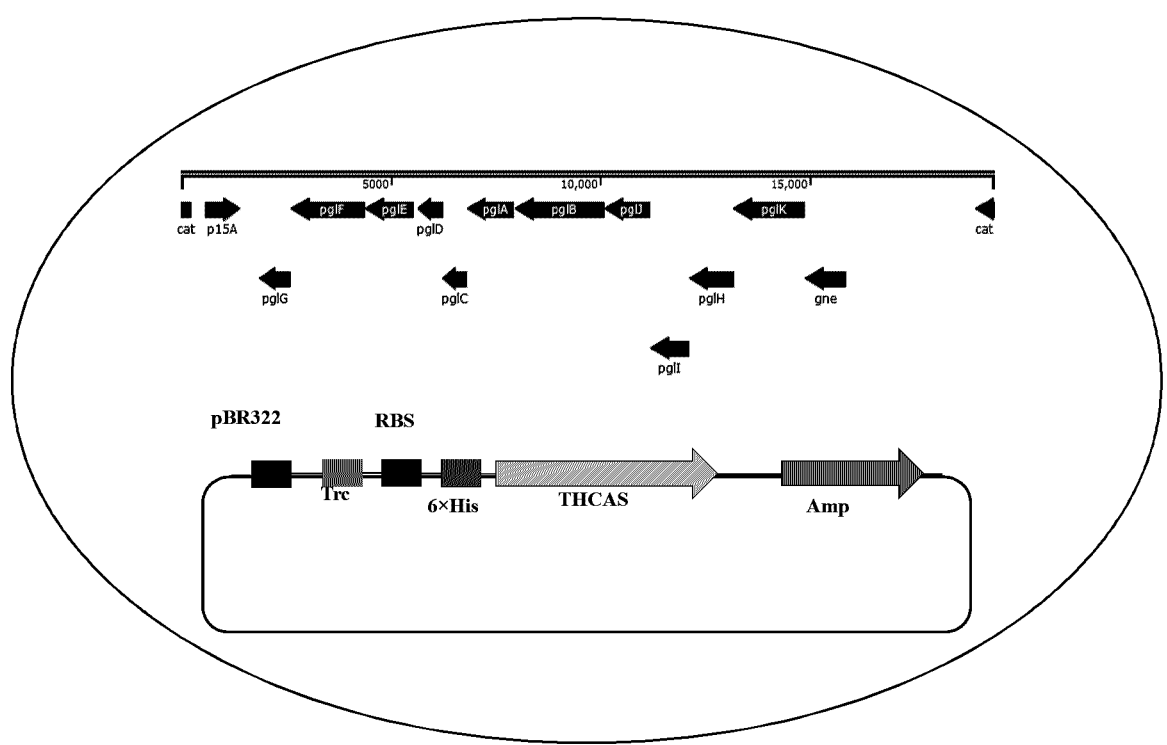
FIG. 11 is an illustration of an host cell containing a THCAS expression cassette and an expression cassette for a heterologous glycosylation system.

The THCA synthase gene was cloned onto a plasmid having ampicillin resistance, a pBR322 origin of replication, under the control of pTRC promoter to make sure that it has different and compatible origin of replication for co-expression with plasmids having the chaperonin system and the glycosylation system (FIG. 11). THCAS with and without signal peptide is co-expressed with the two major chaperone pathway components in E. coli, DnaK-DnaJ-GrpE and GroEl-GroES, which play distinct but cooperative roles in protein folding in E. coli. Though E. coli has its native chaperone system, high level production of recombinant protein can saturate endogenous chaperonin systems and can lead to unproductive aggregation. Under these conditions, an increase in the intracellular concentration of molecular chaperones that are limiting for folding can lessen inclusion body formation. Takahashi Yura group in Japan has constructed a pACYC184-based plasmid having the two chaperone pathways under different promoters. This plasmid (pG-KJE8), or a derivative thereof, is used to identify conditions for production of active THCA synthase in a host cell.

Co-Expression with Glycosylation System

Glycosylation may be required for increased expression, folding, processing, solubility, and/or activity THCA synthase in E. coli. Unfortunately, E. coli does not have a native protein glycosylation system. The N glycosylation system from *Campylobacter jejuni*, called pgl system, has been successfully expressed in E. coli. A plasmid with C. jejuni pgl system genes is provided. This plasmid, or a derivative thereof, is used to identify conditions for production of active THCA synthase in a host cell (FIG. 11).

Example 3

Optimization of the Expression of Cannabinoid Pathway Genes

To optimize the endogenous production of CBGA in E. coli, CBGA synthase is simultaneously co-expressed with the MEP pathway, GPP synthase, and or polyketide pathway components to provide the substrates GPP and OA, which are required for production of CBGA.

Co-expression candidates include:

Co-expression with MEP pathway to produce IPP and DMAPP

Co-expression with GPP synthase to supply GPP endogenously from IPP and DMAPP

Co-expression with the polyketide pathway to supply olivetolic acid (OA) endogenously.

Figure 12:
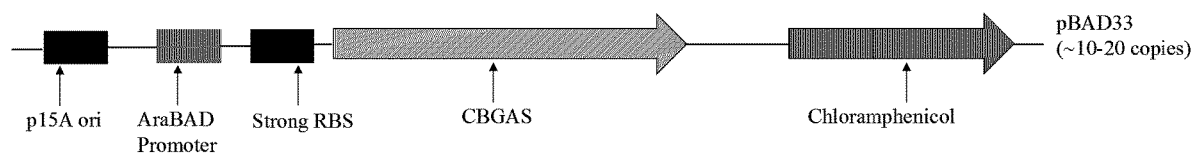
FIG. 12 is an illustration of a low copy-number CBGAS expression cassette.
Figure 13:
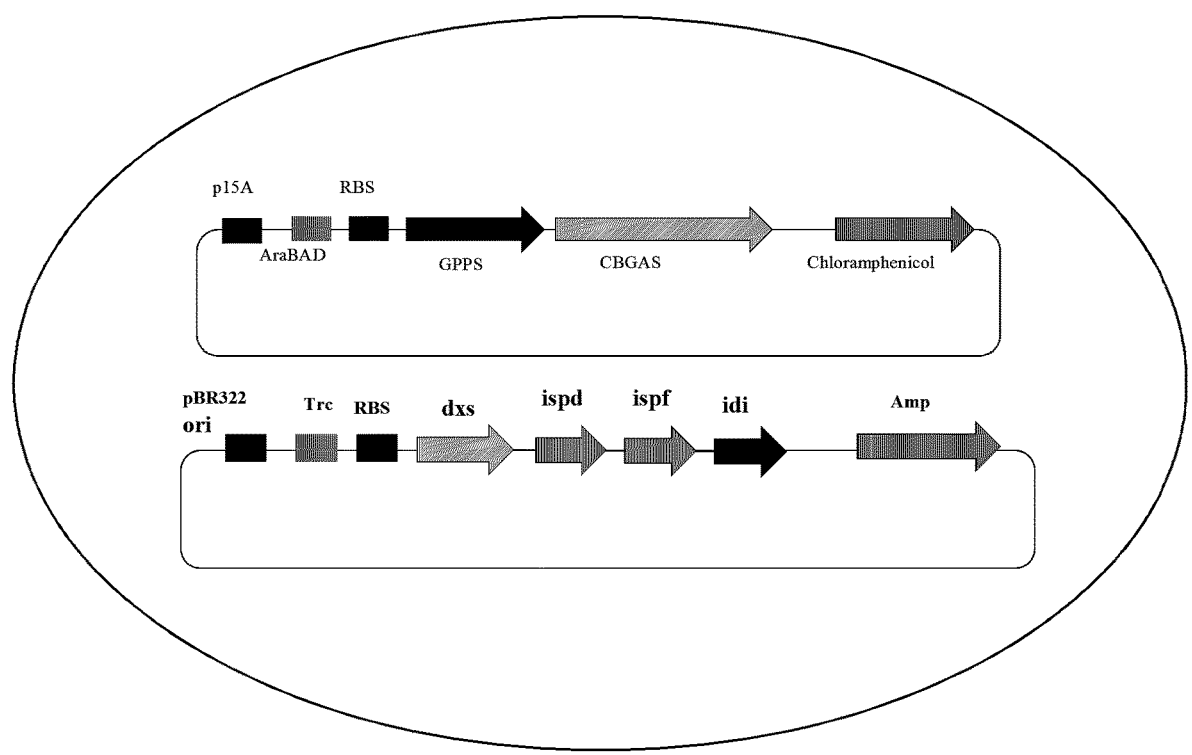
FIG. 13 is an illustration of a host cell containing a mevalonate-independent pathway expression cassette and a GPP synthase (GPPS) and CBGAS expression cassette.

For the co-expression of two different plasmids in E. coli, plasmids with low or medium copy number were used to reduce deleterious effect on cell growth, compatible origins of replication were used to ensure the maintenance of two or more plasmids, and independent antibiotic selection was used for stringent selection of each of the plasmids. Accordingly, CBGA synthase gene was cloned into low copy plasmid pBAD33. A schematic diagram of the low copy CBGA synthase expression plasmid is shown in (FIG. 12). The cloned CBGAS gene was verified by restriction digestion and sequencing. For co-expression of CBGAS with MEP pathway and GPP synthase, GPP synthase was cloned upstream to CBGAS in pBAD33 and then co-transformed with pTRC_RDE (FIG. 13). After co-transformation, the cells were grown with antibiotic selection and induced when the $OD_{600}$ reached 0.6. The amount of inducer concentrations are listed in FIG. 14.

Figure 15:
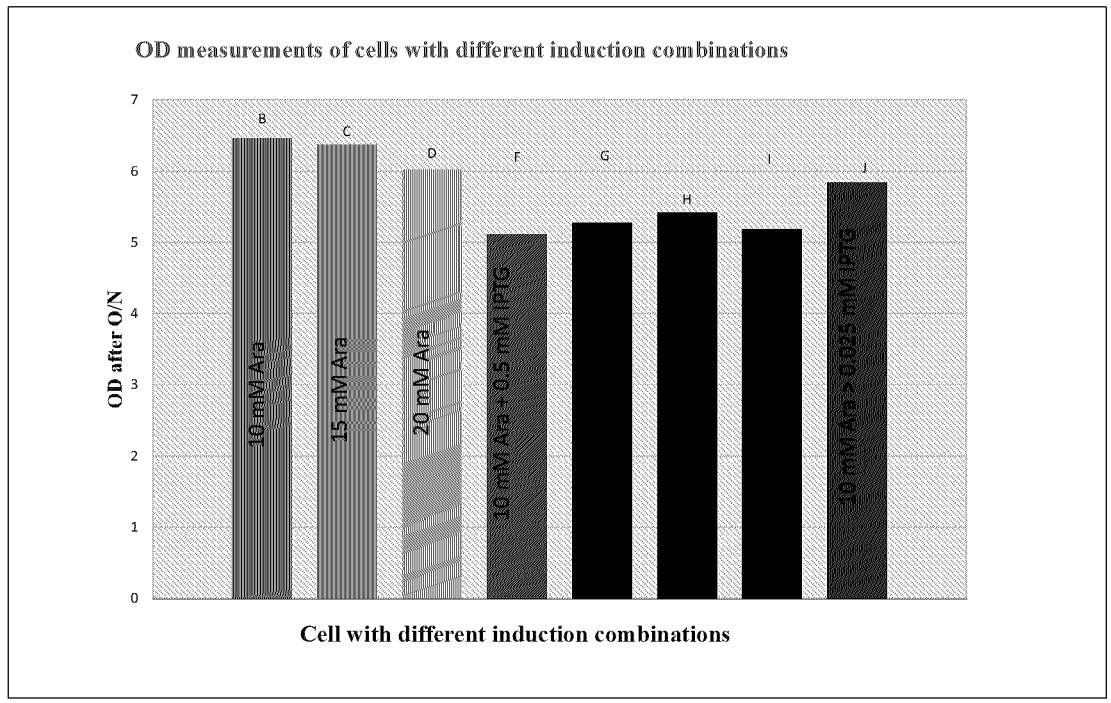
FIG. 15 illustrates OD measurements of *E. coli* under different inducer concentrations. Strains B-D contain a GPPS CBGAS expression cassette pBAD33_GPPS_CBGAS. Strains F-J contain both the pBAD33_GPPS_CBGAS expression cassette and MEP pathway expression cassette pTRC_RDE as illustrated in FIG. 13.
Figure 16:
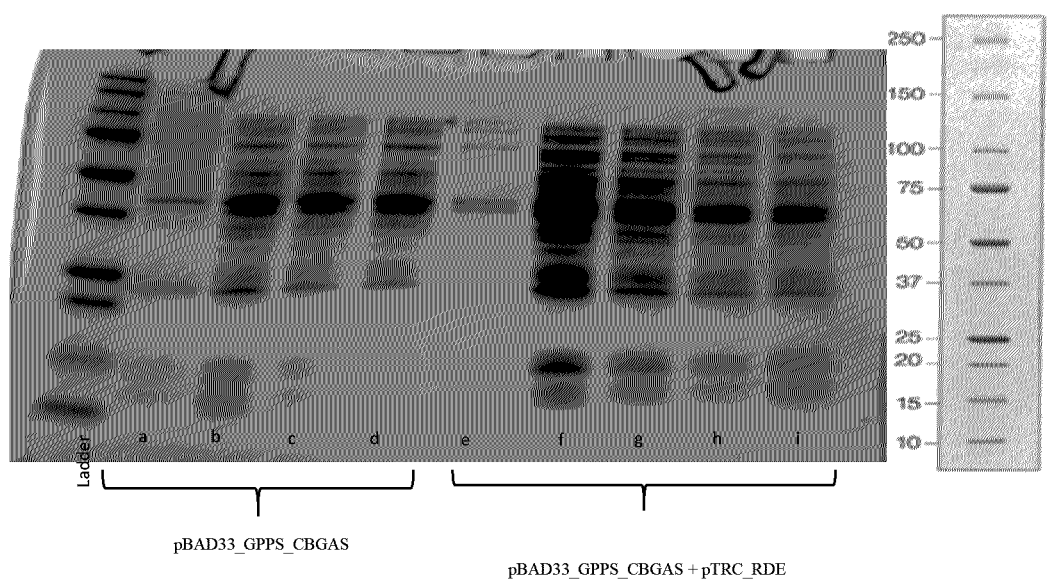
FIG. 16 shows results of an SDS PAGE analysis of cell lysates after expression of pBAD33_GPPS_CGGAS or co-expression of pBAD33_GPPS_CBGAS and pTRC_RDE.
Figure 17:
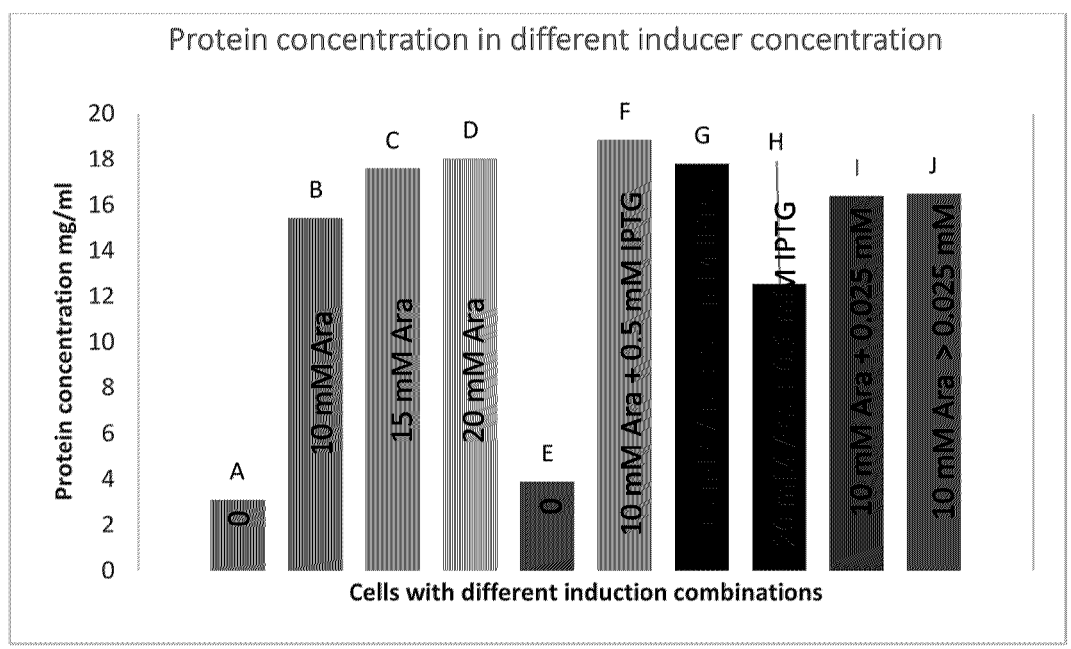
FIG. 17 illustrates the different protein concentrations in cell lysates from induced expression cultures with the indicated inducer concentrations. Strains A-D contain the plasmid pBAD33_GPPS_CBGAS. Strains E-J contain plasmids pBAD33_GPPS_CBGAS and pTRC_RDE.

After adding the inducer, the cells were allowed grow overnight. The $OD_{600}$ was measured to check the cell viability upon the protein production. The comparison of $OD_{600}$ for different cultures are shown in FIG. 15. Strains having pBAD33_GPPS_CBGAS were induced by arabinose at the concentrations of 10, 15 and 20 mM. Strains having pBAD33_GPPS_CBGAS and pTRC_RDE were induced with different concentration combinations of arabinose and IPTG. The proteins were extracted after cell lysis and the concentration of proteins was measured using Bradford method. The induction and expression of the proteins were checked by SDS PAGE (FIG. 16). Total extracted protein concentrations were plotted (FIG. 17) to compare with the expression data on SDS PAGE. The total protein concentration was found to be increased with the increase in inducer concentration and is inversely related to the cell population and growth.

Lee et al. have found the interference of IPTG on the induction of arabinose. So the expression of CBGAS was checked with the different combination of arabinose and IPTG concentrations. The total protein concentration was found to be higher when the cell was induced with 10 mM arabinose and 0.5 mM IPTG. Maintaining multiple plasmids increases the metabolic burden on the cell from DNA, RNA, and protein synthesis as well as the total number of antibiotic resistance proteins the cell must produce, and leads to low production of the desired final product. Also maintaining the balance between different inducers will also give the non-reproducible production level for the final product. To overcome this limitation, the entire gene cassette is constructed on a single plasmid having the MEP pathway and GPPS and CBGAS operon together. Additionally or alternatively, the MEP pathway, GPPS, and/or CBGAS are integrated into the host cell genome.

Example 4

Metagenomic Screening and Cloning of Bifunctional ispDF Gene on MEP Pathway

Environmental metagenomes from soil bacteria were screened to identify alternative MEP pathway genes. A novel bifunctional enzyme in the non-mevalonate pathway that is considerably more active than the corresponding E. coli orthologs was identified. The new bifunctional enzyme co-localized the active sites of IspD and IspF onto a single polypeptide scaffold. Activity of bifunctional gene was assessed for lycopene production as a proxy for cannabinoid synthesis. The gene was called as ispDF and cloned in pTrc-RDE operon replacing ispD and ispF with ispDF using same strong RBS. This engineered plasmid was named as pTrc-RDE* and transformed in E. coli (DE3). Two additional metagenomics bifunctional enzymes that co-localized the active sites of ispD and ispF, and were termed ispDF2, and ispDF3, respectively.

Protein Expression Studies

Figure 18:
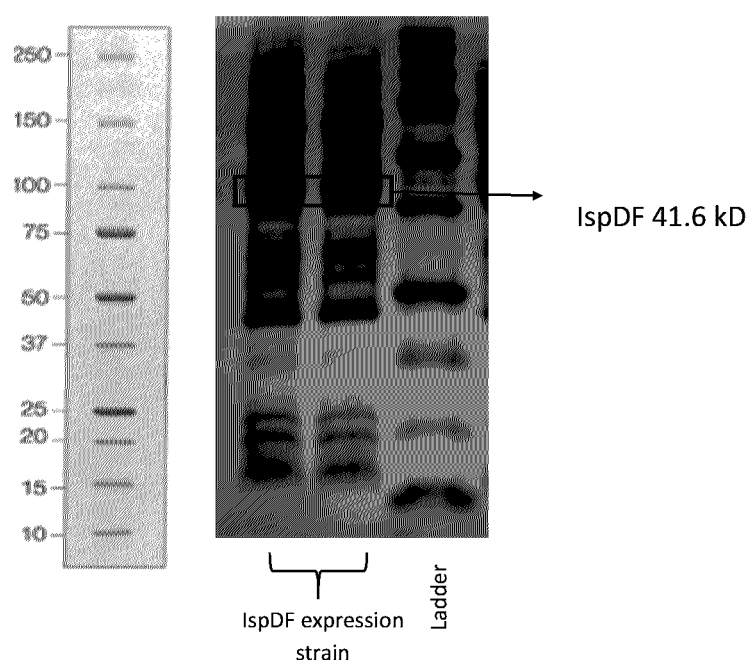
FIG. 18 shows results of an SDS PAGE analysis of cell lysates after expression of ispDF in a strain containing a pTRC_RDE* expression construct.

Strains harboring plasmids pTrc-RDE and pTrc-RDE* were tested for protein expression by induction with IPTG. Cells were grown in LB broth at 37° C. to reach $OD_{600}$ of 0.6, induced by addition of IPTG into the culture medium, and then the cultures were incubated overnight at 30° C. Cells harvested from the culture were lysed and total proteins were extracted. Concentration of total protein was estimated with Bradford method and run on SDS-PAGE gel. The gels were stained with Coomassie Brilliant Blue G-250 dye for visualization. Both pTrc-RDE and pTrc-RDE* plasmids upon expression showed bands corresponding to pathway enzymes on SDS-PAGE. ispDF expression was shown by SDS-PAGE analysis of induced cell lysates (FIG. 18).

Modelling ispDF: Bifunctional ispDF from Campylobacter jejuni has been reported as CJ-ispDF. IspDF reported in our study (ispDF1) is modelled with CJ-ispDF using Swiss Model. It bears around 31% sequence similarity. Its alignment with CJ-ispDF and, native ispD and ispF shows dissimilar amino acids (FIG. 19). This suggests that ispDF is novel and hasn't been reported. More analysis about active site co-localization is being carried out.

Functional Analysis of Platform Strain:

Engineered *E. coli* strains were transformed with plasmids containing downstream genes for conversion of a C5 isoprenoid precursor to lycopene. Lycopene biosynthetic genes were cloned under the control of a constitutive promoter. Lycopene expressing plasmids were low copy and had compatibility of origin of replication for co-expression.

Figure 20:
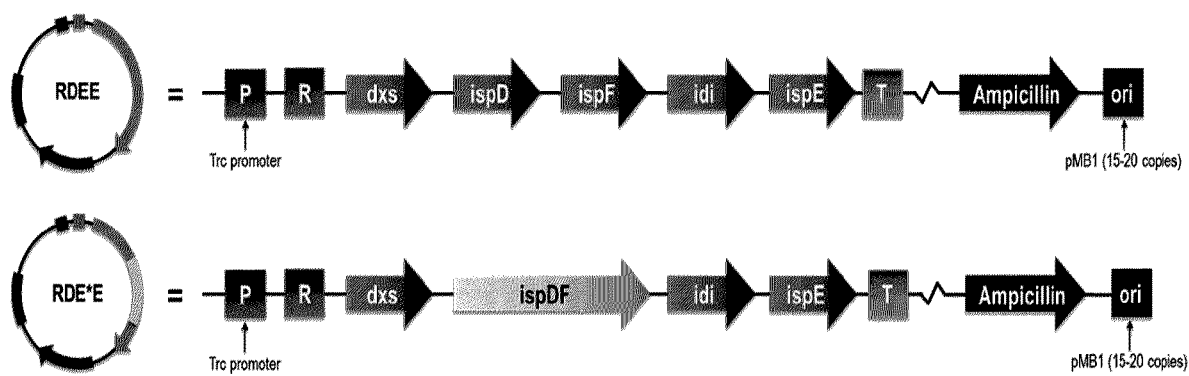
FIG. 20 illustrates pTRC_RDEE and pTRC_RDE*E expression constructs. pTRC_RDE*E contains the bifunctional ispDF enzyme in place of the ispD and ispF enzymes.

It is reported that ispD, ispF and ispE enzymes form a multi-component complex to channel metabolite through three consecutive catalytic steps. To study this further, we cloned native ispE gene amplified from genome in both the operons. The variant plasmids were named as pTrc-RDEE and pTrc-RDE*E respectively of pTrc-RDE and pTrc-RDE* (FIG. 20). Both these variants were also tested functionally for lycopene production as described below.

Example 5

Figure 21:
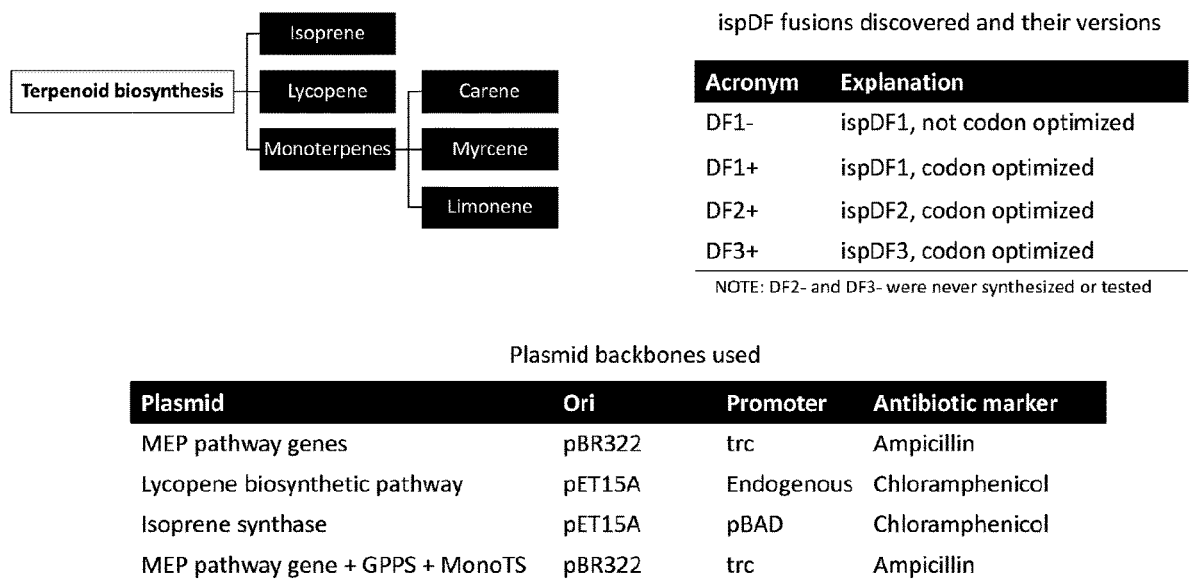
FIG. 21 illustrates an overview of constructs and strains tested for increased flux through the MEP pathway.

Increasing Terpenoid Biosynthesis Via Heterologous Expression of One or More Components of an MEP Pathway Different constructs were produced tested for the ability to support increased terpenoid biosynthesis (FIG. 21).

Isoprene Synthesis

Figure 22:
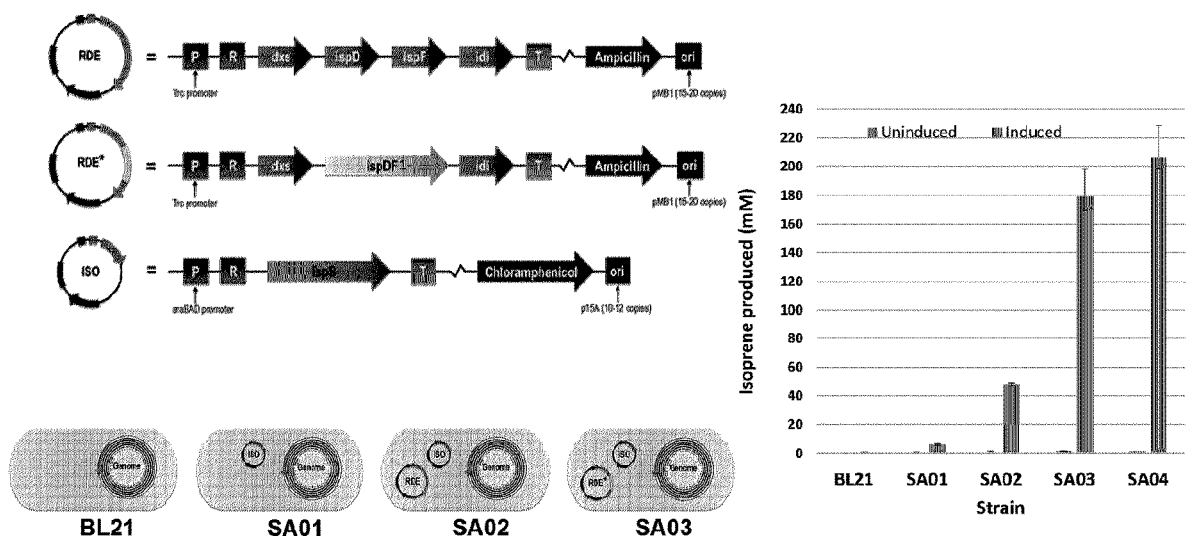
FIG. 22 illustrates constructs and data for isoprene production. Construct SA04 is identical to construct SA03, except that the nucleic acid encoding ispDF is codon optimized.

The following strains of *E. coli* were provided: parent control strain (BL21); control strain SA01 containing an expression cassette encoding isoprene synthase (ispS) operably linked to an arabinose promoter; strain SA02 containing the expression cassette in SA01 and an RDE expression cassette encoding dxs, ispD, ispF, and idi operably linked to a Trc promoter; and strain SA03 containing the expression cassette in SA01 and an RDE* expression cassette encoding dxs, ispDF1, and idi operably linked to a Trc promoter (FIG. 22, left). In SA03, the designation ispDF1-indicates that the nucleic acid encoding ispDF1 is not codon optimized for increased expression in the heterologous host cell, whereas ispDF+ (not shown in FIG. 22) indicates that the nucleic acid encoding the enzyme is codon optimized Cultures were grown in sealed glass culture tubes at 30° C. at 230 rpm. Cultures were induced after reaching OD600 0.6 and incubated further for 20 h. 0.05 mM IPTG and 10 mM arabinose were used as inducers. Culture head space was analyzed by GC-MS. Samples were heated to 70° C. before injection. Isoprene was quantified using a calibration curve. Isoprene production by the strains described herein is illustrated in FIG. 22, right.

Lycopene Synthesis

Plasmid pAC-LYC (Addgene plasmid #53270) was obtained. This plasmid contains an expression cassette having a constitutive promoter operably linked to lycopene synthesis genes crtE, crtI, and crtB. See, Cunningham F X Jr, et al., Plant Cell. 1994 August; 6(8):1107-21. The following strains of *E. coli* were provided: parent control strain (BL21(DE3)); strain RDE containing plasmid pAC-LYC and a plasmid containing the RDE expression cassette described above; strain RDE*(DF1-) containing plasmid pAC-LYC and a plasmid containing the RDE* expression cassette described above; strain RDE*(DF1+) containing plasmid pAC-LYC and a plasmid containing the RDE* expression cassette having a nucleic acid encoding codon optimized ispDF1; strain RDE*(DF2+) containing plasmid pAC-LYC and a plasmid containing the RDE* expression cassette having a nucleic acid encoding codon optimized ispDF2; and strain RDE*(DF3+) containing plasmid pAC-LYC and a plasmid containing the RDE* expression cassette having a nucleic acid encoding codon optimized ispDF3. Additional strains generated include SA01, containing pAC-LYC; SA02, containing pAC-LYC and pTrc-RDE; SA03 containing pAC-LYC and pTrc-RDEE; SA04 containing pAC-LYC and pTrc-RDE*; and SA05 containing pAC-LYC and pTrc-RDE*E. The sequences of ispDF1, ispDF2, and ispDF3 are shown in FIG. 26.

Figure 23:
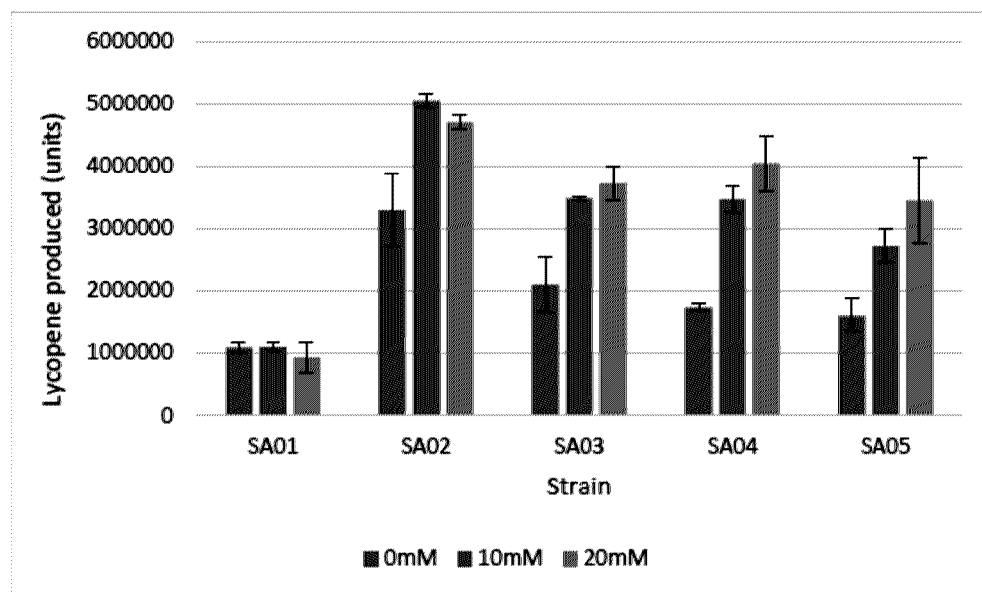
FIG. 23 illustrates lycopene production in four different strains of *E. coli*. SA01: pAC-LYC; SA02: pAC-LYC and pTRC-RDE; SA03: pAC-LYC and pTRC-RDEE; SA04: pAC-LYC and pTRC-RDE*; and SA05: pAC-LYC and pTRC-RDE*E.

For lycopene production, seed cultures of SA01-SA05 were grown in LB media at 30° C. overnight. These cultures were then diluted to optical density of 0.2 with fresh media and induced with IPTG. The production cultures were incubated at 30° C. for 20 h in dark shaking at 250 rpm. Lycopene extraction was performed by extracting 4 mL of culture with 2 mL of acetone. The acetone extract was analyzed on HPLC. HPLC method: column—C18, mobile phase—methanol:tetrahydrofuran:water (66:30:4), flow rate—1 mL/min, detection at 472 nm wavelength using photodiode array detector and lycopene peak was confirmed with in-house lycopene standard. FIG. 23 shows that IPTG induction increases lycopene production. Optimal induction levels are different for different strain.

Figure 24:
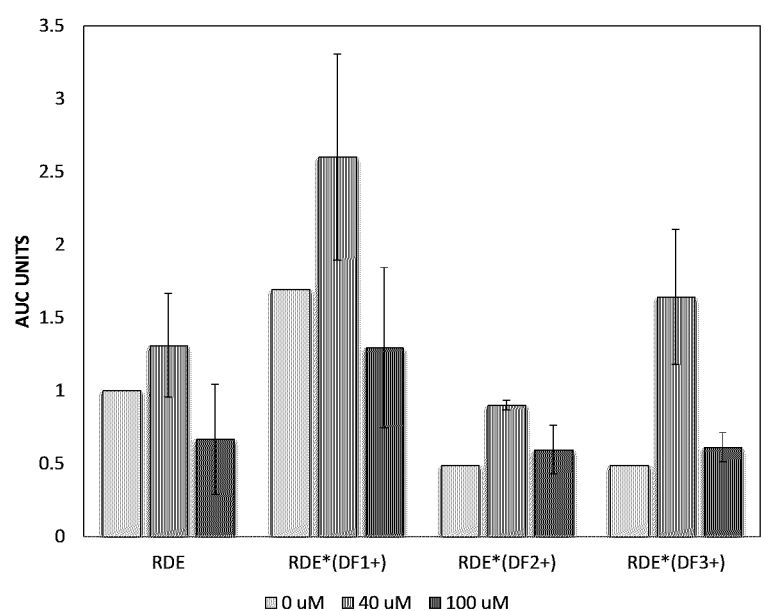
FIG. 24 illustrates production of lycopene.

In a second experiment, cultures were grown in LB overnight at 30° C. These cultures were then diluted to OD600 of 0.2 with LB. They were induced with IPTG and were allowed to grow at 30° C. for 24 h. 2 mL of culture were centrifuged at 8000 rpm for 5 min to produce a cell pellet. Lycopene from the cell pellet was extracted with 1 mL acetone at 55° C. for 15 min. The mixtures were then centrifuged at 14000 rpm. The resulting the supernatant was analyzed on a C-18 column by HPLC using an isocratic elution method with a mixture of methanol, tetrahydrofuran and water (66:30:4) at a flow rate of 1 mL/min. Lycopene yield was measured as area under the HPLC curve for lycopene peak. The peak was verified with in house standard. The area was normalized with respect to RDE strain with 0 µM IPTG. The results are shown in FIG. 24.

Monoterpene Synthesis

Figure 25:
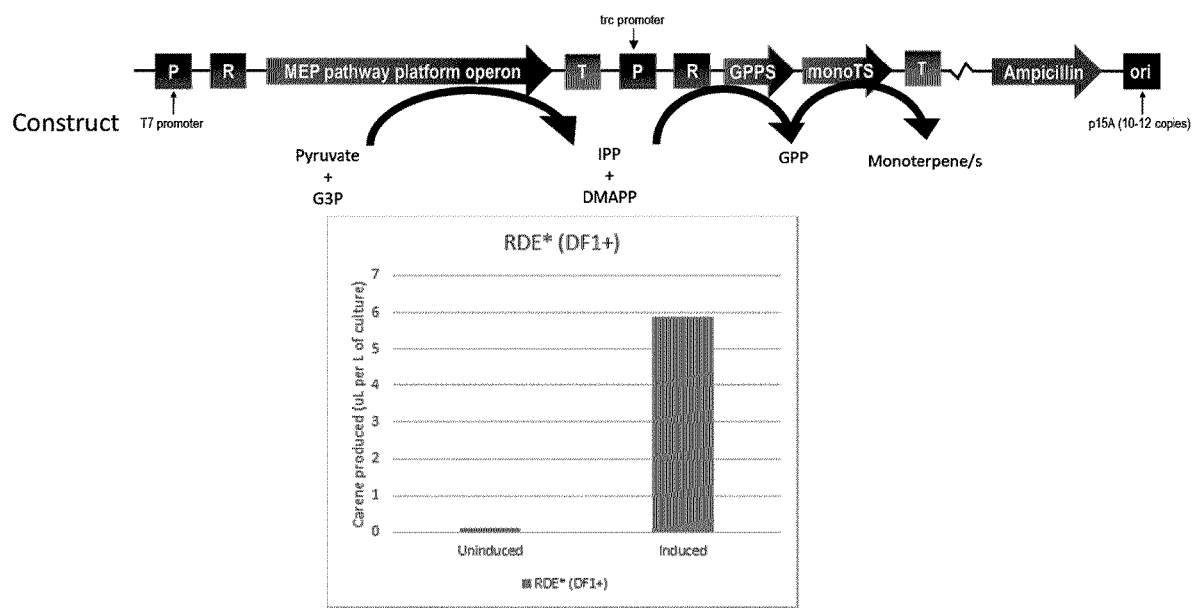
FIG. 25 illustrates constructs and data for production of the monoterpene carene.

FIG. 25, top illustrates a construct for producing a monoterpene in a host cell. The construct includes an MEP pathway platform operon encoding dxs, codon optimized ispDF1 (DF1+), and idi, operably linked to a T7 promoter; and a monoterpene operon encoding GPP synthase and a monoterpene synthase operably linked to a Trc promoter. In this experiment, the monoterpene synthase was carene synthase.

Cultures are grown in LB+0.5% yeast extract overnight at 30° C. These cultures were then diluted to OD600 of 0.2 with the media supplemented with 2 mM magnesium chloride, incubated at 37° C., and then induced with IPTG at OD600 of 0.8. Cultures were overlaid with 10% dodecane. Monoterpene concentration was analyzed on GC-MS using standard curve. The results are illustrated in FIG. 25, bottom. Successful production of monoterpenes limonene and myrcene was also achieved using a limonene synthase, and a myrcene synthase respectively. IspDF2+; ispDF3+; and dxs, ispD, ispF, and idi were also able to support increased production of monoterpenes.

Exemplary Sequences

Exemplary sequences referred to in this application include, but are not limited to those listed in the following table:

| GeneBank Accession/*Cannabis* Transcriptome ID/other ID | Full Name of the Gene/Enzyme | Abbreviation |
|---|---|---|
| AB057805.1 | Tetrahydrocannabinolic Acid Synthase | THCAS |
| AB292682.1 | Cannabidiolic Acid Synthase - with transit peptide | CBDAS |
| IM00002.1 | Cannabidiolic Acid Synthase II - without transit peptide | CBDAS II |
| PK28436.1 | Aromatic Prenyltransferase/geranylpyrophosphate olivetolate geranyltransferase | PT |
| JN679224.1 | Olivetolic Acid Cyclase | OAC |
| AB164375.1 | Olivetol Synthase | OLS |
| JN717233.1 \| PK04797.1 | Acyl-Activating Enzyme 1 | AAE1 |
| JN717235.1 \| PK13710.1 | Acyl-Activating Enzyme 3 | AAE3 |
| PK04410.1 | Hydroperoxide Lyase | HPL |
| PK08276.1 | Lipoxygenase | LOX1 |
| IM00001.1 | Desaturase | DS |
| AAO73863 | Carene synthase | MonoTS |
| EFF14228 | 1-deoxy-D-xylulose-5-phosphate synthase | Dxs |
| WP_072972099 | 2-C-methyl-D-erythritol 4-phosphate cytidylyltransferase | IspD/MCT |
| WP_086589482 | 2-C-methyl-D-erythritol 2,4-cyclodiphosphate synthase | IspF/MDS |
| WP_115903881 | isopentenyl-diphosphate Delta-isomerase | Idi |
| AF513112.1 | geranyl diphosphate synthase | GPPS |
| WP_053287215 | geranyl transferase | IspA |
| NP_414715 | 1-deoxy-D-xylulose 5-phosphate reductoisomerase | IspC/DXR |
| EGT67781 | 4-diphosphocytidyl-2-C-methylerythritol kinase | IspE/CMK |
| ANK02812 | 4-hydroxy-3-methylbut-2-en-1-yl diphosphate synthase | IspG/HDS |
| AAL38655 | 4-hydroxy-3-methylbut-2-enyl diphosphate reductase | IspH/HDR |
| AAA24819.1 | phytoene synthase | CrtE |
| AAA24820.1 | phytoene dehydrogenase | CrtI |
| AAA24821 | prephytoene pyrophosphate synthase | CrtB |
| Q50L36 | Isoprene synthase | IspS |

Some of genes come from GenBank database, while others are from *Cannabis* genome browser (genome.ccbr.utoronto.ca/cgi-bin/hgGateway_). IM00001.1 is a sequence ID referring to the desaturase that is generated from the public sequences of *Cannabis* mRNAs and ESTs.

Exemplary sequences are provided below.

```
>AB057805.1| Cannabis sativa mRNA for tetrahydrocannabinolic acid
synthase (THCAS), complete cds
                                                        (SEQ ID NO: 4)
ATGAATTGCTCAGCATTTTCCTTTTGGTTTGTTTGCAAAATAAT

ATTTTTCTTTCTCTCATTCCATATCCAAATTTCAATAGCTAATCCTCGAGAAAACTTCCTTAAATGCTTC

TCAAAACATATTCCCAACAATGTAGCAAATCCAAAACTCGTATACACTCAACACGACCAATTGTATATGT

CTATCCTGAATTCGACAATACAAAATCTTAGATTCATCTCTGATACAACCCCAAAACCACTCGTTATTGT

CACTCCTTCAAATAACTCCCATATCCAAGCAACTATTTTATGCTTAAGAAAGTTGGCTTGCAGATTCGA

ACTCGAAGCGGTGGCCATGATGCTGAGGGTATGTCCTACATATCTCAAGTCCCATTTGTTGTAGTAGACT

TGAGAAACATGCATTCGATCAAAATAGATGTTCATAGCCAAACTGCGTGGGTTGAAGCCGGAGCTACCCT

TGGAGAAGTTTATTATTGGATCAATGAGAAGAATGAGAATCTTAGTTTTCCTGGTGGGTATTGCCCTACT

GTTGGCGTAGGTGGACACTTTAGTGGAGGAGGCTATGGAGCATTGATGCGAAATTATGGCCTTGCGGCTG

ATAATATTATTGATGCACACTTAGTCAATGTTGATGGAAAAGTTCTAGATCGAAAATCCATGGGAGAAGA

TCTGTTTTGGGCTATACGTGGTGGTGGAGGAGAAAACTTTGGAATCATTGCAGCATGGAAAATCAAACTG

GTTGCTGTCCCATCAAAGTCTACTATATTCAGTGTTAAAAAGAACATGGAGATACATGGCTTGTCAAGT

TATTTAACAAATGGCAAATATTGCTTACAAGTATGACAAAGATTTAGTACTCATGACTCACTTCATAAC

AAAGAATATTACAGATAATCATGGGAAGAATAAGACTACAGTACATGGTTACTTCTCTTCAATTTTTCAT

GGTGGAGTGGATAGTCTAGTCGACTTGATGAACAAGAGCTTTCCTGAGTTGGGTATTAAAAAAACTGATT

GCAAAGAATTTAGCTGGATTGATACAACCATCTTCTACAGTGGTGTTGTAAATTTTAACACTGCTAATTT

TAAAAAGGAAATTTTGCTTGATAGATCAGCTGGGAAGAAGACGGCTTTCTCAATTAAGTTAGACTATGTT

AAGAAACCAATTCCAGAAACTGCAATGGTCAAAATTTTGGAAAAATTATATGAAGAAGATGTAGGAGCTG

GGATGTATGTGTTGTACCCTTACGGTGGTATAATGGAGGAGATTTCAGAATCAGCAATTCCATTCCCTCA

TCGAGCTGGAATAATGTATGAACTTTGGTACACTGCTTCCTGGGAGAAGCAAGAAGATAATGAAAAGCAT
```

-continued

ATAAACTGGGTTCGAAGTGTTTATAATTTTACGACTCCTTATGTGTCCCAAAATCCAAGATTGGCGTATC

TCAATTATAGGGACCTTGATTTAGGAAAAACTAATCATGCGAGTCCTAATAATTACACACAAGCACGTAT

TTGGGGTGAAAAGTATTTTGGTAAAAATTTTAACAGGTTAGTTAAGGTGAAAACTAAAGTTGATCCCAAT

AATTTTTTTAGAAACGAACAAAGTATCCCACCTCTTCCACCGCATCATCATTAA

> AB292682.1| *Cannabis sativa* CBDAS mRNA for cannabidiolic acid synthase (CBDAS), with transit peptide (SEQ ID NO: 5)

ATGAAGTGCTCAACATTCTCCTTTTGGTTTGTTTGCAAGATAATATTTTCTTTTTCTCATTCAATATCC

AAACTTCCATTGCTAATCCTCGAGAAAACTTCCTTAAATGCTTCTCGCAATATATTCCCAATAATGCAAC

AAATCTAAAACTCGTATACACTCAAAACAACCCATTGTATATGTCTCTCCTAAATTCGACAATACACAAT

CTTAGATTCACCTCTGACACAACCCCAAAACCACTTGTTATCGTCACTCCTTCACATGTCTCTCATATCC

AAGGCACTATTCTATGCTCCAAGAAAGTTGGCTTGCAGATTCGAACTCGAAGTGGTGGTCATGATTCTGA

GGGCATGTCCTACATATCTCAAGTCCCATTTGTTATAGTAGACTTGAGAAACATGCGTTCAATCAAAATA

GATGTTCATAGCCAAACTGCATGGGTTGAAGCCGGAGCTACCCTTGGAGAAGTTTATTATTGGGTTAATG

AGAAAAATGAGAATCTTAGTTTGGCGGCTGGGTATTGCCCTACTGTTTGCGCAGGTGGACACTTTGGTGG

AGGAGGCTATGGACCATTGATGAGAAACTATGGCCTCGCGGCTGATAATATCATTGATGCACACTTAGTC

AACGTTCATGGAAAAGTGCTAGATCGAAAATCTATGGGGAAGATCTCTTTTGGGCTTTACGTGGTGGTG

GAGCAGAAAGCTTCGGAATCATTGTAGCATGGAAAATTAGACTGGTTGCTGTCCCALAGTCTACTATGTT

TAGTGTTAAAAAGATCATGSAGATACATCAGCTTGTCAAGTTACTTAACAAATGGCAAAATATTGCTTAC

AAGTATGACAAAGATTTATTACTCATGACTCACTTCATAACTAGGAACATTACAGATAATCAAGGGAAGA

ATAAGACAGCAATACACACTTACTTCTCTTCAGTTTTCCTTGGTGGAGTGGATAGTCTAGTCGACTTGAT

GAACAAGAGTTTTCCTGAGTTGGGTATTAAAAAAACGGATTGCAGACAATTGAGCTGGATTGATACTATC

ATCTTCTATAGTGGTGTTGTAAATTACGACACTGATAATTTTAACAAGGAAATTTTGCTTGATAGATCCG

CTGGGCAGAACGGTGCTTTCAAGATTAAGTTAGACTACGTTAAGAAACCAATTCCAGAATCTGTATTTGT

CCAAATTTTGGAAPAATTATATGAAGAAGATATAGGAGCTGGGATGTATGCGTTGTACCCTTACGGTGGT

ATAATGGATGAGATTTCAGAATCAGCAATTCCATTCCCTCATCGAGCTGGAATCTTGTATGAGTTATGGT

ACATATGTAGTTGGGAGAAGCAAGAAGATAACGAAAAGCATCTAAACTGGATTAGAAATATTTATAACTT

CATGACTCCTTATGTGTCCAAAAATCCAAGATTGGCATATCTCAATTATAGAGACCTTGATATAGGAATA

AATGATCCCAAGAATCCAAATAATTACACACAAGCACGTATTTGGGGTGAGAAGTATTTTGGTAAAAATT

TTGACAGGCTAGTAAAAGTGAAAACCCTGGTTGATCCCAATAACTTTTTTAGAAACGAACAAAGCATCCC

ACCTCTTCCACGGCATCGTCATTAA

>IM0002.1| *Cannabis sativa* CBDAS mRNA for cannabidiolic acid synthase II (CBDASII), without transit peptide (SEQ ID NO: 6)

ATGAATCCTCGAGAAAACTTCCTTAAATGCTTCTCGCAATATATTCCCAATAATGCAACAAATCTAAAAC

TCGTATACACTCAAAACAACCCATTGTATATGTCTGTCCTAAATTCGACAATACACAATCTTAGATTCAC

CTCTGACACAACCCCAAAACCACTTGTTATCGTCACTCCTTCACATGTCTCTCATATCCAAGGCACTATT

CTATGCTCCAAGAAAGTTGGCTTGCAGATTCGAACTCGAAGTGGTGGTCATGATTCTGAGGGCATGTCCT

ACATATCTCAAGTCCCATTTGTTATAGTAGACTTGAGAAACATGCGTTCAATCAAAATAGATGTTCATAG

CCAAACTGCATGGGTTGAAGCCGGAGCTACCCTTGGAGAAGTTTATTATTGGGTTAATGAGALAAATGAG

AATCTTAGTTTGGCGCCTGGGTATTGCCCTACTGITTGCGCAGGTGGACACTTTGGTGGAGGAGGCTATG

GACCATTGATGAGAAACTATGGCCTCGCGGCTGATAATATCATTGATGCACACTTAGTCAACGTTCATGG

AAAAGTGCTAGATCGAAAATCTATGGGGAAGATCTCTTTTGGGCTTTACGTGGTGGTGGAGCAGAAAGC

-continued

```
TTCGGAATCATTGTAGCATGGAAAATTAGACTGGTTGCTGTCCCAAAGTCTACTATGTTTAGTGTTAAAA

AGATCATGGAGATACATGAGCTTGTCAAGTTAGTTAACAAATGGCAAAATATTGCTTACAAGTATGACAA

AGATTTATTACTCATGACTCACTTCATAACTAGGAACATTACAGATAATCAAGGGAAGAATAAGACAGCA

ATACACACTTACTTCTCTTCAGTTTTCCTTGGTGGAGTGGATAGTCTAGTCGACTTGATGAACAAGAGTT

TTCCTGAGTTGGGTATTAAAAAAACGGATTGCAGACAATTGAGCTGGATTGATACTATCATCTTCTATAG

TGGTGTTGTAAATTACGACACTGATAATTTTAACAAGGAAATTTTGCTTGATAGATCCGCTGGGCAGAAC

GGTGCTTTCAAGATTAAGTTAGACTACGTTAAGAAACCAATTCCAGAATCTGTATTTGTCCAAATTTTGG

AAAAATTATATGAAGAAGATATAGGAGCTGGGATGTATGCGTTGTACCCTTACGGTGGTATAATGGATGA

GATTTCAGAATCAGCAATTCCATTCCCTCATCGAGCTGGAATCTTGTATGAGTTATGGTACATATGTAGT

TGGGAGAAGCAAGAAGATAACGAAAAGCATCTAAACTGGATTAGAAATATTTATAACTTCATGACTCCTT

ATGTGTCCAAAAATCCAAGATTGGCATATCTCAATTATAGAGACCTTGATATAGGAATAAATGATCCCAA

GAATCCAATAATTACACACAAGCACGTATTTGGGGTGAGAAGTATTTTGGTAAAAATTTTGACAGGCTA

GTAAAAGTGAAAACCCTGGTTGATCCCAATAACTTTTTTAGAAACGAACAAAGCATCCCACCTCTTCCAC

GGCATCGTCATTAA
```

> PK28436.1 | Aromatic Prenyltransferase (PT) or geranylpyrophosphate olivetolate geranyltransferase (SEQ ID NO: 7)
```
ATGGGACTCTCATCAGTTTGTACCTTTTCATTTCAAACTAATTACCATACTTTATTAAATCCTCACAATA

ATAATCCCAAAACCTCATTATTATGTTATCGACACCCCAAAACACCAATTAAATACTCTTACAATAATTT

TCCCTCTAAACATTGCTCCACCAAGAGTTTTCATCTACAAAACAAATGCTCAGAATCATTATCAATCGCA

AAAAATTCCATTAGGGCAGCTACTACAAATCAAACTGAGCCTCCAGAATCTGATAATCATTCAGTAGCAA

CTAAAATTTTAAACTTTGGGAAGGCATGTTGGAAACTTCAAAGACCATATACAATCATAGCATTTACTTC

ATGCGCTTGTGGATTGTTTGGGAAAGAGTTGTTGCATAACACAAATTTAATAAGTTGGTCTCTGATGTTC

AAGGCATTCTTTTTTTTGGTGGCTATATTATGCATTGCTTCTTTTACAACTACCATCAATCAGATTTACG

ATCTTCACATTGACAGAATAAACAAGCCTGATCTACCACTAGCTTCAGGGGAAATATCAGTAAACACAGC

TTGGATTATGAGCATAATTGTGGCACTGTTTGGATTGATAATAACTATAAAAATGAAGGGTGGACCACTC

TATATATTTGGCTACTGTTTTGGTATTTTTGGTGGGATTGTCTATTCTGTTCCACCATTTAGATGGAAGC

AAAATCCTTCCACTGCATTTCTTCTCAATTTCCTGGCCCATATTATTACAAATTTCACATTTTATTATGC

CAGCAGAGCAGCTCTTGGCCTACCATTTGAGTTGAGGCCTTCTTTTACTTTCCTGCTAGCATTTATGAAA

TCAATGGGTTCAGCTTTGGCTTTAATCAAAGATGCTTCAGACGTTGAAGGCGACACTAAATTTGGCATAT

CAACCTTGGCAAGTAAATATGGTTCCAGAAACTTGACATTATTTTGTTCTGGAATTGTTCTCCTATCCTA

TGTGGCTGCTATACTTGCTGGGATTATCTGGCCCCAGGCTTTCAACAGTAACGTAATGTTACTTTCTCAT

GCAATCTTAGCATTTTGGTTAATCCTCCAGACTCGAGATTTTGCGTTAACAAATTACGACCCGGAAGGAG

GCAGAAGATTTACGAGTTCATGTGGAAGCTTTATTATGCTGAATATTTAGTATATGTTTTCATATAA
```

> JN679224.1| Cannabis sativa olivetolic acid cyclase (OAC) mRNA, complete cds (SEQ ID NO: 8)
```
ATGGCAGTGAAGCATTTGATTGTATTGAAGTTCAAAGATGAAATCACAGAAGCCCAAAAGGAAGAATTTT

TCAAGACGTATGTGAATCTTGTGAATATCATCCCAGCCATGAAAGATGTATACTGGGGTAAAGATGTGAC

TCAAAAGAATAAGGAAGAAGGGTACACTCACATAGTTGAGGTAACATTTGAGAGTGTGGAGACTATTCAG

GACTACATTATTCATCCTGCCCATGTTGGATTTGGAGATGTCTATCGTTCTTTCTGGGAAAAACTTCTCA

TTTTTGACTACACACCACGAAAGTAG
```

-continued

> AB164375.1| *Cannabis sativa* OLS mRNA for olivetol synthase (OLS), complete cds (SEQ ID NO: 9)
ATGAATCATCTTCGTGCTGAGGGTCCGGCCTCCGTTCTCGCCATTGGCACCGCCAATCCGGAGAACATTT

TATTACAAGATGAGTTTCCTGACTACTATTTTCCCGTCACCAAAAGTGARCACATGACTCAACTCAAAGA

AAAGTTTCGAAAAATATGTGACAAAAGTATGATAAGGAAACGTAACTGTTTCTTAAATGAAGAACACCTA

AAGCAAAACCCAAGATTGGTGGAGCACGAGATGCAAACTCTGGATGCACGTCAAGACATGTTGGTAGTTG

AGGTTCCAAAACTIGGGAAGGATGCTTGTGCAAAGGCCATCAAAGAATGGGGTCAACCCAAGTCTAAAAT

CACTCATTTAATCTTCACTAGCGCATCAACCACTGACATGCCCGGTGCAGACTACCATTGCGCTAAGCTT

CTCGGACTGAGTCCCTCAGTGAAGCGTGTGATGATGTATCAACTAGGCTGTTATGGTGGTGGAACCGTTC

TACGCATTGCCAAGGACATAGGAGAGAATAACAAAGGCGCAGGAGTTCTCGCCGTGTGTTGTGACATAAT

GGCTTGCTTGTTTCGTGGGCCTTCAGAGTCTGACCTCGAATTACTAGTGGGACAAGCTATCTTTGGTGAT

GGGGCTGCTGCGGTGATTGTTGGAGCTGAACCCGATGAGTCAGTTGGGGAAAGGCCGATATTTGAGTTGG

TGTCAACTGGGCAAACAATCTTACCAAACTCGGAAGGAACTATTGGGGGACATATAAGGGAAGCAGGACT

GATATTTGATTTACATAAGGATGTGCCTATGTTGATCTCTAATAATATTGAGAAATGTTTGATTGAGGCA

TTTACTCCTATTGGGATTAGTGATTGGAACTCCATATTTTGGATTACACACCCAGGTGGGAAAGCTATTT

TGGACAAAGTGGAGGAGAAGTTGCATCTAAAGAGTGATAAGTTTGTGGATTCACGTCATGTGCTGAGTGA

GCATGGGAATATGTCTAGOTCAACTGTCTTGTTTGTTATGGATGAGTTGAGGAAGAGGTCGTTGGAGGAA

GGGAAGTCTACCACTGGAGATGGATTTGAGTGGCGTGTTCTTTTTGGGTTTGGACCAGGTTTGACTGTCG

AAAGAGTGGTCGTGCGTAGTGTTCCCATCAAATATTAA

> JN717233.1 | PK04797.1 | Acyl-activating enzyme 1 (AAE1)

(SEQ ID NO: 10)
ATGGGTAAGAATTACAAGTCCCTGGACTCTGTTGTGGCCTCTGACTTCATAGCCCTAGGTATCACCTCTG

AAGTTGCTGAGACACTCCATGGTAGACTGGCCGAGATCGTGTGTAATTATGGCGCTGCCACTCCCCAAAC

ATGGATCAATATTGCCAACCATATTCTGTCGCCTGACCTCCCCTTCTCCCTGCACCAGATGCTCTTCTAT

GGTTGCTATAAAGACTTTGGACCTGCCCCTCCTGCTTGGATACCCGACCCGGAGAAAGTAAAGTCCACCA

ATCTGGGCGCACTTTTGGAGAAGCGAGGAAAAGAGTTTTTGGGAGTCAAGTATAAGGATCCCATTTCAAG

CTTTTCTCATTTCCAAGAATTTTCTGTAAGAAACCCTGAGGTGTATTGGAGAACAGTACTAATGGATGAG

ATGAAGATAAGTTTTTCAAAGGATCCAGAATGTATATTGCGTAGAGATGATGACATTAATAATCCAGGGG

GTAGTGAATGGCTTCCAGGAGGTTATCTTAACTCAGCAAAGAATTGCTTGARTGTAAATAGTAACAAGAA

ATTGAATGATACAATGATTGTATGGCGTGATGAAGGAAATGATGATTTGCCTCTAAACAAATTGACACTT

GACCAATGCGTAAACGTGTTTGGTTAGTTGGTTATGCACTTGAAGAAATGGGTTTGGAGAAGGGTTGTG

CAATTGCAATTGATATGCCAATGCATGTGGATGCTGTGGTTATCTATCTAGCTATTGTTCTTGCGGGATA

TGTAGTTGTTTCTATTGCTGATAGTTTTTCTGCTCCTGAAATATCAACAAGACTTCGACTATCAAAAGCA

AAAGCCATTTTTACACAGGATCATATTATTCGTGGGAAGAAGCGTATTCCCTTATACAGTAGAGTTGTGG

AAGCCAAGTCTCCCATGGCCATTGTTATTCCTTGTAGTGGCTCTAATATTGGTGCAGAATTGCGTGATGG

CGATATTTCTTGGGATTACTTTCTAGAAAGAGCAAAAGAGTTTAAAAATTGTGAATTTACTGCTAGAGAA

CAACCAGTTGATGCCTATACAAACATCCTCTTCTCATCTGGAACAACAGGGGAGCCAAAGGCAATTCCAT

GGACTCAAGCAACTCCTTTAAAAGCAGCTGCAGATGGGTGGAGCCATTTGGACATTAGGAAGGTGATGT

CATTGTTTGGCCCACTAATCTTGGTTGGATGATGGGTCCTTGGCTGGTCTATGCTTCACTCCTTAATGGG

GCTTCTATTGCCTTGTATAATGGATCACCACTTGTTTCTGGCTTTGCCAAATTTGTGCAGGATGCTAAAG

TAACAATGCTAGGTGTGGTCCCTAGTATTGTTCGATCATGGAAAAGTACCAATTGTGTTAGTGGCTATGA

TTGGTCCACCATCCGTTGCTTTTCCTCTTCTGGTGAAGCATCTAATGTAGATGAATACCTATGGTTGATG

-continued

```
GGGAGAGCAAACTACAAGCCTGTTATCGAAATGTGTGGTGGCACAGAAATTGGTGGTGCATTTTCTGCTG

GCTCTTTCTTACAAGCTCAATCATTATCTTCATTTAGTTCACAATGTATGGGTTGCACTTTATACATACT

TGACAAGAATGGTTATCCAATGCCTAAAAACAAACCAGGAATTGGTGAATTAGCGCTTGGTCCAGTCATG

TTTGGAGCATCGAAGACTCTGTTGAATGGTAATCACCATGATGTTTATTTTAAGGGAATGCCTACATTGA

ATGGAGAGGTTTTAAGGAGGCATGGGGACATTTTTGAGCTTACATCTAATGGTTATTATCATGCACATGG

TCGTGCAGATGATACAATGAATATTGGAGGCATCAAGATTAGTTCCATAGAGATTGAACGAGTTTGTAAT

GAAGTTGATGACAGAGTTTTCGAGACAACTGCTATTGGAGTGCCACCTTTGGGCGGTGGACCTGAGCAAT

TAGTAATTTTCTTTGTATTAAAAGATTCAAATGATACAACTATTGACTTAAATCAATTGAGGTTATCTTT

CAACTTGGGTTTACAGAAGAAACTAAATCCTCTGTTCAAGGTCACTCGTGTTGTGCCTCTTTCATCACTT

CCGAGAACAGCAACCAACAAGATCATGAGAAGGGTTTTGCGCCAACAATTTTCTCACTTTGAATGA
```

> JN717235.1 | PK13710.1| Acyl-activating enzyme 3 (AAE3)
(SEQ ID NO: 11)
```
ATGGAGAAATCTGGGTATGGAAGAGACGGTATTTACAGGTCTCTGAGACCACCTCTACACCTCCCCAACA

ACAACAACCTCTCAATGGTTTCATTCCTTTTCAGAAACTCATCTTCATACCCACAAAAGCCAGCTCTCAT

TGATTCCGAAACCAACCAAATACTCTCCTTTTCCCACTTCAAATCTACGGTTATCAAGGTCTCCCATGGC

TTTCTCAATCTGGGTATCAAGAAAAACGACGTCGTTCTCATCTACGCCCCTAATTCTATCCACTTCCCTG

TTTGTTTCCTTGGAATTATAGCCTCTGGAGCCATTGCCACTACCTCAAATCCTCTCTACACAGTTTCCGA

GCTTTCCAAACAGGTCAAGGATTCCAATCCCAAACTCATTATCACCGTTCCTCAACTCTTGGAAAAGTA

AAGGGTTTCAATCTCCCCACGATTCTAATTGGTCCTGATTCTGAACAAGAATCTTCTAGTGATAAAGTAA

TGACCTTTAACGATTTGGTCAACTTAGGTGGGTCGTCTGGCTCAGAATTTCCAATTGTTGATGATTTTAA

GCAGAGTGACACTGCTGCGCTATTGTACTCATCTGGCACAACGGGAATGAGTAAAGGTGTGGTTTTGACT

CACAAAAACTTCATTGCCTCTTCTTTAATGGTGACAATGGAGCAAGACCTAGTTGGAGAGATGGATAATG

TGTTTCTATGCTTTTTGCCAATGTTTCATGTATTTGGTTTGGCTATCATCACCTATGCTCAGTTGCAGAG

AGGAAACACTGTTATTTCAATGGCGAGATTTGACCTTGAGAAGATGTTAAAAGATGTGGAAAAGTATAAA

GTTACCCATTTGTGGGTTGTGCCTCCTGTGATACTGGCTCTGAGTAAGAACAGTTTGGTGAAGAAGTTTA

ATCTTTCTTCTATAAAGTATATTGGCTCTGGTGCAGCTCCTTTGGGCAAAGATTTAATGGAGGAGTGCTC

TAAGGTTGTTCCTTATGGTATTGTTGCTCAGGGATATGGTATGACAGAAACTTGTGGGATTGTATCCATG

GAGGATATAAGAGGAGGTAAACGAAATAGTGGTTCAGCTGGAATGCTGGCATCTGGAGTAGAAGCCCAGA

TAGTTAGTGTAGATACACTGAAGCCCTTACCTCCTAATCAATTGGGGGAGATATGGGTGAAGGGGCCTAA

TATGATGCAAGGTTACTTCAATAACCCACAGGCAACCAAGTTGACTATAGATAAGAAAGGTTGGGTACAT

ACTGGTGATCTTGGATATTTTGATGAAGATGGACATCTTTATGTTGTTGACCGTATAAAAGAGCTCATCA

AATATAAAGGATTTCAGGTTGCTCCTGCTGAGCTTGAAGGATTGCTTGTTTCTCACCCTGAAATACTCGA

TGCTGTTGTGATCCCATTTCCTGATGCTGAAGCGGGTGAAGTCCCAGTTGCTTATGTTGTGCGCTCTCCC

AACAGTTCATTAACCGAAAATGATGTGAAGAAATTTATCGCGGCCCAGGTTGCATCTTTCAAAAGATTGA

GAAAAGTAACATTTATAAACAGTGTCCCGAAATCTGCTTCGGGGAAAATCCTCAGAAGAGAACTCATTCA

GAAAGTACGCTCCAACATGTGA
```

> PK04410.1 | Hydroperoxide lyase (HPL)
(SEQ ID NO: 12)
```
ATGTCTTTTATGATGAGCATGAATCCTTCTCCCTCCTCGCCACCGCCACCGTTATCGTCGCCGTCGGAAT

CTTCCTCAACGCCGTCAACACTGCCAGTCCGTACGATCCCGGGAAGCTACGGATGGCCGTTACTGGGGCC

CATCTCGGACCGGTTAGACTACTTCTGGTTCCAAGGCCCAGATACGTTTTTCAGAAAAAGAGTAGAGAAA

TACAAGAGCACAGTGTTCCGTACCAACATACCCCCGACCTTTCCTTTCTTCAGCGTTAATCCGAACATTG

TGGCCGTGCTGGACTGTAAATCATTTTCTCATCTTTTCGACATGGAAATTGTCGAGAAAAAGAATGTTCT
```

-continued

```
TGTTGGAGATTTCATGCCCAGTGTCAATTACACTGGTGATATTAGGGTTGGAGCTTATCTCGACACTTCT
GAACCACAACACGCTAAGGTTAAGAACTTCGCAATGGATGTACTAAAACAAAGCTCGAAGATATGGGTGG
GAGAACTGACATCAAATCTGTCGACGATGTGGGACACAATAGAAAAAGACGTATCTGAGAAATCATCCTC
ATCCTACTTAGCCCCACTTCAAAAGTTCTTGTTCAACTTCCTGGTCAAGTGTCTAATTGGTGCTGACCCT
TCCAACTCCCCCAAGATTGCAGAGTCTGGCTACATCATGCTCGACCGATGGTTAGCCTTCCAGCTCCTTC
CCACTATCAAGATTGGGATCCTTCAGCCTCTTGAGGAGCTTTTCATTCACTCTTTTGCCTATCCTTTTTT
CTTGGTCAGTGGTGACTACAATAACCTCTCCAGTTTTGTAGAGGAATATGGTAAAGAAATAGTAGCGAGA
GGTGAAACCGAGTTCGGGCTGAGTAAACAAGAAGCGATTCACAACCTTCTCTTCATTTTGGGTTTCAACG
CCTTCGGGGGATTCTCTATATTTCTACCGAGCCTACTGGGCACCGTGGCGAGTGACACAACCGATCTACA
ACAAAGACTGGTCAAAGAAGTCAGACAAAATGGCGGGTCAACTCTGACGTTTGACTCGATCAAAGAAATG
CCACTCGTTCAATCGGTCGTGTACGAGACTCTCCGGCTCAATCCACCTGTTCCGCTCCAATTCGCCAGGG
CCAGGAAGGACTTCCGGCTCAGCTCGCACGACGCGGCCTTCGAGGTGAAGAAAGGCGAGCTCCTATGCGG
GTTTCAAAGCCTTGTTATGAGGGACCCAAAAATATTCTCGGAACCGGAGTCGTTCATTGGGACCGGTTC
ATGAAAGATAAAGGTCTCTTAGATTATCTTTACTGGTCCAATGGACCTCAAACCGGTGTGCCCAGCGTCA
CCAATAAGCAATGCGCGGGAAAAGATATCGTCACGCTTACGGCTTGTTTGATCTTGGCTTACACCTTCCG
TCGTTATGACTCCATCAGCGGGAGCTCAAGTTCAATCACAGCCCTTAAAAAGGCTTAA
> PK08276.1 | Lipoxygenase (LOX1)
                                                                   (SEQ ID NO: 13)
ATGTTGAAGCCTCCTCATCAAGTAGTTCAAAATTTGAAATATGAGAAAACCCTAGTTCTTTTGAACAAGC
CATTCATCCATGGCTACAACGGGGCTATTATCGGTGTCAACTCTCGGCTATTTCCAGTAAAACCTAAAAC
CAAAAGACGAGTCGCTTCATCATCATCATCATCATCTCCCGGAACCAAAAACATTATTAAAGCTTCTTTA
TTTTCTCCAATGGAGAAGAAGAATACAGCTAGGGTTTCGGTTAGTGTGGCGGTACAACGTGTGACTCCAA
AGTTTTGGAGATTTGAATTGTCTGAGAAAATCCAAGATGGACGTGATAGGCTTGAGGATCTTCTAGGGCT
AAACTCTTTAAGTATTGAGCTTGTTAGTACTCAAAAAGATCCAGTAACGGGGAAAGAGCGAACGGTTAAA
GGTTTTCCAAAAAGGCCCAACTTTAACATATTTTCATCAAGTGATGTAAAATACGAAGCGAAATTTGACA
TACCAAAAGATTTTGGAGAAGTGGGTGCTATAATCGTCGAAAATGATTTTGAAAGAGAAATATTTTTAAA
GAATATTATACTCGAAGACTTGCCCTCCGAACCAAGCACCCTTGAATTCTCTTGCAACTCGTGGGTTCAG
TCCAAACATGATGTCCCTACTGATCAACACAAGAGAGTCTTCTTCTCTAATAAGTGTTACCTACCATCAC
AAACACCAAGTGGGATAAAAGAATTGAGAAAAATTGCATTGGAAAATTTGAGAGGAGATGGAAAAGGAGA
GAGGAAGAAGAATGAAAGAGTTTATGATTATGATGTGTATAATGATCTTGGACAACCGGACAACAATGAT
GACCTAAAAAGACCTATTCTTGGCGGATCAAAAGAATTCCCTTATCCTAGGCGTTGTAGAACCGGACGGC
CTCCAACTGAAACTGATCCATTATCTGAGTCAAGGATTAGTGATTTTTATGTACCAAGAGATGAAGAATT
TGCAGAAGTGAAGCAAAGTAATTTTAGTTTGAAGACTGTATACTCAGTAATACATGCAGTGATTCCCATA
CTCAGACAAGTCTTAATTGATGAAAATTTCCCATACTTCACTGCCATTGATGTTCTCTATGATGAAGGCA
TTAAAATCCCTTCTAATGCTGAAAAGACCTTAATTCAAACCATCAAAAATGTCAATGCAAGAATATACAA
AACTGTTTCTGATGCTGATGATTTTTTACAGTTTCAGCAGCCTCCAACCATGGACAAGGACAAATTCTTC
TGGTTTAGAGATGAAGAGTTTTGTAGACAAACTATTGCCGGTCTCAACCCTTGCTGCATTGAATTGGTTA
AGGAGTGGCCTTTGAAAAGTGAACTTGACCCCACAATCTATGGCCCACCAGAGTCAAAAATCACCACAGA
ATTGGTTGAGAAATTCATCAAAGTATATGGCTACAATAATATTAATGAGGCTTTAAAAGAAAAAAAATTG
TTCATGTTGGATTACCATGATGTATTATTACCATATGTTAGCAAAGTAAGGGAACTGGAAAATAAACCT
TGTATGGATCAAGAACACTTTTTTTCTTGACTCCTTATGGTACATTGTTGCCTTTGGCCATTGAATTGAT
```

```
TCGGCCACCGATGGATGGTAAGCCGCAATGGAAGGAAGTCTACACCCCGATGAATTGGCATTCTACCGAT

CTTTGGCTTTGGAGACTCGCAAAAGCTCATGTCCTTGCTCATGATTCCGGTGTTCATCAACTCGTTAGTC

ACTGGCTAAGAACACATTGTGCAGTTGAGCCATATATAATTGCAACAAATAGACAATTGAGTGCAATGCA

TCCTATCCATAGATTATTGAAGCCACATTTTAGATACACAATGGAGATTAATGCTCTTGCTCGAGAAAGT

TTGATCAATGCAGGTGGTATCATCGAAACAGCATTTGCACCTGGAAAATATTCTATGGAGTTAAGCTCCG

TCATGTACGACAAACAATGGCGATTCGATCTACAAGCATTGCCAGCTGACCTAATTCATAGAGGAATGGC

TGTTGAGGACAAGGATAGTGAACATGGTGTAAGAGTAATAATTGAAGATTACCCTTACGCCAACGACGGT

CTTCTCATATGGAGCTCCATCAAACAATGGGTTACTGACTACGTCAACCACTACTACCCTACCTCCAGTG

AGGTAGAGCGCGACGAAGAATTACAAGCATGGTGGACAGAGATCAGAACTGTAGGTCACGCTGACAAGAA

AGACGCACCTGGGTGGCCTGACTTAAAAACGAAACAAGATCTCATAGACATTGTCACAAACATGGCATGG

ACAGCATCAGCTCACCATGCAGCTGTCAACTTTGGACAATATGCTTACGCTGGCTATTTCCCTAACCGAC

CAACCATAACAAGAACTGTTATGCCGTCAGAAGAGAAGGAGTATAACCTAGATGCGTGGAAACACTTCAA

AAATAGTCCTGAAGACGCCCTTTTGAAGTGCTTACCTACGCAATTACAAGCAGGCCTAGTTGTGGCCGTG

TTAGACGTGTTGTCTACTCACTCGCCAGACGAAGAGTATCTTGGAGACAAGATGGAACCCTCGTGGGGCT

CGAATCTTGTTATAGGGAAGCTTTTAATCGGTTCAATAAGAGGATGAACGAGATTGAAAGTATCATTAA

TGAAAAGAATGATAATGAGAATTTAAGGAATAGACATGGAGCTGGAATTTTGTCTTATGAACTTCTCAAG

CCCTTTTCTGAGCCTGGTGTCACTAACAAGGGTATTCCATATAGCATATCTATTTGA

> IM00001.1 | Desaturase (DS) Coding sequence
(SEQ ID NO: 14)
ATGGGAGCCGGTGGCAAAAATAGTAGACTTGAGCGAGCACCACACACCACACCACCATTCACACTAAGCC

AACTCAAGAAAGCCATTCCACCCCATTGCTTCAACCATTCTCTTCTTCGTTCCTTCTCTCATGTCCTTCA

AGACCTTTTTTTCTCCTTTTTGTTCTACTACATAGCAACCTCTTACTTCCATCTTCTCCCACACCCGCTC

CAATACTTAGCTTGGCCACTTTATTGGATCTTCCAAGGCAGCATTTTTGCTGGTATTTGGGTCCTTGGTC

ATGATTGTGGTCACCAAGCTTTCAGTGACCACCAATGGGTGGATGACAcGTTGGCTTTGTCCTCCACTC

CGCTCTTCTCTTCCCATACTTCTCTTTTAAGTATAGTCATCGTCGCCATCATTCAAACATCGGCTCCCTT

GAACATGATCAATTGTTTGTTCCAGTCCCCGAATCTCAAATCGCATGGCTCTACAAACgTTACTTGGACA

ATCCACTAGGAAGAGCCCTAAAGCTTTCCACTATAGTGTTCCTTGGTTtCCTTTGTACTTAGGTTTCAA

TCTTACAGGCAAACcATATGATCGTTaTGCATGTCATTATGATCCTTACTCTCCACTCTACTCAAAAAGT

GAAAGGCTTCATATATTGATTTCAGATATCGGTGTTTTCATCACCACATTaGTGTTATACCAGCTTGGCT

CGACTAAAGGgTTGAGTTGGCTTGTGTTCATGTATGGGGTGCCATTGTTTACAGGGAATAGCATCCTTGT

GACAATCGCATACTTGAATCATACTCACCCTTCATTGCCTCATTATGACTCGTCaGAGTGGGATTGGTTG

AAAGGAGCATTGTCAACAACTGATCGAAACTATGGATCAATTCTCAATAGGGTTTTCCATCACCTTACAG

ATGCTCATATGGCACACCATTTATTCGCAACAATACCTCACTACCATGCAAATGAAGCCACCAAAGTTAT

CAAATCCATATTGGGAGAATACTACTCTTTTGATGATACTCCAATAATTAAAGCTCTTTGGAGAGAGACT

AAGGAGTGTGTCTATATTGAGCCAAATCATGAATCTTCTCCTAATAATAACAAAGGTGTTTTCTGGTACA

ACAACAAGTTCTGA

> PK10442.1 | Geranyl pyrophosphate (GPP) synthase large subunit |
GPP synthase lsu
(SEQ ID NO: 15)
ATGAGCACTGTAAATCTCACATGGGTTCAAACCTGTTCCATGTTCAACCAAGGAGGTAGATCCAGATCCT

TATCAACTTTCAATCTCAATCTCTACCACCCTTTGAAAAAAACACCCTTTTCAATCCAAACCCCAAAACA

AAAACGACCCACTTCACCATTTTCATCAATCTCAGCTGTTCTAACCGAGCAAGAAGCCGTTAAAGAAGGC

GATGAAGAAAAATCCATCTTCAATTTCAAGTCTTACATGGTCCAAAAAGCCAACTCAGTCAACCAAGCTT
```

-continued

```
TAGACTCAGCCGTTTTGCTCAGAGATCCCATTATGATACACGAGTCCATGCGTTACTCACTCCTCGCCGG

AGGAAAACGAGTCAGACCCATGCTCTGTCTCTCAGCCTGTGAACTCGTAGGCGGAAAAGAATCCGTAGCC

ATGCCGGCTGCCTGCGCCGTCGAAATGATCCACACCATGTCTCTAATCCACGACGACCTCCCTTGTATGG

ACAACGATGACCTCCGCCGTGGAAAGCCCACAAACCACAAAGTCTTCGGAGAAGACGTGGCCGTTTTAGC

CGGCGATGCACTTTTAGCCTTTGCTTTTGAGCACATGGCGGTCTCTACCGTTGGTGTTCCGGCAGCCAAG

ATTGTCAGGGCGATTGGTGAGCTTGCTAAGTCAATTGGGTCAGAAGGATTAGTGGCTGGTCAAGTGGTTG

ATATTGATTCAGAGGGTTTGGCTAATGTTGGGCTTGAACAACTTGAGTTCATTCATCTCCATAAGACTGG

GGCTCTTCTAGAAGCTTCTGTTGTTTTGGGGGCTATTCTTGGTGGTGGTACAGATGAAGAAGTTGAAAAA

CTTAGGAGCTTTGCTAGGTGTATTGGCTTGCTTTTTCAGGTTGTTGATGACATTCTTGATGTGACTAAAT

CTTCTCAAGAATTGGGTAAAACTGCTGGGAAAGATTTGGTGGCTGATAAGGTTACTTATCCAAGGCTAAT

GGGTATTGACAAATCAAGAGAATTTGCTGAGCAATTGAACACAGAAGCCAAACAGCATCTTTCTGGTTTT

GATCCCATAAAGGCTGCTCCTTTAATTGCTTTGGCTAATTATATTGCTTATAGGCAAAATTGA
```

> PK15935.1 | Geranyl pyrophosphate (GPP) synthase small subunit |
GPP synthase ssu (SEQ ID NO: 16)
```
ATGGCGGTTTATAATCTATCAATTAATTGCAGTCCAAGATTTGTTCATCATGTTTACGTTCCACATTTCA

CATGTAAATCCAATAAGTCGTTAAGTCACGTACCCATGAGAATAACCATGTCCAAACAGCATCATCATTC

TTATTTTGCCTCCACAACAGCCGATGTAGATGCCCATCTCAAGCAATCCATCACTATCAAGCCACCACTC

TCAGTTCACGAGGCCATGTACAATTTCATCTTTTCCACACCTCCGAATTTAGCACCGTCATTGTGCGTGG

CGGCGTGTGAGCTTGTCGGGGGCCACCAGGACCAGGCCATGGCAGCAGCCTCCGCCTTGCGCGTCATCCA

CGCAGCCATCTTCACTCATGACCACCTCCCTTTAACGGGCAGGCCCAATCCAACAAGTCCTGAGGCAGCG

ACCCACAATTCTTACAACCCAAATATTCAGCTCCTTCTCCCGGACGCAATTGTACCTTTTGGGTTCGAAT

TGTTGGCCAATTCTGATGACCTTACCCATAATAAATCAGATCGGATTTTGCGGGTCATTGTAGAGTTCAC

ACGCACCTTTGGATCACGAGGAACTATTGATGCTCAATACCATGAGAAGCTAGCCAGTAGATTTGACGTT

GATAGTCATGAAGCCAAAACTGTCGGGTGGGGCCATTATCCCTCTTTGAAGAAGGAAGGTGCGATGCATG

CATGCGCTGCTGCATGTGGGGCCATTCTTGGAGAGGCACATGAAGAAGAGGTTGAGAAGTTGAGAACTTT

TGGTCTTTATGTGGGCATGATTCAAGGATATGCCAATAGATTTATAATGAGCAGCACAGAAGAAAAGAAA

GAAGCAGATAGAATCATCGAGGAGTTAACCAATTTGGCTCGCCAGGAACTAAAATATTTCGATGGGAGAA

ACTTAGAGCCATTTTCAACCTTTCTTTTTCGTCTATAG
```

> PK17903.1 | Geranyl pyrophosphate (IPP) Isomerase (SEQ ID NO: 17)
```
ATGGGAGACTCTGCCGACGCTGGAATGGACGCTGTCCAGAGACGCCTTATGTTTGATGATGAATGCATTC

TAGTGGATGAGAATGACCGAGTTGTTGGTCATGATACAAAATATAACTGTCACTTGATGGAAAAGATTGA

AAAGGATAATTTGCTACACAGGGCTTTCAGTGTGTTCTTGTTCAACTCAAAATATGAGTTGCTTCTTCAG

CAACGTTCTGCAACAAAGGTAACATTCCCTCTTGTGTGGACAAACACCTGTTGTAGCCACCCGCTCTACC

GTGAATCTGAGCTTATCGATGAGGAGTCCCTTGGAGCAAGGAATGCAGCACAGAGAAAGCTTTTAGATGA

GCTGGGTATTCCTGCTGAAGATGTGCCAGTTGATCAATTTACCCCACTAGGCAGGATGCTGTACAAAGCT

CCTTCTGATGGCAAATGGGGCGAGCATGAACTTGATTACCTGCTCTTCATCGTCCGGGATGTTAGTGTCA

ATCCAAATCCAGATGAAGTAGCTGATATCAAGTATGTAAACCGGGACGAGTTGAAAGAGTTGTTGAGGAA

AGCAGATGCTGGGGAAGGAGGCTTGAAGCTATCCCCTTGGTTCAGACTGGTTGTGGATAATTTCTTGTTC

AAGTGGTGGGACCATGTTGAGAAAGGCACACTTAAGGAAGTTGCTGATATGAAAACCATTCACAAGTTGA

CTTAA
```

> PK16122.1 | 1-deoxyxylulose-5-phosphate synthase 1 (DXS1)

(SEQ ID NO: 18)

ATGGCGTTTTGTGCATTATCATTTCCTGCTCATATTAGCCGGGCAACTACACCAGCACCTTCAGATCTTC

ACAAATCTAGTTCTTTCTCTTCTCGGTTTTATTGGGGAGCAGATCTGCTGAGGCCATCTCAATACAAGGT

CAGGAAAATACAAAGTGGGGTTTATGCATCACTGTCAGAAAGTGGAGAATATCACTCAAGGAGACCACCA

ACTCCTCTCTTGGACACCATAAATTATCCAATTCATATGAAAAATCTCTCTGTTAAGGAGCTTAAACAAC

TATCAGATGAACTAAGGTCTGATGTCATCTTCAACGTTTCTAACACCGGGGGTCACCTGGGCTCAAGCCT

TGGTGTTGTTGAGCTTACTGTGGCTCTTCATTTTGTCTTCAATACTCCTCAGGATAGGATACTATGGGAT

GTTGGTCATCAGTCTTACCCTCATAAAATTCTGACTGGAAGAAGAGATAAGATGCACACCATGAGGCAGA

CCAACGGGTTAGCCGGATTCACTAAGCGGTCTGAGAGTGAATATGATTGTTTTGGGACTGGTCATAGTTC

TACCACCATCTCAGCTGGCTTGGGAATGGCTGTTGGAAGGGATCTTAAAGGAAGAAAGAATAATGTTGTG

GCTGTCATAGGTGATGGTGCCATGACAGCAGGTCAAGCTTATGAAGCCATGAATAATGCCGGGTACCTTG

ATTCCGACATGATTATTATTCTTAACGACAATAAACAGGTTTCTTTACCTACTGCCTCTCTTGATGGGCC

CATACCACCTGTTGGAGCTTTGAGTAGTGCTCTCAGTAGGCTGCAATCAAACAGGCCTCTTAGAGAACTA

AGAGAAGTAGCCAAGGGAGTTACTAAACAAATAGGTGGATCAGTACATGAATTGGCTGCAAAAGTTGATG

AATATGCTCGTGGAATGATAAGTGGTTCTGGCTCAACATTGTTTGAGGAGCTTGGACTCTATTATATTGG

TCCAGTTGATGGTCACAATATAGATGATCTTGTTTCCATACTAGAGGAGGTTAAGAGCACTAAAACAACA

GGTCCAGTCTTGATCCATTGCATCACTGAGAAAGGAAGAGGATATCCATATGCAGAGAAAGCTGCTGATA

AGTATCATGGGGTGGCCAAGTTTGATCCAGCAACTGGAAAGCAATTCAAAGGCACTTCTAACACACAGTC

ATACACTACATACTTTGCTGAGGCTTTGGTTGCAGAAGCAGAGGCAGACAAAGATGTTGTGGCCATCCAT

GCTGCAATGGGTGGTGGAACAGGCTTGAATCTCTTCCTTCGCCGTTTTCCAACAAGATGTTTTGATGTTG

GGATAGGAGAACAGCATGCTGTTACTTTCGCTGCTGGTTTGGCTTGCGAGGGCCTTAAGCCGTTTTGTGC

AATTTACTCATCTTTCATGCAGCGAGCCTATGATCAGGTAGTACATGATGTTGATTTGCAGAAGTTGCCG

GTGAGATTTGCAATGGACAGAGCTGGACTTGTTGGGGCCGACGGCCCTACACATTGTGGTGCTTTTGATG

TTACTTTCATGGCATGCCTCCCAAACATGGTTGTGATGGCTCCTTCCGATGAGGCAGAGCTCTTCCACAT

GGTTGCCACCGCTGCTGCCATAGATGACAGACCAAGTTGTTTCCGTTACCCCAGAGGAAATGGAATTGGT

GTTCCATTACCTCAAGGGAATAAAGGAACTCCTCTTGAGATCGGAAAAGGCAGGGTATTGGTTGAAGGGG

AAAGAGTAGCACTTCTAGGCTATGGAACAGCAGTTCAGAGTTGTTTGGCTGCTGCAGCCTTAGTAGAACC

TCACGGTCTACGGCTAACAGTTGCTGATGCACGATTTTGCAAGCCTTTGGATCATGCCCTCATTCGCGAA

CTAGCGAAAAATCACGAGGTTTTGATTACAGTGGAAGAAGGATCTATAGGAGGTTTTGGATCTCATGTTG

CTCAGTTTATGGCCCTTGATGGCCTTCTTGATGGAAAAACAAAGTGGAGACCAATTGTTCTTCCTGACCG

ATACATCGACCACGGTTCGCCTGCTGATCAATATGTCGACGCGGGTCTCACGCCACCTCACATTGCAGCC

ACAGTTTTCAATGTACTAGGACAAACAAGAGAGGCCTTGAAGGTTATGACAACATGA

> PK26473.1 | 1-deoxyxylulose-5-phosphate synthase 2 (DXS2)

(SEQ ID NO: 19)

ATGGCGGTTTCTGGTTCATTCATTGTACCAAATCATTCATTCCTTTCACAACTTAAATCTCCACAGCCAT

ATTACAGTTCCAACAAACAGTTGAGTTTAAGGGTGAGAGGATCTCTTTGTAGCTCAGATGATGGGGAAGG

AAAATTCATCAGCAAAGAAAAAGATGAATGGAAAATCAAGTATTCCAGTGAAAAACCAATCACTCCATTG

CTTGATACAGTCAATTACCCAGTTCACATGAAGAATTTATCCACACAGGATCTTGAACAGCTAGGAGGAG

AGCTTAGAGGAGATGTAGTCCATACAGTATCAAAAACAGGTGGTCATCTGAGTGCAAGCTTGGGAGTTGT

GGAGCTCACTGTAGCACTGCATCATGTTTTCAATACCCCTGATGATAAAATCATATGGGATGTTGGACAT

CAGACATACCCGCATAAGATTCTTACAGGAAGGAGGTCTCAAATGCATACCATTAGAAAGACTTCTGGTC

TAGGAGGGTTTCCCAAAAGAGATGAGAGTGTTTACGATGCTTTCGGTGCAGGTCACAOTTCTACAAGCAT

-continued

```
ATCAGCAGGCCTTGGCATGGCAGTTGCCAGGGATCTTCTGGGALAGAAGAACAGTGTTGTTTCTGTGATT

GGAGATGGGGCCATGACTGCAGGAATGGCATATGAAGCCATGAATAATGCCGGCTACTTGGACGCCAACT

TGATTGTTGTATTAAACGACAATAAACAAGTTTCTTTACCAACTGCTACTCTTGATGGTCCTGCAACCCC

AGTGGGAGCTCTAAGTGGTGCTTTGACTAASCTTCAAGCAAGCACCAAGTTCAGAAAACTTCGCGAAGCT

GCGAAAACCATCACAAAACAAATTGGAGGGCCAGCACATGAAGTTGCAGCTAAAGTAGATGAGTATGCTA

GAGGAATGATAAGTGCTTCTGGGTCAACACTCTTTGAGGAGCTTGGGTTGTATTATATTGGTCCGGTGGA

TGGACATAATGTTGGAGATTTAGTCACCATTTTTGAGAAAGTGAAATCAATGCCAGCGCCAGGACCAGTC

TTGATCCACATCGTCACAGAGAAAGGGAAAGGCTATCCCCCAGCTGAAGTAGCACCTGATAAAATGCATG

GAGTTGTAAAGTTTGACCCAACAACAGGAAAGCAATTTAAGTCCAAATCGTCGACACTTTCATATACTCA

ATACTTTGCTGAATCTCTAATAAAAGAAGCTGAAGAAGATGACAAGATTGTTGCCATACACGCAGCAATG

GGTGGTGGCACTGGTCTCAATTATTTCCAGAAGAAATTTCCTGATCGTTGCTTTGATGTGGGGATTGCTG

AGCAACATGCTGTCACGTTTGCAGCTGGATTAGCTGCAGAGGGTCTCAAACCATTCTGTGCCATATACTC

ATCATTCCTGCAACGAGGATATGATCAGGTTGCACATGATGTAGACCTTCAAAAATTACCTGTCCGTTTT

GCATTGGATAGAGCTGGCATGGTTGGCGCAGATGGGCCTACCCACTGCGGTGCATTTGATATCACCTACA

TGGCCTGCTTGCCCAACATGGTTGTCATGGCTCCATCAGATGAGGCTGAACTTATGCACATGGTGGCCAC

AGCAACAGCTATAGATGACAGACCCAGTTGCTTCAGGTTTCCAAGGGGCAATGGAATTGGAGCAAAGCTT

CCAGCTAATAATAAAGGAACTATACTTGAGATTGGAAAAGGCAGAATATTAATGGAAGGCAGCAGAGTAG

CTATTTTGGGTTATGGTTCTATTGTTCAGCAATGTGTGGAAGCTGCAAGCATATTAAAGAAACAAGACAT

TTCAGTGACAGTAGCTGATGCAAGATTTTGCAAACCATTGGATACAAATCTCATAAGACGGTTAGCCAAC

GAGCATGAAATCCTAATCACTGCCGAAGAAGGTTCTATTGGAGGCTTTGGGTCTCATGTGTCACACTTTC

TAAGCTTAAGTGGACTTCTTGATGGGTCTTTAAAGTTGAGAGCAATGGTTCTTCCTGATAGATACATTGA

CCATGGATCACCCCAAGATCAGACTGAAACAGCCGGGCTCTCCTCGAGGCATATATCTGCAACAGTCTTA

TCTCTCTTGGGGAAGCCCAAGGAAGCACTTCAGTTCATGTAA
```

> PK04218.1 | 1-deoxy-D-xylulose 5-phosphate reductoisomerase (XDR)
(SEQ ID NO: 20)

```
ATGGCTCTGAACTTGTTATCCCCAGCTGAAGTGAAGGCTCTATCCTTTTTGGACTCCACCAAGTCCACCC

GCTTCCCTAAGCTGTGTCCAGGTGGAATTACTTTGCATAGAAAGGATTGCAGAGTACCACTTAGAAGAAG

AGTTCATTGTTCGTTGCAGCAACCTCCTCCAGCTTGGCCAGGAAGAGCTATTCCAGAGCAAGATCTTTGT

AATTGGAATGTCCCAAAGCCTATATCTATTATTGGCTCTACTGGCTCTATAGGAACTCAGACACTGGACA

TTGTGGCAGAGAATCCAGATAAATTCAGAATAGTGGGACTTGCAGCTGGTTCGAATGTGACACTTCTTGC

AGACCAGGTGAAGAGATTCAAGCCTCAAATAGTTGCTCTTAGAAATGAATCATTAATTGGTGAACTAAAA

GAGGCCTTAGCTGATGTGGAAGAAATGCCCGAAATTATTCCTGGGGAACAAGGAGTAATTGAGGTTGCCC

GGCACCCAGATGCAGTCACAGTGGTTACAGGAATAGTAGGTTGTGCTGGATTACAGCCTACAGTTGCTGC

AATTGAGGCAGGTAAACACATAGCTTTAGCCAATAAAGAGACCCTGATTGCTGGAGGTCCATTCATCCTT

CCTCTAGCTCACAAGCATAACATAAAAATTCTTCCTGCCGATTCAGAACATTCGGCAATATTCCAGTGTA

TCCAGGGCTTGCCTGATGGTGCACTACGGCGTATCATTTTGACAGCATCTGGGGAGCTTTCAGAGATTG

GCCGGTTGAAAAGCTAAAGATGTTAAGGTTGCTGATGCTCTGAAACATCCAAACTGGCCGGGTATGGGA

AAGAAAGTCACTATTGATTCTGCTACCCTTTTCAACAAGGGTCTGGAAGTCATTGAAGCCCATTATCTAT

TCGGAGGAGACTATGACGATATTGACATTGTGATTCACCCAGAAGCTATTATACACTCTATGATTGAAAC

ACAGGATTCTTCTGTTCTGGCTCAGTTAGGGTGGCCTGACATGCATATACCGATTCTCTATACTATGTCA

TGGCCAGACAGAATATACTGTTCTGAAGTAACTTGGCCTCGACTTGATCTTTGCAAGCTTGGTTCGCTGA
```

-continued

```
CCTTTAGGAGTCCTGACAACCAGAAGTACCCATCCATAGATCTTGCCTATTCTGCTGGACGTGCTGGGGG

CACCATGACTGGAGTTCTCAGTGCAGCCAATGAGAAAGCTGTAGAGATGTTTATTGATGAGAAGATAAGT

TATCTTGAAATCTTCAAAGTTGTTGAGCTAACATGCGACAAGCATCGATCAGAGATGGTGACTTCACCTT

CTCTTGATGAAATTATCCACTATGACTCGTGGGCACGAGAGTATGCAACTACTAGTTTGAAGAGTTCTTC

CAGTCCAAGACCTGTTACAGCATGA
```

> PK03569.1 | 4-diphosphocytidyl-methylerythritol 2-phosphate synthase (MCT)

(SEQ ID NO: 21)

```
ATGGCGTTACTTGCAATGGACCTTACTTTCTCTTCTGCTTCTCTTTCTTCTTCCTACAATGCTGCTC

CTCTACTATTTCCTTCTATTCGCCCATCCTCTCAATCCATTGTTCGATTCCCAGTCCATGAGGTGGGATT

CAGGGGGAAATGCAGAATTTCCAAGATAAGGTTCGCTCGCTGCTCTGCAAATGTTGGCCAAAAGCCTGGT

GTTGTGGAAAAGAAAAGCGTTTCGGTGGTTCTTCTGGCAGGTGGGAAGGGTAAACGGATGGGGCCAACA

TGCCAAAGCAGTATCTTCCACTTITAGGGCAACCAATTGCACTGTATAGCTTCTACACTTTTTCTAAAAT

GATTGAAGTGACTGAAATTGTTGTAGTTTGTGATCCCTCTTACGAGGATATCTTTGAAGATTCCAAAGTC

AAGATCCATGTTGGACTTAAATTCGCTCTGCCTGGAAAGGAAAGACAGGATTCAGTTTATAGTGGACTTC

AGGCAATTGATCCAAACTCTAAGCTTGTGTGCATTCACGATTCTGCTAGACCTTTGGTAACAACAGAAGA

AGTTAAAAAGGTCATTGAAGATGGTTGGTTGCATGGAGGAGCTGTACTTGGTGTTCCTGTCAAAGCTACA

ATCAAAGAGGCAAACAATGCATCTTTTGTAACTAAAACGTTGGAGAGGAAAAAACTTTGGGAAATGCAGA

CACCCCAGGTGATCAAACCCGAGTTGCTCAAGGAAGGATTTGAGCTTGTAAATAGGGAAAATCTGGAAGT

GACTGATGATGTGTCTATAGTGGAACACCTTGGACATCCTGTATATATAACTGAAGGTGCTTACACCAAC

ATCAAGGTTACTACTCCAGATGATTTATTGCTTGCGGAGAGAGTATTGAGTATGAACTCTGTGAAGGCTG

TTGCATAA
```

> PK19074.1 | 4-diphosphocytidyl-2-C-methyl-D-erythritol kinase (CNK)

(SEQ ID NO: 22)

```
ATGGCTTCCTCTCATATTCTCTGCCACAACAACGTTTTTAATCTTTCTCCCAATCCTTTTAGGAACAGGG

GTCTCTCTTCCTTAAACTCAAATGGGTTTTGTTTTTTGGTTCGAAATCTAGAATTTCGAGGCCTTCATC

TCTCAAAATTGTGGTTTCTGAAAGAAGACAAGTTGAGATAGTTTATGATGCTGATGAAAGGATAAACAAA

TTGGCTGATGTAGTGGACAAGGAAGCGCCTCTTTCTAGGCTCACTCTTTTCTCACCTTGCAAGATTAATG

TTTTCTTGAGAATAACTAGCAAAAGGGAAGATGGGTATCATGATTTGGCATCCCTCTTTCACGTGATAAG

TCTTGGAGATGTGCTTAAGTTCTCTTTGTCTCCTTCAACAAAGAAAGATTCTTTGTCAACGAATGCCTCT

GGGGTACCACTTGATGATAGAAATTTGATTATCAAGGCCCTTAATCTTTACCGAAAGAAAACTGGTACAA

ACAAATACTTTTGGATTCATCTTGACAAGAAAGTGCCCACTGGAGCAGGGCTAGGTGGTGGGAGCAGCAA

TGCTGCAACAGCCCTATGGGCAGCAAATCAGTTCAATGGTTGTCTTGTTACTGAAAAGGAATTGCAAGAA

TGGTCAAGTGAGATTGGTTCAGATGTTCCTTTCTTTTTCTCCCAAGGGGCAGCCTATTGTACAGGTCGAG

GTGAGGTTGTTCAGGATATTCTACCACCTGTACCATTAAACATTCCCATGGTTCTCATAAAGCCCCCAGA

AGCATGTTCAACAGCCGAAGTTTATAAGCGTTTTCGGTTGGATAAAACCAGTAATAGTGATCCTTTACAA

TTGCTCCACAAGATCTCAAGTGATGGAATAAGTCAAGATGTCTGCATCAATGACTTAGAACCTCCTGCCT

TTGAAGTTCTTCCATCTCTTAAGAGATTGAAACAGCGTATAATTGCAGCTAGTCGTGGACAATATGATGC

TGTTTTTATGTCTGGGAGTGGAAGCACCATTGTCGGGGTCGGTTCCCCAGATCCACCTCAGTTTATATAT

GATGATGAGGACTACAAGGATGTGTTTTTGTCAGAGGCCAACTTTCTGACTCGAGAAGCAAATGAATGGT

ACAAAGAACCTGCTTCAGCTAGCGCTTGTAGCCCTTCAGATGATTTCTCTCGTAATTTTTCCTCCTCTGT

CGAGTAA
```

> PK25433.1 | 2-C-methyl-D-erythritol 2:4-cyclodiphosphate synthase
(MDS)
(SEQ ID NO: 23)
ATGGCGGCGGCGACGGCAACACCACTCTGTGCTTCAACTCTTCCACCACACTACTCCAATACCTCCCCCA

AATCATTCAATCACTCCCATTTCACAGTCGCAGTTCCCAGAAATCTCTTCTCATCGTCCTCAATTTCATC

TCTAAGACAATCGAAAACGACGCCGCTTTCGGCTCTGCCTTCTGTATCGGCCGCCGCGACCACCGCTTTG

AACGCTGAGCAAGCTCCGTCTGAGGTATCTGCTACTCCCTCAAAGGCTCTTCCTTTTCGGGTTGGTCATG

GGTTTGACCTTCATCGATTGGAGCCTGGGTATCCTTTGATAATTGGAGGTATTAATATACCTCATGAGAA

AGGTTGCGAAGCTCATTCTGATGGGGATGTTTTGCTTCATTGTGTAGTTGATGCTATTTTGGGTGCTTTG

GGGCTTCCTGATATTGGTCAATTTTCCCTGATTCTGATCCCAAATGGAAAGGGGCTGCATCATCAGTTT

TCATCAAAGAAGCTGTGAGACTGATGCATGAGGCAGGTTATGAGCTTGGAAATTTAGATGCAACATTAAT

TCTTCAAAGACCAAAGTTAAGTCCACACAAGGAAGCTATCAGAGCCAACTTGTCTGAACTTCTAGGAGCT

GACCCTGCAGTTGTTAATCTGAAAGCGAAAACTCACGAAAAGGTCGATAGTCTCGGGGAAAATCGAAGCA

TCGCTGCTCACACTGTGGTTCTTCTTATGAAAAAATAG

> PK23068.1 | 4-hydroxy-3-methylbut-2-en-1-yl diphosphate synthase (HDS)
(SEQ ID NO: 24)
ATGGCTTCTGGAGCTGTACCAGCATCAATTTCATGTCTGAAAAGCAGAGACTCTGGCTTGAGCTTTGCTA

AAAGTTCTGATTTTGTGAGGCTTTCTGATTTAAAGAGGGTTGGTTCATCTAGAACAAGAGTTTCAGTTAT

CCGAAATTCGAATCCTGGTTCAGATATTGCTGAACTTCAGCCTGCATCAAAAGGAAGCCCTCTATTAGTT

CCTAGACAGAAGTACTGTGAATCCTTACACAAAACTGTTAGGAGGAAAACGCGAACTGTGATGGTGGGAA

ATGTGGCTCTTGGCAGTGAGCATCCCATAAGAATTCAAACGATGACGACAAATGATACCAAGGATGTTGC

TGGAACAGTTGAAGAGGTGATGAGAATAGCTGATAAGGGAGCTGATATTGTTCGGATAACAGTTCAGGGA

AGAAAAGAAGGAGATGCTTGTTTCGAAATAAAAAAATTCACTTGTGCAGAAGAATTATAATATACCTCTTG

TGGCAGATATTCATTTTGCTCCCCCAGTTGCATTAAGAGTTGCTGAATGCTTCGATAAAATTCGTGTCAA

TCCTGGAAATTTCGCTGACAGACGGGCTCAGTTTGAGACGCTCGAGTACACAGACGACGACTATCAGAAA

GAACTTGAGCATATTGAGCAGGTTTTTTCTCCATTGGTTGAGAAATGTAAGAAATATGGTAGAGCAATGC

GTATCGGGACAAACCATGGGAGTCTTTCAGATCGTATCATGAGCTACTATGGAGATTCTCCAAGGGGAAT

GGTTGAATCTGCATTTGAGTTTGCAAGGATTTGCCGGAAGTTGGATTTCCATAATTTTGTGTTTTCGATG

AAAGCAAGCAACCCAGTTGTCATGGTTCAGGCGTATCGTCTACTTGTTGCTGAAATGTATGTCCAGGGCT

GGGACTATCCACTTCACTTGGGAGTTACTGAAGCGGGAGAAGGTGAGGATGGACGAATGAAATCTGCAAT

TGGCATCGGGACCCTTCTTCAGGATGGTTTGGGTGATACTATCAGGGTTTCACTCACCGAACCGCCCGAG

GAGGAGATTGATCCCTGCAGARGGTTGGCCAATTTGGGTACAAAAGGAGCTGATCTTCAGCAAGGAGTGG

CTCCATTTGAAGAGAAGCACAGGCATTATTTTGATTTTCAACGACGAACTGGTCAACTGCCTCTACAGAA

GGAGGGCGATGAGGTTGACTATAGAGGTGCTCTGCACCGTGATGGTTCTGTTCTCATGTCAGTGTCTCTC

AATAACTTAAAGATGCCCGAGCTCCTATACAGGTCACTAGGAGCAAAGCTTGTCGTCGGGATGCCATTTA

AGGATCTGGCAACAGTAGACTCCATCTTATTGAGACAACTTCCACCTATTGACGATGACAACGCTCGATT

AGCTCTCAAAAGATTGATAGACATAAGTATGGGGTCATAACTCCTTTGTCGGAGCAGCTAACAAAGCCA

TTGCCAAATGCTATGGTTTTGGTAAATCTTAAGGAGTTATCATCTGGTGCACACAAGCTTTTGCCAGPAG

GCACGCGTTTGGTTGTATCCTTGCGCGGTGATGAACCTTACGAAGAACTGGAGATTCTCAAAGGGGTTGA

TGATGTTGTTATGATTCTTCATGATCTTCCGTTCGATGAACATAAAATTAGCAGAGTCCACTCAGCAAGA

AGATTATTTGAGTATCTATCAGATAATTCTCTTAACTTTCCTGTAATACACCACATTCAATTTCCAAATG

GAATCCACAGGGATGACTTAGTCATCGGTGCAGGTAGCAACGCTGGTGCCCTTTTAGTAGATGGACTCGG

GGACGGTATCCTCTTAGAAGCCCCAGATCAGGATTTCGATTTTCTTAGAAATACTTCTTTCAACCTACTT

-continued

```
CAAGGTTGTAGAATGCGAAATACAAAGACGGAGTATGTCTCGTGCCCATCCTGCGGTAGAACTTTGTTTG

ACCTTCAAGAAATCAGCGCAGAGATTCGAGAGAAGACATCACACCTGCCCGGTGTCTCAATTGCAATCAT

GGGTTGCATTGTTAATGGACCCGGAGAGATGGCTGATGCAGACTTCGGTTATGTCGGTGGTGCTCCCGGA

AAGATTGACCTTTATGTTGGAAAGACGGTAGTGCAGCGTGGAATCGCAATGGAACAAGCGACCGATGCAT

TGATTCAGCTAATAAAAGATCATGGCCGATGGGTTGAACCACCCTCGGACGAAGAATGA
```

> PK13726.1 | 4-hydroxy-3-methylbut-2-enyl diphosphate reductase (HDR)

(SEQ ID NO: 25)

```
ATGTCGATCACTTTCCAGCTCTGCCGGATTCCAATCCGTACCGACCTCGCCTTGGCGGAGCCTCTCTCCG

TAACCGGAACCCTCCGCTGCCGGAAACCTTTCGTCATCCGATGCGCCGGCGAGTCATCTTCAACGGCAGC

AGATTCTGATTTCGATGCGAAAGTGTTCCGTAAGAACTTGGTCCGAAGCAAGAACTACAATCGGAAAGGT

TTTGGCCATAAGGAAGAGACCCTTCAACTCATGGACAGCGAGTACACCAGTGATATTATAAAGACTTTGA

AGGATAATGGAAATGAGTACAGGTGGGGGAACGTGACGGTAAAATTGGCCGAAGCATATGGGTTTTGCTG

GGGTGTGGAGCGAGCTGTCCAAATTGCTTACGAAGCAAGGAAACAGTTCCCCGAAGAAAAGATTTGGATT

ACAAACGAAATTATTCATAATCCGACAGTCAACAAGAGACTAGAGGAAATGAAAGTGGAAAATATTCCAA

TTGATGAAGGGAGGAAACAATTTGAGATTGTAAACAAGGGTGATGTTGTGATATTGCCTGCTTTTGGTGC

TGGAGTGGATGAGATGTTGGCTTTGAGTGATAGGAATGTTCAAATTGTTGATACCACATGCCCATGGGTT

TCCAAGGTTTGGAATACAGTCGAGAAACATAAGAAAGGTGAATACACTTCCATTATTCATGGTAAATATG

CTCATGAGGAGACTATAGCTACTGCATCTTTTGCTGGAACTTACATTATTGTAAAGAACATGAAAGAGGC

AATGTATGTCTGTGATTATATTCTTGGCGGTCAACTTGATGGATCCAGCTCAACAAGAGAGGAGTTTATG

GAGAAATTTAAGAATGCAGTTTCTAAGGGATTTGATCCTGACAAACATCTTGTGAAGGCTGGTATTGCAA

ATCAGACTACAATGCTCAAGGGGGAAACCGAAGAGATTGGGAAACTGGTTGAGAGGACTATGATGCAAAA

GTACGGAGTTGAAAACATTAATGAACACTTCCAAAGCTTAACACAATTTGCGATGCAACCCAAGAGCGT

CAAGATGCAATGTACAAGATGGTGGAGGAACGTATTGACCTTATGTTAGTTGTTGGAGGATGGAACTCTA

GTAACACTTCTCATCTACAAGAGATTGCAGAGGAACGAGGTATTCCCTCGTATTGGATTGACAGTGAACA

GAGAATAGGTCCTGGAAACAAGATAGCCTACAAGCTAAATCATGGAGAGTTGGTTGAGAAAGAGAACTGG

TTACCAGAGGGTCGCATCACGGTCGGTGTAACATCAGGTGCTTCTACTCCAGATAAGGTTGTGGAAGATG

TTCTCATCAAGGTGTTTGACCTTAAGAGCGAAGAAGCTTTGCAAGTTGCTTAG
```

> AAO73863 | Carene synthase MonoTS (SEQ ID NO: 26)

```
MSVISILPLASKSCLYKSLMSSTHELKALCRPIATLGMCRRGKSVMASKSTSLTTAVSDDGVQRRIGDHH

SNLWDDNFIQSLSSPYGASSYGERAERLIGEVKEIFNSLSRTDGELVSHVDDLLQHLSMVDNVERLGIDR

HFQTEIKVSLDYVYSYWSEKGIGSGRDIVCTDLNTTALGFRILRLHGYTVEPDVFEHFKDQMGRIACSDN

HTERQISSILNLFRASLIAFPGEKVMEEAEIFSATYLKEALQTIPVSSLSQEIQYVLQYRWHSNLPRLEA

RTYIDILQENTKNQMLDVNTKKVLELAKLEFNIFHSLQQNELKSVSRWWKESGFPDLNFIRHRHVEFYTL

VSGIDMEPKHCTERLSFVKMCHLITVLDDMYDTFGTIDELRLFTAAVKRWDPSTTECLPEYMKGVYTVLY

ETVNEMAQEAQKSQGRDTLSYVRQALEAYIGAYHKEAEWISSGYLPTEDEYFENGKVSSGHRIATLQPTF

MLDIPFPHHVLQEIDFPSKFNDFACSILRLRGDTRCYQADRARGEEASCISCYMKDNPGSTQEDALNHIN

NMIEETIKKLNWELLKPDNNVPISSKKHAFDINRGLHHFYNYROGYTVASNETKNLVIKTVLEPVPM
```

>EFF14228 1-deoxy-D-xylulose-5-phosphate synthase Dxs [*Escherichia coli* B354]

(SEQ ID NO: 27)

```
  1 mmsfdiakyp tlalvdstqe lrllpkeslp klcdelrryl ldsvsrsssgh fasglgtvel 61 tvalhyvynt pfdqliwdvg hqayphkilt grrdkigtir qkgglhpfpw rgeseydvls 121 vghsstsisa gigiavaaek egknrrtvcv igdgaitagm afeamnhagd irpdmlvvln
```

```
181 dnemsisenv galnnhlaql lsgklysslr eggkkvfsgv ppikellkrt eehikgmvvp 241 gtlfeelgfn yigpvdghdv lglittlknm rdlkgpqflh imtkkgrgye paekdpitfh 301 avpkfdpssg clpkssgglp syskifgdwl cetaakdnkl maitpamreg sgmvefsrkf 361 pdryfdvaia eqhavtfaag laiggykpiv aiystflqra ydqvlhdvai qklpvlfaid 421 ragivgadgq thqgafdlsy lrcipemvim tpsdenecrq mlytgyhynd gpsavryprg 481 navgveltpl eklpigkgiv krrgeklail nfgtlmpeaa kvaeslnatl vdmrfvkpld 541 ealilemaas healvtveen aimggagsgv nevlmahrkp vpvlniglpd ffipqgtqee 601 mraelgldaa gmeakikawl a
```

>WP_072972099 2-C-methyl-D-erythritol 4-phosphate cytidylyltransferase
IspD/MCT
(SEQ ID NO: 28)
```
  1 matthldvca vvpaagfgrr mqtecpkgyl signqtileh svhallahpr vkrvviaisp 61 gdsrfaglpl anhpqitvvd ggderadsvl aglkaagdaq wvlvhdaarp clhqddlarl 121 lalsetsrtg gilaapvrdt mkraepgkna iahtvdrngl whaltpqffp rellhdcltr 181 alnegatitd easaleycgf hpqlvegrad nikitrpedl alaefyltrt ihgent
```

>WP_086589482 2-C-methyl-D-erythritol 2,4-cyclodiphosphate synthase
IspF/MDS
(SEQ ID NO: 29)
```
  1 mrighgfdvh afggegpiii ggvripyekg llahsdgdva lhaltdallg aaalgdigkl 61 fpdtdpafkg adsrellrea wrriqakgyt lgnidvtiia qapkmlphip qmrvfiaedl 121 gchmddvnvk attteklgft grgegiacea vallikatk
```

>WP_115903881 isopentenyl-diphosphate Delta-isomerase Idi
(SEQ ID NO: 30)
```
  1 mqtehvilln aqgvptgtle kyaahtadtr lhlafsswlf nakgqllvtr ralskkawpg 61 vwtnsvcghp qlgesnedav irrcryelgv eitppesiyp dfryratdps givenevcpv 121 faarttsalq inddevmdyq wcdladilhg idatpwafsp wmvmqatnre arkrlsaftq 181 lk
```

>AF513112.1 geranyl diphosphate synthase GPPS
(SEQ ID NO: 31)
MAYSAMATMGYNGMAASCHTLHPTSPLKPFHGASTSLEAFNGEHMGLLRGYSKRKLSSYKNPASRSSNATVAQLLNP

PQKGKKAVEFDFNKYMDSKAMTVNEALNKAIPLRYPQKIYESMRYSLLAGGKRVRPVLCIAACELVGGTEELAIPTA

CAIEMIHTMSLMHDDLPCIDNDDLRRGKPTNHKIFGEDTAVTAGNALHSYAFEHIAVSTSKTVGADRILRMVSELGR

ATGSEGVMGGQMVDIASEGDPSIDLQTLEWIHIHKTAMLLECSVVCGAIIGGASEIVIERARRYARCVGLLFQVVDD

ILDVTKSSDELGKTAGKDLISDKATYPKLMGLEKAKEFSDELLNRAKGELSCFDPVKAAPLLGLADYVAFRQN

>WP_053287215 geranyl transferase IspA
(SEQ ID NO: 32)
```
  1 mdfpqqleac vkqanqalsr fiaplpfqnt pvvetmqyga llggkrlrpf lvyatghmfg 61 istntldapa aavecihays lihddlpamd dddlrrglpt chvkfgeana ilagdalqtl 121 afsilsdadm pevsdrdris miselasasg iagmcggqal dldaegkhvp ldalerihrh 181 ktgaliraav rlgalsagdk grralpvldk yaesiglafq vqddildvvg dtatlgkrqg 241 adqqlgksty pallgleqar kkardlidda rqslkqlaeq sldtsaleal adyiiqrnk
```

>NP_414715 1-deoxy-D-xylulose 5-phosphate reductoisomerase IspC/DXR
(SEQ ID NO: 33)
```
  1 mkqltilgst gsigcstldv vrhnpehfrv valvagknvt rmveqclefs pryavmddea 61 saklkltmlq qqgsrtevls gqqaacdmaa ledvdqvmaa ivgaagllpt laairagkti 121 llankeslvt cgrlfmdavk qskaqllpvd sehnaifqsl pqpiqhnlgy adleqngvvs 181 illtgsggpf retplrdlat mtpdqacrhp nwsmgrkisv dsatmmnkgl eyiearwlfn 241 asasqmevli hpqsvihsmv ryqdgsvlaq lgepdmrtpi ahtmawpnrv nsgvkpldfc
```

-continued

```
301 klsaltfaap dydrypclkl ameafeqgqa attalnaane itvaaflaqq irftdiaaln 361 lsvlekmdmr epqcvddvls vdanarevar kevmrlas
```

\>EGT67781 4-diphosphocytidyl-2-C-methylerythritol kinase IspE/CMK (SEQ ID NO: 34)

```
  1 mrtqwpspak lnlflyitgq radgyhtlqt lfqfldygdt isielrddgd irlltpvegv 61 ehednlivra arlliktaad sgrlptgsga nisidkrlpm ggglgggssn aatvlvalny 121 lwqcglsmde laemgltlga dvpvfvrgha afaegvgeil tpvdppekwy lvahpgvsip 181 tpvifkdpel prntpkrsie tllkcefsnd ceviarkrfr evdavlswll eyapsrltgt 241 gacvfaefdt esearqvleq apewlngfva kgvnlsplhr aml
```

\>ANK02812 4-hydroxy-3-methylbut-2-en-1-yl diphosphate synthase IspG/HDS (SEQ ID NO: 35)

```
  1 mhnqapiqrr kstriyvgnv pigdgapiav qsmtntrttd veatvnqika lervgadivr 61 vsvptmdaae afklikqqvn vplvadihfd yrialkvaey gvdclrinpg nigneerirm 121 vvdcardkni pirigvnags lekdlgekyg eptpqalles amrhvdhldr lnfdqfkvsv 181 kasdvflave syrllakqid qplhlgitea ggarsgavks aiglglllse gigdtlrvsl 241 aadpveeikv gfdilkslri rsrginfiac ptcsrqefdv igtvnaleqr lediitpmdv 301 siigcvvngp gealvstlgv tggnkksgly edgvrkdrld nndmidqlea rirakasqld 361 earridvqqv ek
```

\>AAL38655 4-hydroxy-3-methylbut-2-enyl diphosphate reductase IspH/HDR (SEQ ID NO: 36)

```
  1 mqillanprg fcagvdrais ivenalaiyg apiyvrhevv hnryvvdslr ergaifieqi 61 sevpdgaili fsahgvsqav rneaksrdlt vfdatcplvt kvhmevaras rrgeesilig 121 haghpevegt mgqysnpegg mylvespddv wkltvkneek lsfmtqttls vddtsdvida 181 lrkrfpkivg prkddicyat tnrqeavral aeqaevvlvv gsknssnsnr laelagrmgk 241 rafliddakd iqeewvkevk cvgvtagasa pdilvqnvva rlqqlgggea iplegreeni 301 vfevpkelrv direvd
```

\>AAA24819.1 phytoene synthase CrtE (SEQ ID NO: 37)

```
  1 mvsgskagvs phreievmrq siddhlagll petdsqdivs lamregvmap gkrirpllml 61 laardlryqg smptlldlac avelthtasl mlddmpcmdn aelrrgqptt hkkfgesvai 121 lasvgllska fgliaatgdl pgerraqavn elstavgvqg lvlgqfrdln daaldrtpda 181 ilstnhlktg ilfsamlqiv aiasassspst retlhafald fgqafqlldd lrddhpetgk 241 drnkdagkst lvnrlgadaa rqklrehids adkhltfacp qggairqfmh lwfghhladw 301 spvmkia
```

\>AAA24820.1 phytoene dehydrogenase CrtI (SEQ ID NO: 38)

```
  1 mkktvvigag fgglalairl qaagiptvll eqrdkpggra yvwhdqgftf dagptvitdp 61 talealftla grrmedyvrl lpvkpfyrlc wesgktldya ndsaeleaqi tqfnprdveg 121 yrrflaysqa vfqegylrlg svpflsfrdm lragpqllkl qawqsvyqsv srfiedehlr 181 qafsfhsllv ggnpfttssi ytlihalere wgvwfpeggt galvngmvkl ftdlggeiel 241 narveelvva dnrvsqvrla dgrifdtdav asnadvvnty kkllghhpvg qkraaalerk 301 smsnslfvly fglnqphsql ahhticfgpr yrelideift gsaladdfsl ylhspcvtdp 361 slappgcasf yvlapvphlg napldwaqeg pklrdrifdy leerympglr sqlvtqrift 421 padfhdtlda hlgsafsiep lltqsawfrp hnrdsdianl ylvgagthpg agipgvvasa 481 kataslmied lq
```

```
>AAA24821.1 prephytoene pyrophosphate synthase [Pantoea agglomerans] CrtB
                                                                (SEQ ID NO: 39)
MSQPPLLDHATQTMANGSKSFATAAKLFDPATRRSVLMLYTWCRHCDDVIDDQTHGFASEAAAEEEATQRLARLRTL

TLAAFEGAEMQDPAFAAFQEVALTHGITPRMALDHLDGFAMDVAQTRYVTFEDTLRYCYHVAGVVGLMMARVMGVRD

ERVLDRACDLGLAFQLTNIARDIIDDAAIDRCYLPAEWLQDAGLTPENYAARENRAALARVAERLIDAAEPYYISSQ

AGLHDLPPRCAWAIATARSVYREIGIKVKAAGGSAWDRRQHTSKGEKIAMLMAAPGQVIRAKTTRVTPRPAGLWQRP

V

>sp|Q50L36.1|ISPS_POPAL RecName: Full = Isoprene synthase, chloroplastic;
Short = PaIspS; IspS.
                                                                (SEQ ID NO: 40)
MATELLCLHRPISLTHKLFRNPLPKVIQATPLTLKLRCSVSTENVSFTETETEARRSANYEPNSWDYDYLLSSDTDE

SIEVYKDKAKKLEAEVRREINNEKAEFLTLLELIDNVQRLGLGYRFESDIRGALDRFVSSGGFDAVTKTSLHGTALS

FRLLRQHGFEVSQEAFSGFKDQNGNFLENLKEDIKAILSLYEASFLALEGENILDEAKVFAISHLKELSEEKIGKEL

AEQVNHALELPLHRRTQRLEAVWSIEAYRKKEDANQVLLELAILDYNMIQSVYQRDLRETSRWWRRVGLATKLHFAR

DRLIESFYWAVGVAFEPQYSDCRNSVAKMFSFVTIIDDIYDVYGTLDELELFTDAVERWDVNAINDLPDYMKLCFLA

LYNTINEIAYDNLKDKGENILPYLTKAWADLCNAFLQEAKWLYNKSTPTFDDYFGNAWKSSSGPLQLVFAYFAVVQN

IKKEEIENLQRYHDTISRPSHIFRLCNDLASASAEIARGETANSVSCYMRTKGISEELATESVMNLIDETWKKMNKE

RLGGSLFAKPFVETAINLARQSHCIYHNGDAHTSPDELTRKRVLSVITEPILPFER
```

The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed.

Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein.

In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. The disclosures of all articles and references, including patent publications and the contents referred to by database (e.g., Genbank) accession numbers, are incorporated herein by reference.

---

What is claimed is:

1. An expression cassette comprising a heterologous promoter operably linked to a nucleic acid encoding a bifunctional ispDF enzyme, wherein the bifunctional ispDF enzyme comprises an amino acid sequence at least 85% identical to the amino acid sequence of SEQ ID NO: 1, SEQ ID NO: 2, or SEQ ID NO: 3, and wherein the the bifunctional ispDF enzyme has 2-C-methyl-D-erythritol 4-phosphate cyticylyltransferase activity and 2-C-methyl-D-erythritol 2,4-cyclodiphosphate synthase activity.

2. The expression cassette of claim 1, wherein the promoter operably linked to the nucleic acid encoding the bifunctional ispDF enzyme is a constitutive promoter.

3. The expression cassette of claim 1, wherein the promoter operably linked to the nucleic acid encoding the bifunctional ispDF enzyme is an inducible promoter.

4. The expression cassette of claim 1, wherein the nucleic acid encoding the bifunctional ispDF enzyme is codon optimized.

5. The expression cassette of claim 1, wherein the expression cassette further comprises a nucleic acid encoding one or more, two or more, or all of the enzymes selected from the group consisting of dxs, idi, and ispE.

6. The expression cassette of claim 1, wherein the expression cassette further comprises a nucleic acid encoding dxs and idi.

7. The expression cassette of claim 1, wherein the expression cassette further comprises a nucleic acid encoding dxs, idi, and ispE.

8. The expression cassette of claim 1, wherein the bifunctional ispDF is no more than 31% similar to the amino acid sequence of SEQ ID NO: 41.

9. A plasmid comprising the expression cassette according to claim 1.

10. The plasmid of claim 9, wherein the plasmid further comprises an expression cassette comprising a nucleic acid encoding an isoprene synthase (ispS).

11. The plasmid of claim 9, wherein the plasmid further comprises an expression cassette comprising a nucleic acid encoding a GPP synthase.

12. The plasmid of claim 11, wherein the GPP synthase is a GPP synthase derived from a eukaryote.

13. The plasmid of claim 12, wherein the GPP synthase is a plant-derived GPP synthase.

14. The plasmid of claim 12, wherein the nucleic acid encoding the GPP synthase is codon optimized.

15. The plasmid of claim 11, wherein the expression cassette comprising the nucleic acid encoding GPP synthase further comprises a nucleic acid encoding one or more components of a lycopene synthesis pathway or a monoterpene synthase.

16. The plasmid of claim 11, wherein the expression cassette comprising the nucleic acid encoding GPP synthase further comprises a nucleic acid encoding carene synthase, myrcene synthase, or limonene synthase.

17. The plasmid of claim 11, wherein the expression cassette comprising the nucleic acid encoding GPP synthase further comprises a nucleic acid encoding a cannabinoid synthase.

18. The plasmid of claim 17, wherein the cannabinoid synthase is selected from the group consisting of a Cannabis CBGA synthase, THCA synthase, CBDA synthase, and CBCA synthase.

19. A host cell comprising the expression cassette of claim 1 and/or the plasmid of claim 11.

20. A host cell comprising:
   a. an expression cassette comprising a heterologous promoter operably linked to a nucleic acid encoding a bifunctional ispDF enzyme, wherein the bifunctional ispDF enzyme comprises an amino acid sequence at least 85% identical to the amino acid sequence of SEQ ID NO: 1, SEQ ID NO: 2, or SEQ ID NO: 3, and wherein the the bifunctional ispDF enzyme has 2-C-methyl-D-erythritol 4-phosphate cyticylyltransferase activity and 2-C-methyl-D-erythritol 2,4-cyclodiphosphate synthase activity; and
   b. a expression cassette comprising a heterologous promoter operably linked to a nucleic acid encoding a terpenoid synthase.

21. The host cell of claim 20, wherein the terpenoid synthase is an isoprene synthase.

22. The host cell of claim 20, wherein the terpenoid synthase is a component of a lycopene synthesis pathway.

23. The host cell of claim 20, wherein the terpenoid synthase is a cannabinoid synthase.

24. The host cell of claim 23, wherein the cannabinoid synthase selected from the group consisting of a CBGA synthase, THCA synthase, CBDA synthase, and CBCA synthase.

25. The host cell of claim 24, wherein the cannabinoid synthase is a truncated cannabinoid synthase selected from the group consisting of a THCA synthase, CBDA synthase, and CBCA synthase, wherein the truncation is a deletion of all or part of a signal peptide.

26. The host cell of claim 20, comprising an expression cassette comprising a heterologous promoter operably linked to a nucleic acid encoding a GPP synthase.

27. The host cell of claim 20, wherein the expression cassette of a) or b) further comprises a nucleic acid encoding a GPP synthase.

28. The host cell of claim 20, wherein the host cell exhibits higher flux through the MEP pathway as compared to a control cell that does not comprise at least one of the expression cassette(s), of a. or b.

29. The host cell of claim 20, wherein the host cell does not comprise: a heterologous nucleic acid encoding ispC, ispE, ispG, or ispH; a combination thereof; or all thereof.

30. The host cell of claim 20, wherein the cell is a prokaryote.

31. The host cell of claim 20, wherein the expression cassette of a) and/or b) is integrated into the genome of the host cell.

32. The host cell of claim 20, wherein the host cell comprises a nucleic acid encoding a cannabinoid synthase operably linked to a promoter and the promoter operably linked to the nucleic acid encoding the cannabinoid synthase is a constitutive promoter.

33. The host cell of claim 20, wherein the host cell comprises a nucleic acid encoding a cannabinoid synthase operably linked to a promoter and the promoter operably linked to the nucleic acid encoding the cannabinoid synthase is an inducible promoter.

34. The host cell of claim 20, wherein the expression cassette of a) and the expression cassette of b) are present in a single plasmid or inserted into a genome of the host cell at a single locus.

35. The host cell of claim 20, wherein the expression cassette of a) and the expression cassette of b) are in different plasmids or inserted into a genome of the host cell at different loci.

36. The host cell of claim 20, wherein the host cell further comprises olivetolic acid (OA).

37. The host cell of claim 36, wherein the olivetolic acid is exogenous to the host cell.

38. The host cell of claim 20, wherein the host cell comprises an expression cassette comprising a heterologous promoter operably linked to a nucleic acid encoding one or more glycosylation pathway genes.

39. The host cell of claim 20, wherein the host cell comprises a deletion in 1, 2, 3, 4, 5, 6, or all of the genes selected from the group consisting of ackA-pta, poxB, ldhA, dld, adhE, pps, and atoDA.

40. A method of obtaining a target metabolic product, the method comprising culturing the host cell according to claim 20 in a suitable culture medium under conditions suitable to induce expression in one or more host cell expression cassettes, and then harvesting the cultured cells or spent medium, thereby obtaining the target metabolic product.

41. The method of claim 40, wherein the metabolic product is a cannabinoid.

42. The method of claim 41, wherein the cannabinoid is CBGA, THCA, CBDA, CBCA, CBN, THC, CBD, or CBC, or a mixture of one or more thereof.

43. The method of claim 40, wherein the metabolic product is a terpenoid or is isoprene.

44. The method of claim 40, wherein the method comprises harvesting and lysing the cultured cells, thereby producing cell lysate.

45. The method of claim 44, wherein the method comprises purifying the target metabolic product from the cell lysate, thereby producing a purified target metabolic product.

46. The method of claim 40, wherein the method comprises purifying the target metabolic product from the spent culture medium, thereby producing a purified target metabolic product.

47. The method of claim 45, wherein the purified target metabolic product is a cannabinoid and the method comprises formulating the cannabinoid in a pharmaceutical composition.

48. The method of claim 45, wherein the purified target metabolic product is a cannabinoid and the method comprises forming a salt, prodrug, or solvate of the purified cannabinoid.

49. The expression cassette of claim 1, wherein the bifunctional ispDF enzyme comprises an amino acid sequence at least 90% identical to the amino acid sequence of SEQ ID NO: 1, SEQ ID NO: 2, or SEQ ID NO: 3.

\* \* \* \* \*

SEQUENCE LISTING

```
<160> NUMBER OF SEQ ID NOS: 43

<210> SEQ ID NO 1
<211> LENGTH: 397
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Ile Ala Leu Gln Arg Ser Leu Ser Met His Val Thr Ala Ile Ile
1               5                   10                  15

Ala Ala Ala Gly Glu Gly Arg Arg Leu Gly Ala Pro Leu Pro Lys Gln
            20                  25                  30
```

Leu Leu Asp Ile Gly Gly Arg Ser Ile Leu Glu Arg Ser Val Met Ala
            35                  40                  45

Phe Ala Arg His Glu Arg Ile Asp Asp Val Ile Val Val Leu Pro Pro
 50                  55                  60

Ala Leu Ala Ala Ala Pro Pro Asp Trp Ile Ala Ala Ser Gly Arg Val
 65                  70                  75                  80

Pro Ala Val His Val Val Ser Gly Gly Glu Arg Arg Gln Asp Ser Val
                 85                  90                  95

Ala Asn Ala Phe Asp Arg Val Pro Ala Gln Ser Asp Val Val Leu Val
            100                 105                 110

His Asp Ala Ala Arg Pro Phe Val Thr Ala Glu Leu Ile Ser Arg Ala
            115                 120                 125

Ile Asp Gly Ala Met Gln His Gly Ala Ala Ile Val Ala Val Pro Val
130                 135                 140

Arg Asp Thr Val Lys Arg Val Asp Pro Asp Gly Glu His Pro Val Ile
145                 150                 155                 160

Thr Gly Thr Ile Pro Arg Asp Thr Ile Tyr Leu Ala Gln Thr Pro Gln
                165                 170                 175

Ala Phe Arg Arg Asp Val Leu Gly Ala Ala Val Ala Leu Gly Arg Ser
            180                 185                 190

Gly Val Ser Ala Thr Asp Glu Ala Met Leu Ala Glu Gln Ala Gly His
            195                 200                 205

Arg Val His Val Val Glu Gly Asp Pro Ala Asn Val Lys Ile Thr Thr
210                 215                 220

Ser Ala Asp Leu Asp Gln Ala Arg Gln Arg Leu Arg Ser Ala Val Ala
225                 230                 235                 240

Ala Arg Ile Gly Thr Gly Tyr Asp Leu His Arg Leu Ile Glu Gly Arg
                245                 250                 255

Pro Leu Ile Ile Gly Gly Val Ala Val Pro Cys Asp Lys Gly Ala Leu
            260                 265                 270

Gly His Ser Asp Ala Asp Val Ala Cys His Ala Val Ile Asp Ala Leu
            275                 280                 285

Leu Gly Ala Ala Gly Ala Gly Asn Val Gly Gln His Tyr Pro Asp Thr
290                 295                 300

Asp Pro Arg Trp Lys Gly Ala Ser Ser Ile Gly Leu Leu Arg Asp Ala
305                 310                 315                 320

Leu Arg Leu Val Gln Glu Arg Gly Phe Thr Val Glu Asn Val Asp Val
                325                 330                 335

Cys Val Val Leu Glu Arg Pro Lys Ile Ala Pro Phe Ile Pro Glu Ile
            340                 345                 350

Arg Ala Arg Ile Ala Gly Ala Leu Gly Ile Asp Pro Glu Arg Val Ser
            355                 360                 365

Val Lys Gly Lys Thr Asn Glu Gly Val Asp Ala Val Gly Arg Gly Glu
370                 375                 380

Ala Ile Ala Ala His Ala Val Ala Leu Leu Ser Glu Ser
385                 390                 395

<210> SEQ ID NO 2
<211> LENGTH: 407
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

```
Met Gln Val Thr Ala Ile Ile Ala Ala Gly Gly Arg Gly Arg Phe
1               5                   10                  15

Gly Gly Gly Val Pro Lys Gln Leu Val Gly Val Gly Arg Pro Ile
            20                  25                  30

Leu Glu Arg Thr Val Ala Ala Phe Leu Gly His Pro Ala Ile His Glu
        35                  40                  45

Val Val Val Ala Leu Pro Ala Glu Leu Met Ala Asp Pro Pro Ala Tyr
    50                  55                  60

Leu Arg Ala Ala Pro Lys Pro Ile Arg Leu Val Ala Gly Gly Val Gln
65                  70                  75                  80

Arg Gln Asp Ser Val Arg Gln Ala Phe Gln Ala Ala Asn Glu Gln Ser
                85                  90                  95

Asp Val Ile Val Ile His Asp Ala Ala Arg Pro Phe Ala Ser Ala Asp
            100                 105                 110

Leu Ile Ser Arg Thr Ile Ala Ala Ala Glu Gly Gly Ala Ala Leu
        115                 120                 125

Ala Ala Val Pro Ala Arg Asp Thr Val Lys Arg Gly Ala Phe Ala Ala
    130                 135                 140

Gly Arg Thr Gly Pro Ala Gly Arg Gln Ala Val Glu Gly Ala Pro Leu
145                 150                 155                 160

Leu Val Val Ala Glu Thr Leu Pro Arg Asp Ser Ile Tyr Leu Ala Gln
                165                 170                 175

Thr Pro Gln Ala Phe Arg Arg Asp Val Leu Arg Asp Ala Leu Ala Leu
            180                 185                 190

Gly Glu Ala Gly Ser Glu Ala Thr Asp Glu Ala Thr Leu Ala Glu Arg
            195                 200                 205

Ala Gly His Ile Val Arg Leu Val Glu Gly Glu Pro Ala Asn Ile Lys
        210                 215                 220

Ile Thr Thr Pro Asp Asp Leu Leu Val Ala Glu Ala Ile Ala Arg Gly
225                 230                 235                 240

Thr Gly Glu Arg Ala Val Gly Glu Arg Ala Ala Phe Arg Ile Gly Ala
                245                 250                 255

Gly Tyr Asp Leu His Arg Leu Val Glu Gly Arg Pro Leu Val Leu Gly
            260                 265                 270

Gly Val Thr Ile Pro Phe Glu Arg Gly Leu Leu Gly His Ser Asp Ala
        275                 280                 285

Asp Ala Ile Cys His Ala Val Thr Asp Ala Val Leu Gly Ala Ala Ala
    290                 295                 300

Ala Gly Asp Ile Gly Arg His Phe Pro Asp Ser Asp Pro Lys Trp Arg
305                 310                 315                 320

Asp Trp Ser Ser Ile Asp Leu Leu Arg Arg Ala Ser Ala Ile Val Lys
                325                 330                 335

Gly Arg Gly Tyr Ala Ile Ala Asn Val Asp Ala Val Ile Ala Glu
            340                 345                 350

Arg Pro Lys Leu Ala Pro Phe Leu Asp Glu Met Arg Ala Asn Val Ala
        355                 360                 365

Gly Ala Ile Gly Ile Ala Val Asp Ala Val Gly Ile Lys Gly Lys Thr
    370                 375                 380

Asn Glu Gly Leu Gly Glu Leu Gly Arg Gly Glu Ala Ile Ala Val His
385                 390                 395                 400

Ala Val Ala Leu Leu His Leu
                405
```

<210> SEQ ID NO 3
<211> LENGTH: 383
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 3

```
Met Val His Val Ser Ala Ile Ile Ala Ala Gly Gly Arg Gly Glu Arg
1               5                   10                  15

Phe Gly Gly Pro Gln Pro Lys Gln Leu Leu Leu Gly Gly Val Pro
                20                  25                  30

Ile Leu Lys Arg Thr Val Asp Ala Phe Leu Arg Gly Tyr Pro Phe Ile
            35                  40                  45

Glu Val Ile Val Ala Leu Pro Ala Glu Phe Val Ala Asn Pro Pro Asp
    50                  55                  60

Tyr Leu Asp Asp Val Ile Val Glu Gly Gly Ala Arg Arg Gln Asp
65                  70                  75                  80

Ser Val Ala Asn Ala Phe Arg Ala Val Ala Pro Ser Ala Gln Val Val
                85                  90                  95

Val Ile His Asp Ala Ala Arg Pro Leu Val Thr Pro Ser Leu Ile Glu
                100                 105                 110

Arg Thr Val Asp Ala Ala Val Lys His Gly Ala Ala Ile Ala Ala Leu
            115                 120                 125

Arg Ala Thr Asp Thr Val Lys Arg Gly Asp Ala Ser Arg Val Ile Arg
            130                 135                 140

Gly Thr Leu Pro Arg Asp Glu Ile Phe Leu Ala Gln Thr Pro Gln Ala
145                 150                 155                 160

Phe Arg Ala Gly Val Leu Arg Asp Ala Leu Ala Leu Ala Ala Ser Ala
                165                 170                 175

Ala Asp Ala Thr Asp Glu Ala Met Leu Ala Glu Gln Ala Gly His His
                180                 185                 190

Val Arg Leu Val Asp Gly Asp Pro Arg Asn Leu Lys Ile Thr Thr Pro
            195                 200                 205

Glu Asp Leu Glu Met Ala Glu Arg Leu Ile Gly Ala Arg Asn Thr Ala
    210                 215                 220

Gly Ala Met Arg Ile Gly Asn Gly Tyr Asp Leu His Arg Leu Val Thr
225                 230                 235                 240

Gly Arg Pro Leu Val Leu Gly Gly Val Thr Ile Pro Phe Glu Lys Gly
                245                 250                 255

Leu Gln Gly His Ser Asp Ala Asp Ala Val Cys His Ala Ile Thr Asp
                260                 265                 270

Ala Ile Leu Gly Ala Ala Ser Ala Gly Asp Ile Gly Arg His Phe Pro
            275                 280                 285

Asp Thr Asp Pro Ala Trp Lys Asp Ala Lys Ser Ile Val Leu Leu Gln
    290                 295                 300

Gln Ala Ala Gln Ile Val Ser Arg Ala Gly Tyr Ala Ile Ala Asn Leu
305                 310                 315                 320

Asp Val Val Ile Ala Gln Gln Pro Lys Leu Val Pro His Ile Asp
                325                 330                 335

Ala Ile Arg His Ser Val Ala His Ala Leu Gly Ile Asp Val Gln Gln
                340                 345                 350

Val Ser Val Lys Gly Lys Thr Asn Glu Gly Val Asp Ser Met Gly Ala
            355                 360                 365
```

Gly Glu Ser Ile Ala Val His Ala Val Ala Leu Leu Gln His Ser
    370                 375                 380

<210> SEQ ID NO 4
<211> LENGTH: 1638
<212> TYPE: DNA
<213> ORGANISM: Cannabis sativa

<400> SEQUENCE: 4

| | | |
|---|---|---|
| atgaattgct cagcattttc cttttggttt gtttgcaaaa taatattttt ctttctctca | 60 |
| ttccatatcc aaatttcaat agctaatcct cgagaaaact tccttaaatg cttctcaaaa | 120 |
| catattccca acaatgtagc aaatccaaaa ctcgtataca ctcaacacga ccaattgtat | 180 |
| atgtctatcc tgaattcgac aatacaaaat cttagattca tctctgatac aaccccaaaa | 240 |
| ccactcgtta ttgtcactcc ttcaaataac tcccatatcc aagcaactat tttatgctct | 300 |
| aagaaagttg gcttgcagat tcgaactcga agcggtggcc atgatgctga gggtatgtcc | 360 |
| tacatatctc aagtcccatt tgttgtagta gacttgagaa acatgcattc gatcaaaata | 420 |
| gatgttcata gccaaactgc gtgggttgaa gccggagcta cccttggaga agtttattat | 480 |
| tggatcaatg agaagaatga gaatcttagt tttcctggtg ggtattgccc tactgttggc | 540 |
| gtaggtggac actttagtgg aggaggctat ggagcattga tgcgaaatta tggccttgcg | 600 |
| gctgataata ttattgatgc acacttagtc aatgttgatg aaaagttct agatcgaaaa | 660 |
| tccatgggag aagatctgtt tgggctata cgtggtggtg gaggagaaaa ctttggaatc | 720 |
| attgcagcat ggaaaatcaa actggttgct gtcccatcaa agtctactat attcagtgtt | 780 |
| aaaaagaaca tggagataca tgggcttgtc aagttattta caaatggca aaatattgct | 840 |
| tacaagtatg acaagatt agtactcatg actcacttca taacaaagaa tattacagat | 900 |
| aatcatggga agaataagac tacagtacat ggttacttct cttcaatttt tcatggtgga | 960 |
| gtggatagtc tagtcgactt gatgaacaag agctttcctg agttgggtat taaaaaaact | 1020 |
| gattgcaaag aatttagctg gattgataca accatcttct acagtggtgt tgtaaatttt | 1080 |
| aacactgcta attttaaaaa ggaaattttg cttgatagat cagctgggaa gaagacggct | 1140 |
| ttctcaatta agttagacta tgttaagaaa ccaattccag aaactgcaat ggtcaaaatt | 1200 |
| ttggaaaaat tatatgaaga gatgtagga gctgggatgt atgtgttgta cccttacggt | 1260 |
| ggtataatgg aggagatttc agaatcagca attccattcc ctcatcgagc tggaataatg | 1320 |
| tatgaacttt ggtacactgc ttcctgggag aagcaagaag ataatgaaaa gcatataaac | 1380 |
| tgggttcgaa gtgtttataa ttttacgact ccttatgtgt cccaaaatcc aagattggcg | 1440 |
| tatctcaatt atagggacct tgatttagga aaaactaatc atgcgagtcc taataattac | 1500 |
| acacaagcac gtatttgggg tgaaaagtat tttggtaaaa attttaacag gttagttaag | 1560 |
| gtgaaaacta agttgatcc caataatttt tttagaaacg aacaaagtat cccacctctt | 1620 |
| ccaccgcatc atcattaa | 1638 |

<210> SEQ ID NO 5
<211> LENGTH: 1635
<212> TYPE: DNA
<213> ORGANISM: Cannabis sativa

<400> SEQUENCE: 5

| | | |
|---|---|---|
| atgaagtgct caacattctc cttttggttt gtttgcaaga taatattttt cttttctcca | 60 |
| ttcaatatcc aaacttccat tgctaatcct cgagaaaact tccttaaatg cttctcgcaa | 120 |

```
tatattccca ataatgcaac aaatctaaaa ctcgtataca ctcaaaacaa cccattgtat      180
atgtctgtcc taaattcgac aatacacaat cttagattca cctctgacac aaccccaaaa      240
ccacttgtta tcgtcactcc ttcacatgtc tctcatatcc aaggcactat tctatgctcc      300
aagaaagttg gcttgcagat tcgaactcga agtggtggtc atgattctga gggcatgtcc      360
tacatatctc aagtcccatt tgttatagta gacttgagaa acatgcgttc aatcaaaata      420
gatgttcata gccaaactgc atgggttgaa gccggagcta cccttggaga gtttattat       480 tgggttaatg agaaaaatga gaatcttagt ttggcggctg gtattgccc tactgtttgc       540 gcaggtggac actttggtgg aggaggctat ggaccattga tgagaaacta tggcctcgcg      600
gctgataata tcattgatgc acacttagtc aacgttcatg aaaagtgct agatcgaaaa       660 tctatggggg aagatctctt tgggctttta cgtggtggtg gagcagaaag cttcggaatc      720
attgtagcat ggaaaattag actggttgct gtcccaaagt ctactatgtt tagtgttaaa      780
aagatcatgg agatacatga gcttgtcaag ttagttaaca aatggcaaaa tattgcttac      840
aagtatgaca aagatttatt actcatgact cacttcataa ctaggaacat tacagataat      900
caagggaaga ataagacagc aatacacact tacttctctt cagttttcct tggtggagtg      960
gatagtctag tcgacttgat gaacaagagt tttcctgagt tgggtattaa aaaaacggat     1020
tgcagacaat tgagctggat tgatactatc atcttctata gtggtgttgt aaattacgac     1080
actgataatt ttaacaagga aattttgctt gatagatccg ctgggcagaa cggtgctttc     1140
aagattaagt tagactacgt taagaaacca attccagaat ctgtatttgt ccaaattttg     1200
gaaaaattat atgaagaaga tataggagct gggatgtatg cgttgtaccc ttacggtggt     1260
ataatggatg agatttcaga atcagcaatt ccattccctc atcgagctgg aatcttgtat     1320
gagttatggt acatatgtag ttgggagaag caagaagata acgaaaagca tctaaactgg     1380
attagaaata tttataactt catgactcct tatgtgtcca aaaatccaag attggcatat     1440
ctcaattata gagaccttga tataggaata aatgatccca agaatccaaa taattacaca     1500
caagcacgta tttggggtga gaagtatttt ggtaaaaatt ttgacaggct agtaaaagtg     1560
aaaaccctgg ttgatcccaa taactttttt agaaacgaac aaagcatccc acctcttcca     1620
cggcatcgtc attaa                                                      1635

<210> SEQ ID NO 6
<211> LENGTH: 1554
<212> TYPE: DNA
<213> ORGANISM: Cannabis sativa

<400> SEQUENCE: 6
atgaatcctc gagaaaactt ccttaaatgc ttctcgcaat atattcccaa taatgcaaca       60
aatctaaaac tcgtatacac tcaaaacaac ccattgtata tgtctgtcct aaattcgaca      120
atacacaatt ttagattcac ctctgacaca accccaaaac cacttgttat cgtcactcct      180
tcacatgtct ctcatatcca aggcactatt ctatgctcca agaaagttgg cttgcagatt      240
cgaactcgaa gtggtggtca tgattctgag ggcatgtcct acatatctca agtcccattt      300
gttatagtag acttgagaaa catgcgttca atcaaaatag atgttcatag ccaaactgca      360
tgggttgaag ccggagctac ccttggagaa gtttattatt gggttaatga gaaaaatgag      420
aatcttagtt tggcggctgg gtattgccct actgtttgcg caggtggaca ctttggtgga      480
ggaggctatg gaccattgat gagaaactat ggcctcgcgg ctgataatat cattgatgca      540
```

```
cacttagtca acgttcatgg aaaagtgcta gatcgaaaat ctatggggga agatctcttt    600
tgggctttac gtggtggtgg agcagaaagc ttcggaatca ttgtagcatg gaaaattaga    660
ctggttgctg tcccaaagtc tactatgttt agtgttaaaa agatcatgga gatacatgag    720
cttgtcaagt tagttaacaa atggcaaaat attgcttaca agtatgacaa agatttatta    780
ctcatgactc acttcataac taggaacatt acagataatc aagggaagaa taagacagca    840
atacacactt acttctcttc agttttcctt ggtggagtgg atagtctagt cgacttgatg    900
aacaagagtt ttcctgagtt gggtattaaa aaacggatt gcagacaatt gagctggatt     960
gatactatca tcttctatag tggtgttgta aattacgaca ctgataattt taacaaggaa    1020
attttgcttg atagatccgc tgggcagaac ggtgctttca agattaagtt agactacgtt    1080
aagaaaccaa ttccagaatc tgtatttgtc caaattttgg aaaaattata tgaagaagat    1140
ataggagctg ggatgtatgc gttgtaccct tacggtggta atggatga gatttcagaa     1200 tcagcaattc cattccctca tcgagctgga atcttgtatg agttatggta catatgtagt    1260
tgggagaagc aagaagataa cgaaaagcat ctaaactgga ttagaaatat ttataacttc    1320
atgactcctt atgtgtccaa aaatccaaga ttggcatatc tcaattatag agaccttgat    1380
ataggaataa atgatcccaa gaatccaaat aattacacac aagcacgtat ttggggtgag    1440
aagtattttg gtaaaaattt tgacaggcta gtaaaagtga aaccctggt tgatcccaat     1500 aactttttta gaaacgaaca aagcatccca cctcttccac ggcatcgtca ttaa          1554

<210> SEQ ID NO 7
<211> LENGTH: 1188
<212> TYPE: DNA
<213> ORGANISM: Cannabis sativa

<400> SEQUENCE: 7
atgggactct catcagtttg taccttttca tttcaaacta attaccatac tttattaaat     60
cctcacaata taatcccaa aacctcatta ttatgttatc gacaccccaa acaccaatt     120 aaatactctt acaataattt tccctctaaa cattgctcca ccaagagttt tcatctacaa    180
aacaaatgct cagaatcatt atcaatcgca aaaaattcca ttagggcagc tactacaaat    240
caaactgagc ctccagaatc tgataatcat tcagtagcaa ctaaaatttt aaactttggg    300
aaggcatgtt ggaaacttca agaccatat acaatcatag catttacttc atgcgcttgt     360
ggattgtttg ggaaagagtt gttgcataac acaaatttaa taagttggtc tctgatgttc    420
aaggcattct ttttttggt ggctatatta tgcattgctt cttttacaac taccatcaat     480
cagatttacg atcttcacat tgacagaata aacaagcctg atctaccact agcttcaggg    540
gaaatatcag taaacacagc ttggattatg agcataattg tggcactgtt tggattgata    600
ataactataa aaatgaaggg tggaccactc tatatatttg gctactgttt tggtattttt    660
ggtgggattg tctattctgt tccaccattt agatggaagc aaaatccttc cactgcattt    720
cttctcaatt tcctggccca tattattaca aatttcacat tttattatgc cagcagagca    780
gctcttggcc taccatttga gttgaggcct tcttttactt tcctgctagc atttatgaaa    840 tcaatggggtt cagctttggc tttaatcaaa gatgcttcag acgttgaagg cgacactaaa    900
tttggcatat caaccttggc aagtaaatat ggttccagaa acttgacatt attttgttct    960
ggaattgttc tcctatccta tgtgctgct acttgctg ggattatctg gccccaggct       1020
ttcaacagta acgtaatgtt actttctcat gcaatcttag catttggtt aatcctccag     1080 actcgagatt ttgcgttaac aaaattacgac ccggaagcag gcagaagatt ttacgagttc   1140
```

```
atgtggaagc tttattatgc tgaatatttta gtatatgttt tcatataa        1188
```

<210> SEQ ID NO 8
<211> LENGTH: 306
<212> TYPE: DNA
<213> ORGANISM: Cannabis sativa

<400> SEQUENCE: 8

```
atggcagtga agcatttgat tgtattgaag ttcaaagatg aaatcacaga agcccaaaag     60
gaagaatttt tcaagacgta tgtgaatctt gtgaatatca tcccagccat gaaagatgta    120
tactggggta agatgtgac tcaaaagaat aaggaagaag ggtacactca catagttgag    180
gtaacatttg agagtgtgga gactattcag gactacatta ttcatcctgc ccatgttgga    240
tttggagatg tctatcgttc tttctgggaa aaacttctca tttttgacta cacaccacga    300
aagtag                                                              306
```

<210> SEQ ID NO 9
<211> LENGTH: 1158
<212> TYPE: DNA
<213> ORGANISM: Cannabis sativa

<400> SEQUENCE: 9

```
atgaatcatc ttcgtgctga gggtccggcc tccgttctcg ccattggcac cgccaatccg     60
gagaacattt tattacaaga tgagtttcct gactactatt ttcgcgtcac caaaagtgaa    120
cacatgactc aactcaaaga aaagtttcga aaaatatgtg acaaaagtat gataaggaaa    180
cgtaactgtt tcttaaatga agaacaccta agcaaaacc caagattggt ggagcacgag    240
atgcaaactc tggatgcacg tcaagacatg ttggtagttg aggttccaaa acttgggaag    300
gatgcttgtg caaaggccat caagaatgg ggtcaaccca agtctaaaat cactcattta    360
atcttcacta gcgcatcaac cactgacatg cccggtgcag actaccattg cgctaagctt    420
ctcggactga gtccctcagt gaagcgtgtg atgatgtatc aactaggctg ttatggtggt    480
ggaaccgttc tacgcattgc caaggacata gcagagaata caaaggcgc acgagttctc    540
gccgtgtgtt gtgacataat ggcttgcttg tttcgtgggc cttcagagtc tgacctcgaa    600
ttactagtgg acaagctat cttttggtgat ggggctgctg cggtgattgt tggagctgaa    660
cccgatgagt cagttgggga aaggccgata tttgagttgg tgtcaactgg gcaaacaatc    720
ttaccaaaact cggaaggaac tattgggggga catataaggg aagcaggact gatatttgat    780
ttacataagg atgtgcctat gttgatctct aataatattg agaaatgttt gattgaggca    840
tttactccta ttgggattag tgattggaac tccatatttt ggattacaca cccaggtggg    900
aaagctattt ggacaaagt ggaggagaag ttgcatctaa agagtgataa gtttgtggat    960
tcacgtcatg tgctgagtga gcatgggaat atgtctagct caactgtctt gtttgttatg   1020
gatgagttga ggaagaggtc gttggaggaa gggaagtcta ccactggaga tggatttgag   1080
tggggtgttc tttttgggtt tggaccaggt ttgactgtcg aaagagtggt cgtgcgtagt   1140
gttcccatca aatattaa                                                 1158
```

<210> SEQ ID NO 10
<211> LENGTH: 2166
<212> TYPE: DNA
<213> ORGANISM: Cannabis sativa

<400> SEQUENCE: 10

```
atgggtaaga attacaagtc cctggactct gttgtggcct ctgacttcat agccctaggt      60
atcacctctg aagttgctga gacactccat ggtagactgg ccgagatcgt gtgtaattat     120
ggcgctgcca ctccccaaac atggatcaat attgccaacc atattctgtc gcctgacctc     180
cccttctccc tgcaccagat gctcttctat ggttgctata aagactttgg acctgcccct     240
cctgcttgga tacccgaccc ggagaaagta agtccacca atctgggcgc acttttggag      300
aagcgaggaa aagagttttt gggagtcaag tataaggatc ccatttcaag ctttctcat      360
ttccaagaat tttctgtaag aaaccctgag gtgtattgga gaacagtact aatggatgag     420
atgaagataa gttttcaaa ggatccagaa tgtatattgc gtagagatga tgacattaat      480
aatccagggg gtagtgaatg cttccagga ggttatctta actcagcaaa gaattgcttg      540
aatgtaaata gtaacaagaa attgaatgat acaatgattg tatggcgtga tgaaggaaat     600
gatgatttgc ctctaaacaa attgacactt gaccaattgc gtaaacgtgt ttggttagtt     660
ggttatgcac ttgaagaaat gggtttggag aagggttgtg caattgcaat tgatatgcca     720
atgcatgtgg atgctgtggt tatctatcta gctattgttc ttgcgggata tgtagttgtt     780
tctattgctg atagttttc tgctcctgaa atatcaacaa gacttcgact atcaaaagca     840
aaagccattt ttacacagga tcatattatt cgtgggaaga agcgtattcc cttatacagt     900
agagttgtgg aagccaagtc tcccatggcc attgttattc cttgtagtgg ctctaatatt     960
ggtgcagaat tgcgtgatgg cgatatttct tgggattact ttctagaaag agcaaaagag    1020
tttaaaaatt gtgaatttac tgctagagaa caaccagttg atgcctatac aaacatcctc    1080
ttctcatctg gaacaacagg ggagccaaag gcaattccat ggactcaagc aactccttta    1140
aaagcagctg cagatgggtg gagccatttg gacattagga aggtgatgt cattgtttgg     1200
cccactaatc ttggttggat gatgggtcct ggctggtct atgcttcact ccttaatggg     1260
gcttctattg ccttgtataa tggatcacca cttgtttctg gctttgccaa atttgtgcag    1320
gatgctaaag taacaatgct aggtgtggtc cctagtattg ttcgatcatg gaaaagtacc    1380
aattgtgtta gtggctatga ttggtccacc atccgttgct tttcctcttc tggtgaagca    1440
tctaatgtag atgaatacct atggttgatg gggagagcaa actacaagcc tgttatcgaa    1500
atgtgtggtg gcacagaaat tggtggtgca ttttctgctg gctcttcctt acaagctcaa    1560
tcattatctt catttagttc acaatgtatg ggttgcactt tatacatact tgacaagaat    1620
ggttatccaa tgcctaaaaa caaaccagga attggtgaat tagcgcttgg tccagtcatg    1680
tttggagcat cgaagactct gttgaatggt aatcaccatg atgtttattt taagggaatg    1740
cctacattga atggagaggt tttaaggagg catggggaca tttttgagct acatctaat     1800
ggttattatc atgcacatgg tcgtgcagat gatacaatga atattggagg catcaagatt    1860
agttccatag agattgaacg agtttgtaat gaagttgatg acagagttt cgagacaact     1920
gctattggag tgccaccttt gggcggtgga cctgagcaat tagtaatttt ctttgtatta    1980
aaagattcaa atgatacaac tattgactta aatcaattga ggttatcttt caacttgggt    2040
ttacagaaga aactaaatcc tctgttcaag gtcactcgtg ttgtgcctct ttcatcactt    2100
ccgagaacag caaccaacaa gatcatgaga agggttttgc gccaacaatt ttctcacttt    2160
gaatga                                                               2166
```

<210> SEQ ID NO 11
<211> LENGTH: 1632
<212> TYPE: DNA
<213> ORGANISM: Cannabis sativa

<400> SEQUENCE: 11

```
atggagaaat ctgggtatgg aagagacggt atttacaggt ctctgagacc acctctacac     60
ctccccaaca acaacaacct ctcaatggtt tcattccttt tcagaaactc atcttcatac    120
ccacaaaagc cagctctcat tgattccgaa accaaccaaa tactctcctt ttcccacttc    180
aaatctacgg ttatcaaggt ctcccatggc tttctcaatc tgggtatcaa gaaaaacgac    240
gtcgttctca tctacgcccc taattctatc cacttccctg tttgtttcct tggaattata    300
gcctctggag ccattgccac tacctcaaat cctctctaca cagtttccga gctttccaaa    360
caggtcaagg attccaatcc caaactcatt atcaccgttc ctcaactctt ggaaaaagta    420
aagggtttca atctccccac gattctaatt ggtcctgatt ctgaacaaga atcttctagt    480
gataaagtaa tgacctttaa cgatttggtc aacttaggtg ggtcgtctgg ctcagaattt    540
ccaattgttg atgattttaa gcagagtgac actgctgcgc tattgtactc atctggcaca    600
acgggaatga gtaaaggtgt ggttttgact cacaaaaact tcattgcctc ttctttaatg    660
gtgacaatgg agcaagacct agttggagag atggataatg tgtttctatg cttttttgcca   720
atgtttcatg tatttggttt ggctatcatc acctatgctc agttgcagag aggaaacact    780
gttatttcaa tggcgagatt tgaccttgag aagatgttaa aagatgtgga aaagtataaa    840
gttacccatt tgtgggttgt gcctcctgtg atactggctc tgagtaagaa cagtttggtg    900
aagaagttta atctttcttc tataaagtat attggctctg gtgcagctcc tttgggcaaa    960
gatttaatgg aggagtgctc taaggttgtt ccttatggta ttgttgctca gggatatggt   1020
atgacagaaa cttgtgggat tgtatccatg gaggatataa gaggaggtaa acgaaatagt   1080
ggttcagctg gaatgctggc atctggagta gaagcccaga tagttagtgt agatacactg   1140
aagcccttac ctcctaatca attggggggag atatgggtga aggggcctaa tatgatgcaa   1200
ggttacttca ataacccaca ggcaaccaag ttgactatag ataagaaagg ttgggtacat   1260
actggtgatc ttggatattt tgatgaagat ggacatctttt atgttgttga ccgtataaaa   1320
gagctcatca aatataaagg attttcaggtt gctcctgctg agcttgaagg attgcttgtt   1380
tctcaccctg aaatactcga tgctgttgtg atcccatttc ctgatgctga agcgggtgaa   1440
gtcccagttg cttatgttgt gcgctctccc aacagttcat taaccgaaaa tgatgtgaag   1500
aaatttatcg cgggccaggt tgcatctttc aaaagattga gaaagtaac atttataaac    1560
agtgtcccga atctgcttc ggggaaaatc ctcagaagag aactcattca gaaagtacgc    1620
tccaacatgt ga                                                       1632
```

<210> SEQ ID NO 12
<211> LENGTH: 1458
<212> TYPE: DNA
<213> ORGANISM: Cannabis sativa

<400> SEQUENCE: 12

```
atgtctttta tgatgagcat gaatccttct ccctcctcgc caccgccacc gttatcgtcg     60
ccgtcggaat cttcctcaac gccgtcaaca ctgccagtcc gtacgatccc gggaagctac    120
ggatggccgt tactggggcc catctcggac cggttagact acttctggtt ccaaggccca    180
gatacgtttt tcagaaaaag agtagagaaa tacaagagca cagtgttccg taccaacata    240
ccccgacct ttccttttctt cagcgttaat ccgaacattg tggccgtgct ggactgtaaa    300
tcattttctc atcttttcga catggaaatt gtcgagaaaa agaatgttct tgttggagat    360
```

```
ttcatgccca gtgtcaatta cactggtgat attagggttg gagcttatct cgacacttct    420
gaaccacaac acgctaaggt taagaacttc gcaatggatg tactaaaaca aagctcgaag    480
atatgggtgg gagaactgac atcaaatctg tcgacgatgt gggacacaat agaaaaagac    540
gtatctgaga aatcatcctc atcctactta gccccacttc aaaagttctt gttcaacttc    600
ctggtcaagt gtctaattgg tgctgaccct tccaactccc ccaagattgc agagtctggc    660
tacatcatgc tcgaccgatg gttagccttc cagctcctcc ccactatcaa gattgggatc    720
cttcagcctc ttgaggagct tttcattcac tcttttgcct atcctttttt cttggtcagt    780
ggtgactaca ataacctctc cagttttgta gaggaatatg gtaaagaaat agtagcgaga    840
ggtgaaaccg agttcgggct gagtaaacaa gaagcgattc acaaccttct cttcattttg    900
ggtttcaacg ccttcggggg attctctata tttctaccga gcctactggg caccgtggcg    960
agtgacacaa ccgatctaca acaaagactg gtcaaagaag tcagacaaaa tggcgggtca   1020
actctgacgt ttgactcgat caaagaaatg ccactcgttc aatcggtcgt gtacgagact   1080
ctccggctca atccacctgt tccgctccaa ttcgccaggg ccaggaagga cttccggctc   1140
agctcgcacg acgcggcctt cgaggtgaag aaaggcgagc tcctatgcgg gtttcaaagc   1200
cttgttatga gggacccaaa atattctcg gaaccggagt cgttcattgg ggaccggttc   1260
atgaaagata aggtctctt agattatctt tactggtcca atggacctca aaccggtgtg   1320
cccagcgtca ccaataagca atgcgcggga aaagatatcg tcacgcttac ggcttgtttg   1380
atcttggctt acaccttccg tcgttatgac tccatcagcg ggagctcaag ttcaatcaca   1440
gcccttaaaa aggcttaa                                                 1458

<210> SEQ ID NO 13
<211> LENGTH: 2787
<212> TYPE: DNA
<213> ORGANISM: Cannabis sativa

<400> SEQUENCE: 13
atgttgaagc tcctcatca gtagttcaa aatttgaaat atgagaaaac cctagttctt       60
ttgaacaagc cattcatcca tggctacaac ggggctatta tcgtgtcaa ctctcggcta     120 tttccagtaa aacctaaaac caaaagacga gtcgcttcat catcatcatc atcatctccc    180
ggaaccaaaa acattattaa agcttcttta ttttctccaa tggagaagaa gaatacagct    240
agggtttcgg ttagtgtggc ggtacaacgt gtgactccaa agttttggag atttgaattg    300
tctgagaaaa tccaagatgg acgtgatagg cttgaggatc ttctagggct aaactcttta    360
agtattgagc ttgttagtac tcaaaaagat ccagtaacgg ggaaagagcg aacggttaaa    420
ggttttccaa aaaggcccaa ctttaacata ttttcatcaa gtgatgtaaa atacgaagcg    480
aaatttgaca taccaaaaga ttttggagaa gtgggtgcta taatcgtcga aatgattttt    540
gaaagagaaa tatttttaaa gaatattata ctcgaagact tgccctccga accaagcacc    600
cttgaattct cttgcaactc gtgggttcag tccaaacatg atgtccctac tgatcaacac    660
aagagagtct tcttctctaa taagtgttac ctaccatcac aaacaccaag tgggataaaa    720
gaattgagaa aaaattgcatt ggaaaatttg agaagatg aaaaggaga gaggaagaag    780 aatgaaagag tttatgatta tgatgtgtat aatgatcttg acaaccgga caacaatgat    840 gacctaaaaa gacctattct tggcggatca aagaattcc cttatcctag gcgttgtaga    900 accgacggc ctccaactga aactgatcca ttatctgagt caaggattag tgattttta    960 gtaccaagag atgaagaatt tgcagaagtg aagcaaagta attttagttt gaagactgta   1020
```

```
tactcagtaa tacatgcagt gattcccata ctcagacaag tcttaattga tgaaaatttc      1080
ccatacttca ctgccattga tgttctctat gatgaaggca ttaaaatccc ttctaatgct      1140
gaaaagacct taattcaaac catcaaaaat gtcaatgcaa gaatatacaa aactgtttct      1200
gatgctgatg atttttttaca gtttcagcag cctccaacca tggacaagga caaattcttc     1260
tggtttagag atgaagagtt ttgtagacaa actattgccg gtctcaaccc ttgctgcatt      1320
gaattggtta aggagtggcc tttgaaaagt gaacttgacc ccacaatcta tggcccacca      1380
gagtcaaaaa tcaccacaga attggttgag aaattcatca agtatatgg ctacaataat       1440 attaatgagg ctttaaaaga aaaaaaattg ttcatgttgg attaccatga tgtattatta      1500
ccatatgtta gcaaagtaag ggaactggaa ataaaaacct tgtatggatc aagaacactt      1560
tttttcttga ctccttatgg tacattgttg cctttggcca ttgaattgat tcggccaccg      1620
atggatggta agccgcaatg gaaggaagtc tacaccccga tgaattggca ttctaccgat      1680
ctttggcttt ggagactcgc aaaagctcat gtccttgctc atgattccgg tgttcatcaa      1740
ctcgttagtc actggctaag aacacattgt gcagttgagc catatataat tgcaacaaat      1800
agacaattga gtgcaatgca tcctatccat agattattga agccacattt tagatacaca      1860
atggagatta atgctcttgc tcgagaaagt ttgatcaatg caggtggtat catcgaaaca      1920
gcatttgcac ctggaaaata ttctatggag ttaagctccg tcatgtacga caaacaatgg      1980
cgattcgatc tacaagcatt gccagctgac ctaattcata gaggaatggc tgttgaggac      2040
aaggatagtg aacatggtgt aagagtaata attgaagatt acccttacgc caacgacggt      2100
cttctcatat ggagctccat caaacaatgg gttactgact acgtcaacca ctactaccct      2160
acctccagtg aggtagagcg cgacgaagaa ttacaagcat ggtggacaga gatcagaact      2220
gtaggtcacg ctgacaagaa agacgcacct gggtggcctg acttaaaaac gaaacaagat      2280
ctcatagaca ttgtcacaaa catggcatgg acagcatcag ctcaccatgc agctgtcaac      2340
tttggacaat atgcttacgc tggctatttc cctaaccgac caaccataac aagaactgtt      2400
atgccgtcag aagagaagga gtataaccta gatgcgtgga acacttcaa aaatagtcct       2460 gaagacgccc ttttgaagtg cttacctacg caattacaag caggcctagt tgtggccgtg      2520
ttagacgtgt tgtctactca ctcgccagac gaagagtatc ttggagacaa gatggaaccc      2580
tcgtggggct cgaatcttgt tatagcggaa gcttttaatc ggttcaataa gaggatgaac      2640
gagattgaaa gtatcattaa tgaaaagaat gataatgaga atttaaggaa tagacatgga      2700
gctggaattt tgtcttatga acttctcaag ccctttttctg agcctggtgt cactaacaag      2760
ggtattccat atagcatatc tatttga                                          2787
```

<210> SEQ ID NO 14
<211> LENGTH: 1134
<212> TYPE: DNA
<213> ORGANISM: Cannabis sativa

<400> SEQUENCE: 14

```
atgggagccg gtggcaaaaa tagtagactt gagcgagcac cacacaccac accaccattc       60
acactaagcc aactcaagaa agccattcca ccccattgct tcaaccattc tcttcttcgt      120
tccttctctc atgtccttca agaccttttt ttctcctttt tgttctacta catagcaacc      180
tcttacttcc atcttctccc acacccgctc caatacttag cttggccact ttattggatc      240
ttccaaggca gcattttttgc tggtatttgg gtccttggtc atgattgtgg tcaccaagct      300
```

```
ttcagtgacc accaatgggt ggatgacacc gttggctttg tcctccactc cgctcttctc    360
ttcccatact tctcttttaa gtatagtcat cgtcgccatc attcaaacat cggctccctt    420
gaacatgatc aattgtttgt tccagtcccc gaatctcaaa tcgcatggct ctacaaacgt    480
tacttggaca atccactagg aagagcccta aagctttcca ctatagtgtt ccttggtttt    540
cctttgtact taggtttcaa tcttacaggc aaaccatatg atcgttatgc atgtcattat    600
gatccttact ctccactcta ctcaaaaagt gaaaggcttc atatattgat ttcagatatc    660
ggtgttttca tcaccacatt agtgttatac cagcttggct cgactaaagg gttgagttgg    720
cttgtgttca tgtatggggt gccattgttt cagggaata gcatccttgt gacaatcgca     780
tacttgaatc atactcaccc ttcattgcct cattatgact cgtcagagtg ggattggttg    840
aaaggagcat tgtcaacaac tgatcgaaac tatggatcaa ttctcaatag gttttccat     900
caccttacag atgctcatat ggcacaccat ttattcgcaa caatacctca ctaccatgca    960
aatgaagcca ccaaagttat caaatccata ttgggagaat actactcttt tgatgatact   1020
ccaataatta aagctctttg gagagagact aaggagtgtg tctatattga ccaaatcat    1080
gaatcttctc ctaataataa caaaggtgtt ttctggtaca acaacaagtt ctga         1134
```

<210> SEQ ID NO 15
<211> LENGTH: 1113
<212> TYPE: DNA
<213> ORGANISM: Cannabis sativa

<400> SEQUENCE: 15

```
atgagcactg taaatctcac atgggttcaa acctgttcca tgttcaacca aggaggtaga     60
tccagatcct tatcaacttt caatctcaat ctctaccacc ctttgaaaaa acacccttt    120
tcaatccaaa ccccaaaaca aaaacgaccc acttcaccat tttcatcaat ctcagctgtt    180
ctaaccgagc aagaagccgt taagaaggc gatgaagaaa atccatctt caatttcaag     240
tcttacatgg tccaaaaagc caactcagtc aaccaagctt tagactcagc cgttttgctc    300
agagatccca ttatgataca cgagtccatg cgttactcac tcctcgccgg aggaaaacga    360
gtcagaccca tgctctgtct ctcagcctgt gaactcgtag gcggaaaaga tccgtagcc    420
atgccggctg cctgcgccgt cgaaatgatc cacaccatgt ctctaatcca cgacgacctc    480
ccttgtatgg acaacgatga cctccgccgt ggaaagccca caaaccacaa agtcttcgga    540
gaagacgtgg ccgttttagc cggcgatgca cttttagcct tgcttttga gcacatggcg    600
gtctctaccg ttggtgttcc ggcagccaag attgtcaggg cgattggtga gcttgctaag    660
tcaattgggt cagaaggatt agtggctggt caagtggttg atattgattc agagggtttg   720
gctaatgttg ggcttgaaca acttgagttc attcatctcc ataagactgg ggctcttcta    780
gaagcttctg ttgttttggg ggctattctt ggtggtggta cagatgaaga agttgaaaaa    840
cttaggagct ttgctaggtg tattggcttg ctttttcagg ttgttgatga cattcttgat    900
gtgactaaat cttctcaaga attgggtaaa actgctggga agatttggt ggctgataag    960
gttacttatc caaggctaat gggtattgac aaatcaagag aatttgctga gcaattgaac   1020
acagaagcca acagcatct ttctggtttt gatcccataa aggctgctcc tttaattgct   1080
ttggctaatt atattgctta taggcaaaat tga                                1113
```

<210> SEQ ID NO 16
<211> LENGTH: 948
<212> TYPE: DNA
<213> ORGANISM: Cannabis sativa

<400> SEQUENCE: 16

```
atggcggttt ataatctatc aattaattgc agtccaagat tgttcatca tgtttacgtt      60
ccacatttca catgtaaatc caataagtcg ttaagtcacg tacccatgag aataaccatg     120
tccaaacagc atcatcattc ttattttgcc tccacaacag ccgatgtaga tgcccatctc    180
aagcaatcca tcactatcaa gccaccactc tcagttcacg aggccatgta caatttcatc    240
ttttccacac ctccgaattt agcaccgtca ttgtgcgtgg cggcgtgtga gcttgtcggg    300
ggccaccagg accaggccat ggcagcagcc tccgccttgc gcgtcatcca cgcagccatc    360
ttcactcatg accacctccc tttaacgggc aggcccaatc caacaagtcc tgaggcagcg    420
acccacaatt cttacaaccc aaatattcag ctccttctcc cggacgcaat tgtacctttt    480
gggttcgaat tgttggccaa ttctgatgac cttacccata taaatcaga tcggattttg     540
cgggtcattg tagagttcac acgcacctt ggatcacgag aactattga tgctcaatac      600
catgagaagc tagccagtag atttgacgtt gatagtcatg aagccaaaac tgtcgggtgg    660
ggccattatc cctctttgaa gaaggaaggt gcgatgcatg catgcgctgc tgcatgtggg    720
gccattcttg gagaggcaca tgaagaagag gttgagaagt tgagaacttt tggtctttat    780
gtgggcatga ttcaaggata tgccaataga tttataatga gcagcacaga agaaaagaaa   840
gaagcagata gaatcatcga ggagttaacc aatttggctc gccaggaact aaaatatttc   900
gatgggagaa acttagagcc attttcaacc tttctttttc gtctatag                948
```

<210> SEQ ID NO 17
<211> LENGTH: 705
<212> TYPE: DNA
<213> ORGANISM: Cannabis sativa

<400> SEQUENCE: 17

```
atgggagact ctgccgacgc tggaatggac gctgtccaga gacgccttat gtttgatgat     60
gaatgcattc tagtggatga gaatgaccga gttgttggtc atgatacaaa atataactgt    120
cacttgatgg aaaagattga aaaggataat ttgctacaca gggctttcag tgtgttcttg    180
ttcaactcaa aatatgagtt gcttcttcag caacgttctg caacaaaggt aacattccct    240
cttgtgtgga caaacacctg ttgtagccac ccgctctacc gtgaatctga gcttatcgat    300
gaggagtccc ttggagcaag gaatgcagca cagagaaagc ttttagatga gctgggtatt    360
cctgctgaag atgtgccagt tgatcaattt accccactag gcaggatgct gtacaaagct    420
ccttctgatg gcaaatgggg cgagcatgaa cttgattacc tgctcttcat cgtccgggat    480
gttagtgtca atccaaatcc agatgaagta gctgatatca agtatgtaaa ccgggacgag    540
ttgaaagagt tgttgaggaa agcagatgct ggggaaggag gcttgaagct atccccttgg    600
ttcagactgg ttgtggataa tttcttgttc aagtggtggg accatgttga gaaaggcaca    660
cttaaggaag ttgctgatat gaaaaccatt cacaagttga cttaa                    705
```

<210> SEQ ID NO 18
<211> LENGTH: 2157
<212> TYPE: DNA
<213> ORGANISM: Cannabis sativa

<400> SEQUENCE: 18

```
atggcgtttt gtgcattatc atttcctgct catattagcc gggcaactac accagcacct     60
tcagatcttc acaaatctag ttcttttctct tctcggtttt attggggagc agatctgctg   120
```

```
aggccatctc aatacaaggt caggaaaata caaagtgggg tttatgcatc actgtcagaa        180
agtggagaat atcactcaag gagaccacca actcctctct tggacaccat aaattatcca        240
attcatatga aaaatctctc tgttaaggag cttaaacaac tatcagatga actaaggtct        300
gatgtcatct tcaacgtttc taacaccggg ggtcacctgg gctcaagcct tggtgttgtt        360
gagcttactg tggctcttca ttttgtcttc aatactcctc aggataggat actatgggat        420
gttggtcatc agtcttaccc tcataaaatt ctgactggaa gaagagataa gatgcacacc        480
atgaggcaga ccaacgggtt agccggattc actaagcggt ctgagagtga atatgattgt        540
tttgggactg gtcatagttc taccaccatc tcagctggct tgggaatggc tgttggaagg        600
gatcttaaag gaagaaagaa taatgttgtg gctgtcatag gtgatggtgc catgacagca        660
ggtcaagctt atgaagccat gaataatgcc gggtaccttg attccgacat gattattatt        720
cttaacgaca ataaacaggt ttctttacct actgcctctc ttgatgggcc cataccacct        780
gttggagctt tgagtagtgc ctctcagtagg ctgcaatcaa acaggcctct tagagaacta        840
agagaagtag ccaagggagt tactaaacaa ataggtggat cagtacatga attggctgca        900
aaagttgatg aatatgctcg tggaatgata agtggtctg gctcaacatt gtttgaggag        960
cttggactct attatattgg tccagttgat ggtcacaata tagatgatct tgtttccata       1020
ctagaggagg ttaagagcac taaaacaaca ggtccagtct tgatccattg catcactgag       1080
aaaggaagag gatatccata tgcagagaaa gctgctgata gtatcatgg ggtggccaag        1140 tttgatccag caactggaaa gcaattcaaa ggcacttcta acacacagtc atacactaca       1200
tactttgctg aggctttggt tgcagaagca gaggcagaca agatgttgt ggccatccat         1260 gctgcaatgg gtggtggaac aggcttgaat ctcttcctc gccgttttcc aacaagatgt         1320
tttgatgttg ggatagcaga acagcatgct gttactttcg ctgctggttt ggcttgcgag       1380
ggccttaagc cgttttgtgc aatttactca tctttcatgc agcgagccta tgatcaggta       1440
gtacatgatg ttgatttgca gaagttgccg gtgagatttg caatggacag agctggactt       1500
gttggggccg acggccctac acattgtggt gcttttgatg ttactttcat ggcatgcctc        1560
ccaaacatgt tgtgatggc tccttccgat gaggcagagc tcttccacat ggttgccacc        1620
gctgctgcca tagatgacag accaagttgt ttccgttacc ccagaggaaa tggaattggt       1680
gttccattac ctcaagggaa taaaggaact cctcttgaga tcggaaaagg cagggtattg       1740
gttgaagggg aaagagtagc acttctaggc tatggaacag cagttcagag ttgtttggct       1800
gctgcagcct tagtagaacc tcacggtcta cggctaacag ttgctgatgc acgattttgc       1860
aagcctttgg atcatgccct cattcgcgaa ctagcgaaaa atcacgaggt tttgattaca       1920
gtggaagaag gatctatagg aggttttgga tctcatgttg ctcagtttat ggcccttgat       1980
ggccttcttg atggaaaaac aaagtggaga ccaattgttc ttcctgaccg atacatcgac       2040
cacggttcgc ctgctgatca atatgtcgac gcgggtctca cgccacctca cattgcagcc       2100
acagttttca atgtactagg acaaacaaga gaggccttga aggttatgac aacatga          2157

<210> SEQ ID NO 19
<211> LENGTH: 2142
<212> TYPE: DNA
<213> ORGANISM: Cannabis sativa

<400> SEQUENCE: 19
atggcggttt ctggttcatt cattgtacca aatcattcat tcctttcaca acttaaatct         60
ccacagccat attacagttc caacaaacag ttgagtttaa gggtgagagg atctctttgt        120
```

```
agctcagatg atggggaagg aaaattcatc agcaaagaaa aagatgaatg gaaaatcaag        180
tattccagtg aaaaaccaat cactccattg cttgatacag tcaattaccc agttcacatg        240
aagaatttat ccacacagga tcttgaacag ctagcagcag agcttagagc agatgtagtc        300
catacagtat caaaaacagg tggtcatctg agtgcaagct ggggagttgt ggagctcact        360
gtagcactgc atcatgtttt caatacccct gatgataaaa tcatatggga tgttggacat        420
cagacatacc cgcataagat tcttacagga aggaggtctc aaatgcatac cattagaaag        480
acttctggtc tagcagggtt tcccaaaaga gatgagagtg tttacgatgc tttcggtgca        540
ggtcacagtt ctacaagcat atcagcaggc cttggcatgg cagttgccag ggatcttctg        600
ggaaagaaga acagtgttgt ttctgtgatt ggagatgggg ccatgactgc aggaatggca        660
tatgaagcca tgaataatgc cggctacttg gacgccaact tgattgttgt attaaacgac        720
aataaacaag tttctttacc aactgctact cttgatggtc ctgcaacccc agtgggagct        780
ctaagtggtg cttttgactaa gcttcaagca agcaccaagt tcagaaaact tcgcgaagct        840
gcgaaaacca tcacaaaaca aattggaggg ccagcacatg aagttgcagc taaagtagat        900
gagtatgcta aggaatgat aagtgcttct gggtcaacac tctttgagga gcttgggttg        960
tattatattg gtccggtgga tggacataat gttggagatt tagtcaccat ttttgagaaa       1020
gtgaaatcaa tgccagcgcc aggaccagtc ttgatccaca tcgtcacaga gaagggaaa       1080 ggctatcccc cagctgaagt agcacctgat aaaatgcatg gagttgtaaa gtttgaccca       1140
acaacaggaa agcaatttaa gtccaaatcg tcgacactt catatactca atactttgct       1200
gaatctctaa taaagaagc tgaagaagat acaagattg ttgccataca cgcagcaatg       1260
ggtggtggca ctggtctcaa ttatttccag aagaaatttc ctgatcgttg ctttgatgtg       1320
gggattgctg agcaacatgc tgtcacgttt gcagctggat tagctgcaga gggtctcaaa       1380
ccattctgtg ccatatactc atcattcctg caacgaggat atgatcaggt tgcacatgat       1440
gtagaccttc aaaaattacc tgtccgtttt gcattggata gagctggcat ggttggcgca       1500
gatgggccta cccactgcgg tgcatttgat atcacctaca tggcctgctt gcccaacatg       1560
gttgtcatgg ctccatcaga tgaggctgaa cttatgcaca tggtgccac agcaacagct       1620 atagatgaca gacccagttg cttcaggttt ccaaggggca atggaattgg agcaaagctt       1680
ccagctaata taaaggaac tatacttgag attggaaaag gcagaatatt aatggaaggc       1740
agcagagtag ctattttggg ttatggttct attgttcagc aatgtgtgga agctgcaagc       1800
atattaaaga aacaagacat ttcagtgaca gtagctgatg caagattttg caaaccattg       1860
gatacaaatc tcataagacg gttagccaac gagcatgaaa tcctaatcac tgccgaagaa       1920
ggttctattg gaggctttgg gtctcatgtg tcacactttc taagcttaag tggacttctt       1980
gatgggtctt taaagttgag agcaatggtt cttcctgata gatacattga ccatggatca       2040
ccccaagatc agactgaaac agccgggctc tcctcgaggc atatatctgc aacagtctta       2100
tctctcttgg ggaagcccaa ggaagcactt cagttcatgt aa                           2142

<210> SEQ ID NO 20
<211> LENGTH: 1425
<212> TYPE: DNA
<213> ORGANISM: Cannabis sativa

<400> SEQUENCE: 20
atggctctga acttgttatc cccagctgaa gtgaaggctc tatcctttt ggactccacc         60
```

```
aagtccaccc gcttccctaa gctgtgtcca ggtggaatta ctttgcatag aaaggattgc      120
agagtaccac ttagaagaag agttcattgt tcgttgcagc aacctcctcc agcttggcca      180
ggaagagcta ttccagagca agatctttgt aattggaatg tcccaaagcc tatatctatt      240
attggctcta ctggctctat aggaactcag acactggaca ttgtggcaga gaatccagat      300
aaattcagaa tagtgggact tgcagctggt tcgaatgtga cacttcttgc agaccaggtg      360
aagagattca agcctcaaat agttgctctt agaaatgaat cattaattgg tgaactaaaa      420
gaggccttag ctgatgtgga agaaatgccc gaaattattc ctggggaaca aggagtaatt      480
gaggttgccc ggcacccaga tgcagtcaca gtggttacag aatagtaggt tgtgctgga       540 ttacagccta cagttgctgc aattgaggca ggtaaacaca tagctttagc caataaagag      600
accctgattg ctggaggtcc attcatcctt cctctagctc acaagcataa cataaaaatt      660
cttcctgccg attcagaaca ttcggcaata ttccagtgta tccagggctt gcctgatggt      720
gcactacggc gtatcatttt gacagcatct gggggagctt tcagagattg gccggttgaa      780
aagctaaaag atgttaaggt tgctgatgct ctgaaacatc caaactggcc gggtatggga      840
aagaaagtca ctattgattc tgctaccctt ttcaacaagg gtctggaagt cattgaagcc      900
cattatctat tcggagcaga ctatgacgat attgacattg tgattcaccc agaagctatt      960
atacactcta tgattgaaac acaggattct tctgttctgg ctcagttagg gtggcctgac     1020
atgcatatac cgattctcta tactatgtca tggccagaca gaatatactg ttctgaagta     1080
acttggcctc gacttgatct ttgcaagctt ggttcgctga cctttaggag tcctgacaac     1140
cagaagtacc catccataga tcttgcctat tctgctggac gtgctggggg caccatgact     1200
ggagttctca gtgcagccaa tgagaaagct gtagagatgt ttattgatga agataagt       1260 tatcttgaaa tcttcaaagt tgttgagcta acatgcgaca agcatcgatc agagatggtg     1320
acttcacctt ctcttgatga aattatccac tatgactcgt gggcacgaga gtatgcaact     1380
actagtttga gagttcttc cagtccaaga cctgttacag catga                     1425

<210> SEQ ID NO 21
<211> LENGTH: 918
<212> TYPE: DNA
<213> ORGANISM: Cannabis sativa

<400> SEQUENCE: 21
atggcgttac ttgcaatgga ccttactttc tcttctgctt ctctttcttc ttcttcctac       60
aatgctgctc ctctactatt tccttctatt cgcccatcct ctcaatccat tgttcgattc      120
ccagtccatg aggtgggatt caggggggaaa tgcagaattt ccaagataag gttcgctcgc     180
tgctctgcaa atgttggcca aaagcctggt gttgtggaaa agaaaagcgt tcggtggtt      240 cttctggcag gtgggaaggg taaacggatg ggggccaaca tgccaaagca gtatcttcca     300 ctttagggc aaccaattgc actgtatagc ttctacactt tttctaaaat gattgaagtg      360
actgaaattg ttgtagtttg tgatccctct tacgaggata tctttgaaga ttccaaagtc     420
aagatccatg ttggacttaa attcgctctg cctggaaagg aaagacagga ttcagtttat     480
agtggacttc aggcaattga tccaaactct aagcttgtgt gcattcacga ttctgctaga     540 ccttttggtaa caacagaaga agttaaaaag gtcattgaag atggttggtt gcatggagca     600
gctgtacttg gtgttcctgt caaagctaca atcaaagagg caaacaatgc atcttttgta     660
actaaaacgt tggagaggaa aaaacttttgg gaaatgcaga caccccaggt gatcaaaccc     720
gagttgctca aggaaggatt tgagcttgta aatagggaaa atctggaagt gactgatgat     780
```

| | |
|---|---:|
| gtgtctatag tggaacacct tggacatcct gtatatataa ctgaaggtgc ttacaccaac | 840 |
| atcaaggtta ctactccaga tgatttattg cttgcggaga gagtattgag tatgaactct | 900 |
| gtgaaggctg ttgcataa | 918 |

<210> SEQ ID NO 22
<211> LENGTH: 1197
<212> TYPE: DNA
<213> ORGANISM: Cannabis sativa

<400> SEQUENCE: 22

| | |
|---|---:|
| atggcttcct ctcatattct ctgccacaac aacgttttta atctttctcc caatcctttt | 60 |
| aggaacaggg gtctctcttc cttaaactca aatgggtttt gttttttttgg ttcgaaatct | 120 |
| agaatttcga ggccttcatc tctcaaaatt gtggtttctg aaagaagaca agttgagata | 180 |
| gtttatgatg ctgatgaaag gataaacaaa ttggctgatg tagtggacaa ggaagcgcct | 240 |
| cttctaggc tcactctttt ctcaccttgc aagattaatg ttttcttgag ataactagc | 300 |
| aaaagggaag atgggtatca tgatttggca tccctctttc acgtgataag tcttggagat | 360 |
| gtgcttaagt tctcttttgtc tccttcaaca agaaagatt cttttgtcaac gaatgcctct | 420 |
| ggggtaccac ttgatgatag aaatttgatt atcaaggccc ttaatcttta ccgaaagaaa | 480 |
| actggtacaa acaaatactt tggattcat cttgacaaga agtgcccac tggagcaggg | 540 |
| ctaggtggtg ggagcagcaa tgctgcaaca gccctatggg cagcaaatca gttcaatggt | 600 |
| tgtcttgtta ctgaaaagga attgcaagaa tggtcaagtg agattggttc agatgttcct | 660 |
| ttctttttct cccaaggggc agcctattgt acaggtcgag gtgaggttgt tcaggatatt | 720 |
| ctaccacctg taccattaaa cattcccatg gttctcataa agcccccaga gcatgttca | 780 |
| acagccgaag tttataagcg ttttcggttg gataaaacca gtaatagtga tccttacaa | 840 |
| ttgctccaca agatctcaag tgatggaata agtcaagatg tctgcatcaa tgacttagaa | 900 |
| cctcctgcct ttgaagttct tccatctctt aagagattga acagcgtat aattgcagct | 960 |
| agtcgtggac aatatgatgc tgtttttatg tctgggagtg gaagcaccat tgtcggggtc | 1020 |
| ggttccccag atccacctca gtttatatat gatgatgagg actacaagga tgtgttttttg | 1080 |
| tcagaggcca actttctgac tcgagaagca aatgaatggt acaaagaacc tgcttcagct | 1140 |
| agcgcttgta gccttcaga tgatttctct cgtaattttt cctcctctgt cgagtaa | 1197 |

<210> SEQ ID NO 23
<211> LENGTH: 738
<212> TYPE: DNA
<213> ORGANISM: Cannabis sativa

<400> SEQUENCE: 23

| | |
|---|---:|
| atggcggcgg cgacggcaac accactctgt gcttcaactc ttccaccaca ctactccaat | 60 |
| acctcccca atcattcaa tcactcccat ttcacagtcg cagttcccag aaatctcttc | 120 |
| tcatcgtcct caatttcatc tctaagacaa tcgaaaacga cgccgctttc ggctctgcct | 180 |
| tctgtatcgg ccgccgcgac caccgctttg aacgctgagc aagctccgtc tgaggtatct | 240 |
| gctactccct caaaggctct tccttttcgg gttggtcatg gtttgacct tcatcgattg | 300 |
| gagcctgggt atcctttgat aattggaggt attaatatac ctcatgagaa aggttgcgaa | 360 |
| gctcattctg atggggatgt tttgcttcat tgtgtagttg atgctatttt gggtgctttg | 420 |
| gggcttcctg atattggtca aatttttccct gattctgatc ccaaatggaa aggggctgca | 480 |

| | |
|---|---|
| tcatcagttt tcatcaaaga agctgtgaga ctgatgcatg aggcaggtta tgagcttgga | 540 |
| aatttagatg caacattaat tcttcaaaga ccaaagttaa gtccacacaa ggaagctatc | 600 |
| agagccaact tgtctgaact tctaggagct gaccctgcag ttgttaatct gaaagcgaaa | 660 |
| actcacgaaa aggtcgatag tctcggggaa aatcgaagca tcgctgctca cactgtggtt | 720 |
| cttcttatga aaaaatag | 738 |

<210> SEQ ID NO 24
<211> LENGTH: 2229
<212> TYPE: DNA
<213> ORGANISM: Cannabis sativa

<400> SEQUENCE: 24

| | |
|---|---|
| atggcttctg gagctgtacc agcatcaatt tcatgtctga aaagcagaga ctctggcttg | 60 |
| agctttgcta aaagttctga ttttgtgagg ctttctgatt taaagagggt tggttcatct | 120 |
| agaacaagag tttcagttat ccgaaattcg aatcctggtt cagatattgc tgaacttcag | 180 |
| cctgcatcaa aaggaagccc tctattagtt cctagacaga agtactgtga atccttacac | 240 |
| aaaactgtta ggaggaaaac gcgaactgtg atggtgggaa atgtggctct ggcagtgag | 300 |
| catcccataa gaattcaaac gatgacgaca atgatacca aggatgttgc tggaacagtt | 360 |
| gaagaggtga tgagaatagc tgataaggga gctgatattg ttcggataac agttcaggga | 420 |
| agaaaagaag cagatgcttg tttcgaaata aaaaattcac ttgtgcagaa gaattataat | 480 |
| atacctcttg tggcagatat tcattttgct cccccagttg cattaagagt tgctgaatgc | 540 |
| ttcgataaaa ttcgtgtcaa tcctggaaat ttcgctgaca gacgggctca gtttgagacg | 600 |
| ctcgagtaca cagacgacga ctatcagaaa gaacttgagc atattgagca ggtttttttct | 660 |
| ccattggttg agaaatgtaa gaaatatggt agagcaatgc gtatcgggac aaaccatggg | 720 |
| agtctttcag atcgtatcat gagctactat ggagattctc caggggaat ggttgaatct | 780 |
| gcatttgagt ttgcaaggat ttgccggaag ttggattttcc ataattttgt gttttcgatg | 840 |
| aaagcaagca acccagttgt catggttcag gcgtatcgtc tacttgttgc tgaaatgtat | 900 |
| gtccagggct gggactatcc acttcacttg gagttactg aagcgggaga aggtgaggat | 960 |
| ggacgaatga atctgcaat ggcatcggg acccttcttc aggatggttt gggtgatact | 1020 |
| atcagggttt cactcaccga accgcccgag gaggagattg atccctgcag aaggttggcc | 1080 |
| aatttgggta caaaagcagc tgatcttcag caaggagtgg ctccatttga agagaagcac | 1140 |
| aggcattatt ttgattttca cgacgaact ggtcaactgc ctctacagaa ggagggcgat | 1200 |
| gaggttgact atagaggtgc tctgcaccgt gatggttctg ttctcatgtc agtgtctctc | 1260 |
| aataacttaa agatgcccga gctcctatac aggtcactag cagcaaagct tgtcgtcggg | 1320 |
| atgccatta aggatctggc aacagtagac tccatcttat tgagacaact tccacctatt | 1380 |
| gacgatgaca acgctcgatt agctctcaaa agattgatag acataagtat ggggtcata | 1440 |
| actcctttgt cggagcagct aacaaagcca ttgccaaatg ctatggtttt ggtaaatctt | 1500 |
| aaggagttat catctggtgc acacaagctt ttgccagaag gcacgcgttt ggttgtatcc | 1560 |
| ttgcgcggtg atgaacctta cgaagaactg gagattctca aaggggttga tgatgttgtt | 1620 |
| atgattcttc atgatcttcc gttcgatgaa cataaaatta gcagagtcca ctcagcaaga | 1680 |
| agattatttg agtatctatc agataattct cttaactttc ctgtaataca ccacattcaa | 1740 |
| tttccaaatg gaatccacag ggatgactta gtcatcggtg caggtagcaa cgctggtgcc | 1800 |
| cttttagtag atggactcgg ggacggtatc ctcttagaag ccccagatca ggatttcgat | 1860 |

```
tttcttagaa atacttcttt caacctactt caaggttgta gaatgcgaaa tacaaagacg    1920
gagtatgtct cgtgcccatc ctgcggtaga actttgtttg accttcaaga aatcagcgca    1980
gagattcgag agaagacatc acacctgccc ggtgtctcaa ttgcaatcat gggttgcatt    2040
gttaatggac ccggagagat ggctgatgca gacttcggtt atgtcggtgg tgctcccgga    2100
aagattgacc tttatgttgg aaagacggta gtgcagcgtg gaatcgcaat ggaacaagcg    2160
accgatgcat tgattcagct aataaaagat catggccgat gggttgaacc accctcggac    2220
gaagaatga                                                             2229
```

<210> SEQ ID NO 25
<211> LENGTH: 1383
<212> TYPE: DNA
<213> ORGANISM: Cannabis sativa

<400> SEQUENCE: 25

```
atgtcgatca ctttccagct ctgccggatt ccaatccgta ccgacctcgc cttggcggag      60
cctctctccg taaccggaac cctccgctgc cggaaacctt cgtcatccg atgcgccggc     120 gagtcatctt caacggcagc agattctgat ttcgatgcga agtgttccg taagaacttg      180 gtccgaagca agaactacaa tcggaaaggt tttggccata aggaagagac ccttcaactc     240
atggacagcg agtacaccag tgatattata aagactttga aggataatgg aaatgagtac     300
aggtggggga acgtgacggt aaaattggcc gaagcatatg ggttttgctg gggtgtggag     360
cgagctgtcc aaattgctta cgaagcaagg aaacagttcc ccgaagaaaa gatttggatt     420
acaaacgaaa ttattcataa tccgacagtc aacaagagac tagaggaaat gaaagtggaa     480
aatattccaa ttgatgaagg gaggaaacaa tttgagattg taaacaaggg tgatgttgtg     540
atattgcctg cttttggtgc tggagtggat gagatgttgg ctttgagtga taggaatgtt     600
caaattgttg ataccacatg cccatgggtt tccaaggttt ggaatacagt cgagaaacat     660
aagaaaggtg aatacacttc cattattcat ggtaaatatg ctcatgagga gactatagct     720
actgcatctt tgctggaaac ttacattatt gtaaagaaca tgaaagaggc aatgtatgtc     780
tgtgattata ttcttggcgg tcaacttgat ggatccagct caacaagaga ggagtttatg     840
gagaaattta agaatgcagt ttctaaggga tttgatcctg acaaacatct tgtgaaggct     900
ggtattgcaa atcagactac aatgctcaag ggggaaaccg aagagattgg gaaactggtt     960
gagaggacta tgatgcaaaa gtacggagtt gaaaacatta tgaacacttt ccaaagctt    1020 aacacaattt gcgatgcaac ccaagagcgt caagatgcaa tgtacaagat ggtggaggaa    1080
cgtattgacc ttatgttagt tgttggagga tggaactcta gtaacacttc tcatctacaa    1140
gagattgcag aggaacgagg tattccctcg tattggattg acagtgaaca gagaataggt    1200
cctggaaaca agatagccta caagctaaat catggagagt tggttgagaa agagaactgg    1260
ttaccagagg gtcccatcac ggtcggtgta acatcaggtg cttctactcc agataaggtt    1320
gtggaagatg ttctcatcaa ggtgtttgac cttaagagcg aagaagcttt gcaagttgct    1380
tag                                                                  1383
```

<210> SEQ ID NO 26
<211> LENGTH: 627
<212> TYPE: PRT
<213> ORGANISM: Cannabis sativa

<400> SEQUENCE: 26

-continued

```
Met Ser Val Ile Ser Ile Leu Pro Leu Ala Ser Lys Ser Cys Leu Tyr
1               5                   10                  15

Lys Ser Leu Met Ser Ser Thr His Glu Leu Lys Ala Leu Cys Arg Pro
            20                  25                  30

Ile Ala Thr Leu Gly Met Cys Arg Arg Gly Lys Ser Val Met Ala Ser
            35                  40                  45

Lys Ser Thr Ser Leu Thr Thr Ala Val Ser Asp Asp Gly Val Gln Arg
50                  55                  60

Arg Ile Gly Asp His His Ser Asn Leu Trp Asp Asn Phe Ile Gln
65                  70                  75                  80

Ser Leu Ser Ser Pro Tyr Gly Ala Ser Ser Tyr Gly Glu Arg Ala Glu
                85                  90                  95

Arg Leu Ile Gly Glu Val Lys Glu Ile Phe Asn Ser Leu Ser Arg Thr
                100                 105                 110

Asp Gly Glu Leu Val Ser His Val Asp Asp Leu Leu Gln His Leu Ser
                115                 120                 125

Met Val Asp Asn Val Glu Arg Leu Gly Ile Asp Arg His Phe Gln Thr
130                 135                 140

Glu Ile Lys Val Ser Leu Asp Tyr Val Tyr Ser Tyr Trp Ser Glu Lys
145                 150                 155                 160

Gly Ile Gly Ser Gly Arg Asp Ile Val Cys Thr Asp Leu Asn Thr Thr
                165                 170                 175

Ala Leu Gly Phe Arg Ile Leu Arg Leu His Gly Tyr Thr Val Phe Pro
                180                 185                 190

Asp Val Phe Glu His Phe Lys Asp Gln Met Gly Arg Ile Ala Cys Ser
                195                 200                 205

Asp Asn His Thr Glu Arg Gln Ile Ser Ser Ile Leu Asn Leu Phe Arg
                210                 215                 220

Ala Ser Leu Ile Ala Phe Pro Gly Glu Lys Val Met Glu Glu Ala Glu
225                 230                 235                 240

Ile Phe Ser Ala Thr Tyr Leu Lys Glu Ala Leu Gln Thr Ile Pro Val
                245                 250                 255

Ser Ser Leu Ser Gln Glu Ile Gln Tyr Val Leu Gln Tyr Arg Trp His
                260                 265                 270

Ser Asn Leu Pro Arg Leu Glu Ala Arg Thr Tyr Ile Asp Ile Leu Gln
                275                 280                 285

Glu Asn Thr Lys Asn Gln Met Leu Asp Val Asn Thr Lys Lys Val Leu
                290                 295                 300

Glu Leu Ala Lys Leu Glu Phe Asn Ile Phe His Ser Leu Gln Gln Asn
305                 310                 315                 320

Glu Leu Lys Ser Val Ser Arg Trp Trp Lys Glu Ser Gly Phe Pro Asp
                325                 330                 335

Leu Asn Phe Ile Arg His Arg His Val Glu Phe Tyr Thr Leu Val Ser
                340                 345                 350

Gly Ile Asp Met Glu Pro Lys His Cys Thr Phe Arg Leu Ser Phe Val
                355                 360                 365

Lys Met Cys His Leu Ile Thr Val Leu Asp Asp Met Tyr Asp Thr Phe
                370                 375                 380

Gly Thr Ile Asp Glu Leu Arg Leu Phe Thr Ala Ala Val Lys Arg Trp
385                 390                 395                 400

Asp Pro Ser Thr Thr Glu Cys Leu Pro Glu Tyr Met Lys Gly Val Tyr
                405                 410                 415

Thr Val Leu Tyr Glu Thr Val Asn Glu Met Ala Gln Glu Ala Gln Lys
```

```
                420             425             430
Ser Gln Gly Arg Asp Thr Leu Ser Tyr Val Arg Gln Ala Leu Glu Ala
            435             440             445
Tyr Ile Gly Ala Tyr His Lys Glu Ala Glu Trp Ile Ser Ser Gly Tyr
        450             455             460
Leu Pro Thr Phe Asp Glu Tyr Phe Glu Asn Gly Lys Val Ser Ser Gly
465             470             475             480
His Arg Ile Ala Thr Leu Gln Pro Thr Phe Met Leu Asp Ile Pro Phe
            485             490             495
Pro His His Val Leu Gln Glu Ile Asp Phe Pro Ser Lys Phe Asn Asp
        500             505             510
Phe Ala Cys Ser Ile Leu Arg Leu Arg Gly Asp Thr Arg Cys Tyr Gln
        515             520             525
Ala Asp Arg Ala Arg Gly Glu Ala Ser Cys Ile Ser Cys Tyr Met
        530             535             540
Lys Asp Asn Pro Gly Ser Thr Gln Glu Asp Ala Leu Asn His Ile Asn
545             550             555             560
Asn Met Ile Glu Glu Thr Ile Lys Lys Leu Asn Trp Glu Leu Leu Lys
            565             570             575
Pro Asp Asn Asn Val Pro Ile Ser Ser Lys Lys His Ala Phe Asp Ile
        580             585             590
Asn Arg Gly Leu His His Phe Tyr Asn Tyr Arg Asp Gly Tyr Thr Val
        595             600             605
Ala Ser Asn Glu Thr Lys Asn Leu Val Ile Lys Thr Val Leu Glu Pro
        610             615             620
Val Pro Met
625

<210> SEQ ID NO 27
<211> LENGTH: 621
<212> TYPE: PRT
<213> ORGANISM: Cannabis sativa

<400> SEQUENCE: 27

Met Met Ser Phe Asp Ile Ala Lys Tyr Pro Thr Leu Ala Leu Val Asp
1               5               10              15
Ser Thr Gln Glu Leu Arg Leu Leu Pro Lys Glu Ser Leu Pro Lys Leu
            20              25              30
Cys Asp Glu Leu Arg Arg Tyr Leu Leu Asp Ser Val Ser Arg Ser Ser
        35              40              45
Gly His Phe Ala Ser Gly Leu Gly Thr Val Glu Leu Thr Val Ala Leu
    50              55              60
His Tyr Val Tyr Asn Thr Pro Phe Asp Gln Leu Ile Trp Asp Val Gly
65              70              75              80
His Gln Ala Tyr Pro His Lys Ile Leu Thr Gly Arg Arg Asp Lys Ile
            85              90              95
Gly Thr Ile Arg Gln Lys Gly Gly Leu His Pro Phe Pro Trp Arg Gly
        100             105             110
Glu Ser Glu Tyr Asp Val Leu Ser Val Gly His Ser Ser Thr Ser Ile
        115             120             125
Ser Ala Gly Ile Gly Ile Ala Val Ala Ala Glu Lys Glu Gly Lys Asn
    130             135             140
Arg Arg Thr Val Cys Val Ile Gly Asp Gly Ala Ile Thr Ala Gly Met
145             150             155             160
```

```
Ala Phe Glu Ala Met Asn His Ala Gly Asp Ile Arg Pro Asp Met Leu
                165                 170                 175

Val Val Leu Asn Asp Asn Glu Met Ser Ile Ser Glu Asn Val Gly Ala
            180                 185                 190

Leu Asn Asn His Leu Ala Gln Leu Leu Ser Gly Lys Leu Tyr Ser Ser
        195                 200                 205

Leu Arg Glu Gly Gly Lys Lys Val Phe Ser Gly Val Pro Pro Ile Lys
    210                 215                 220

Glu Leu Leu Lys Arg Thr Glu Glu His Ile Lys Gly Met Val Val Pro
225                 230                 235                 240

Gly Thr Leu Phe Glu Glu Leu Gly Phe Asn Tyr Ile Gly Pro Val Asp
                245                 250                 255

Gly His Asp Val Leu Gly Leu Ile Thr Thr Leu Lys Asn Met Arg Asp
            260                 265                 270

Leu Lys Gly Pro Gln Phe Leu His Ile Met Thr Lys Lys Gly Arg Gly
        275                 280                 285

Tyr Glu Pro Ala Glu Lys Asp Pro Ile Thr Phe His Ala Val Pro Lys
    290                 295                 300

Phe Asp Pro Ser Ser Gly Cys Leu Pro Lys Ser Ser Gly Gly Leu Pro
305                 310                 315                 320

Ser Tyr Ser Lys Ile Phe Gly Asp Trp Leu Cys Glu Thr Ala Ala Lys
                325                 330                 335

Asp Asn Lys Leu Met Ala Ile Thr Pro Ala Met Arg Glu Gly Ser Gly
            340                 345                 350

Met Val Glu Phe Ser Arg Lys Phe Pro Asp Arg Tyr Phe Asp Val Ala
        355                 360                 365

Ile Ala Glu Gln His Ala Val Thr Phe Ala Ala Gly Leu Ala Ile Gly
    370                 375                 380

Gly Tyr Lys Pro Ile Val Ala Ile Tyr Ser Thr Phe Leu Gln Arg Ala
385                 390                 395                 400

Tyr Asp Gln Val Leu His Asp Val Ala Ile Gln Lys Leu Pro Val Leu
                405                 410                 415

Phe Ala Ile Asp Arg Ala Gly Ile Val Gly Ala Asp Gly Gln Thr His
            420                 425                 430

Gln Gly Ala Phe Asp Leu Ser Tyr Leu Arg Cys Ile Pro Glu Met Val
        435                 440                 445

Ile Met Thr Pro Ser Asp Glu Asn Glu Cys Arg Gln Met Leu Tyr Thr
    450                 455                 460

Gly Tyr His Tyr Asn Asp Gly Pro Ser Ala Val Arg Tyr Pro Arg Gly
465                 470                 475                 480

Asn Ala Val Gly Val Glu Leu Thr Pro Leu Glu Lys Leu Pro Ile Gly
                485                 490                 495

Lys Gly Ile Val Lys Arg Arg Gly Glu Lys Leu Ala Ile Leu Asn Phe
            500                 505                 510

Gly Thr Leu Met Pro Glu Ala Ala Lys Val Ala Glu Ser Leu Asn Ala
        515                 520                 525

Thr Leu Val Asp Met Arg Phe Val Lys Pro Leu Asp Glu Ala Leu Ile
    530                 535                 540

Leu Glu Met Ala Ala Ser His Glu Ala Leu Val Thr Val Glu Glu Asn
545                 550                 555                 560

Ala Ile Met Gly Gly Ala Gly Ser Gly Val Asn Glu Val Leu Met Ala
                565                 570                 575

His Arg Lys Pro Val Pro Val Leu Asn Ile Gly Leu Pro Asp Phe Phe
```

```
                580             585             590
Ile Pro Gln Gly Thr Gln Glu Glu Met Arg Ala Glu Leu Gly Leu Asp
            595             600             605

Ala Ala Gly Met Glu Ala Lys Ile Lys Ala Trp Leu Ala
610             615             620

<210> SEQ ID NO 28
<211> LENGTH: 236
<212> TYPE: PRT
<213> ORGANISM: Cannabis sativa

<400> SEQUENCE: 28

Met Ala Thr Thr His Leu Asp Val Cys Ala Val Pro Ala Ala Gly
1               5               10              15

Phe Gly Arg Arg Met Gln Thr Glu Cys Pro Lys Gln Tyr Leu Ser Ile
                20              25              30

Gly Asn Gln Thr Ile Leu Glu His Ser Val His Ala Leu Leu Ala His
                35              40              45

Pro Arg Val Lys Arg Val Val Ile Ala Ile Ser Pro Gly Asp Ser Arg
        50              55              60

Phe Ala Gln Leu Pro Leu Ala Asn His Pro Gln Ile Thr Val Val Asp
65              70              75              80

Gly Gly Asp Glu Arg Ala Asp Ser Val Leu Ala Gly Leu Lys Ala Ala
                85              90              95

Gly Asp Ala Gln Trp Val Leu Val His Asp Ala Ala Arg Pro Cys Leu
                100             105             110

His Gln Asp Asp Leu Ala Arg Leu Leu Ala Leu Ser Glu Thr Ser Arg
                115             120             125

Thr Gly Gly Ile Leu Ala Ala Pro Val Arg Asp Thr Met Lys Arg Ala
        130             135             140

Glu Pro Gly Lys Asn Ala Ile Ala His Thr Val Asp Arg Asn Gly Leu
145             150             155             160

Trp His Ala Leu Thr Pro Gln Phe Phe Pro Arg Glu Leu Leu His Asp
                165             170             175

Cys Leu Thr Arg Ala Leu Asn Glu Gly Ala Thr Ile Thr Asp Glu Ala
                180             185             190

Ser Ala Leu Glu Tyr Cys Gly Phe His Pro Gln Leu Val Glu Gly Arg
                195             200             205

Ala Asp Asn Ile Lys Ile Thr Arg Pro Glu Asp Leu Ala Leu Ala Glu
        210             215             220

Phe Tyr Leu Thr Arg Thr Ile His Gln Glu Asn Thr
225             230             235

<210> SEQ ID NO 29
<211> LENGTH: 159
<212> TYPE: PRT
<213> ORGANISM: Cannabis sativa

<400> SEQUENCE: 29

Met Arg Ile Gly His Gly Phe Asp Val His Ala Phe Gly Gly Glu Gly
1               5               10              15

Pro Ile Ile Ile Gly Gly Val Arg Ile Pro Tyr Glu Lys Gly Leu Leu
                20              25              30

Ala His Ser Asp Gly Asp Val Ala Leu His Ala Leu Thr Asp Ala Leu
                35              40              45

Leu Gly Ala Ala Ala Leu Gly Asp Ile Gly Lys Leu Phe Pro Asp Thr
```

```
                    50                  55                  60
Asp Pro Ala Phe Lys Gly Ala Asp Ser Arg Glu Leu Leu Arg Glu Ala
 65                  70                  75                  80

Trp Arg Arg Ile Gln Ala Lys Gly Tyr Thr Leu Gly Asn Ile Asp Val
                 85                  90                  95

Thr Ile Ile Ala Gln Ala Pro Lys Met Leu Pro His Ile Pro Gln Met
            100                 105                 110

Arg Val Phe Ile Ala Glu Asp Leu Gly Cys His Met Asp Asp Val Asn
        115                 120                 125

Val Lys Ala Thr Thr Glu Lys Leu Gly Phe Thr Gly Arg Gly Glu
    130                 135                 140

Gly Ile Ala Cys Glu Ala Val Ala Leu Leu Ile Lys Ala Thr Lys
145                 150                 155
```

<210> SEQ ID NO 30
<211> LENGTH: 182
<212> TYPE: PRT
<213> ORGANISM: Cannabis sativa

<400> SEQUENCE: 30

```
Met Gln Thr Glu His Val Ile Leu Leu Asn Ala Gln Gly Val Pro Thr
 1               5                  10                  15

Gly Thr Leu Glu Lys Tyr Ala Ala His Thr Ala Asp Thr Arg Leu His
             20                  25                  30

Leu Ala Phe Ser Ser Trp Leu Phe Asn Ala Lys Gly Gln Leu Leu Val
         35                  40                  45

Thr Arg Arg Ala Leu Ser Lys Lys Ala Trp Pro Gly Val Trp Thr Asn
     50                  55                  60

Ser Val Cys Gly His Pro Gln Leu Gly Glu Ser Asn Glu Asp Ala Val
 65                  70                  75                  80

Ile Arg Arg Cys Arg Tyr Glu Leu Gly Val Glu Ile Thr Pro Pro Glu
                 85                  90                  95

Ser Ile Tyr Pro Asp Phe Arg Tyr Arg Ala Thr Asp Pro Ser Gly Ile
            100                 105                 110

Val Glu Asn Glu Val Cys Pro Val Phe Ala Ala Arg Thr Thr Ser Ala
        115                 120                 125

Leu Gln Ile Asn Asp Asp Glu Val Met Asp Tyr Gln Trp Cys Asp Leu
    130                 135                 140

Ala Asp Ile Leu His Gly Ile Asp Ala Thr Pro Trp Ala Phe Ser Pro
145                 150                 155                 160

Trp Met Val Met Gln Ala Thr Asn Arg Glu Ala Arg Lys Arg Leu Ser
                165                 170                 175

Ala Phe Thr Gln Leu Lys
            180
```

<210> SEQ ID NO 31
<211> LENGTH: 381
<212> TYPE: PRT
<213> ORGANISM: Cannabis sativa

<400> SEQUENCE: 31

```
Met Ala Tyr Ser Ala Met Ala Thr Met Gly Tyr Asn Gly Met Ala Ala
 1               5                  10                  15

Ser Cys His Thr Leu His Pro Thr Ser Pro Leu Lys Pro Phe His Gly
             20                  25                  30

Ala Ser Thr Ser Leu Glu Ala Phe Asn Gly Glu His Met Gly Leu Leu
```

```
              35                  40                  45
Arg Gly Tyr Ser Lys Arg Lys Leu Ser Ser Tyr Lys Asn Pro Ala Ser
 50                  55                  60

Arg Ser Ser Asn Ala Thr Val Ala Gln Leu Leu Asn Pro Pro Gln Lys
 65                  70                  75                  80

Gly Lys Lys Ala Val Glu Phe Asp Phe Asn Lys Tyr Met Asp Ser Lys
                 85                  90                  95

Ala Met Thr Val Asn Glu Ala Leu Asn Lys Ala Ile Pro Leu Arg Tyr
                100                 105                 110

Pro Gln Lys Ile Tyr Glu Ser Met Arg Tyr Ser Leu Leu Ala Gly Gly
            115                 120                 125

Lys Arg Val Arg Pro Val Leu Cys Ile Ala Ala Cys Glu Leu Val Gly
130                 135                 140

Gly Thr Glu Glu Leu Ala Ile Pro Thr Ala Cys Ala Ile Glu Met Ile
145                 150                 155                 160

His Thr Met Ser Leu Met His Asp Asp Leu Pro Cys Ile Asp Asn Asp
                165                 170                 175

Asp Leu Arg Arg Gly Lys Pro Thr Asn His Lys Ile Phe Gly Glu Asp
            180                 185                 190

Thr Ala Val Thr Ala Gly Asn Ala Leu His Ser Tyr Ala Phe Glu His
        195                 200                 205

Ile Ala Val Ser Thr Ser Lys Thr Val Gly Ala Asp Arg Ile Leu Arg
210                 215                 220

Met Val Ser Glu Leu Gly Arg Ala Thr Gly Ser Glu Gly Val Met Gly
225                 230                 235                 240

Gly Gln Met Val Asp Ile Ala Ser Glu Gly Asp Pro Ser Ile Asp Leu
                245                 250                 255

Gln Thr Leu Glu Trp Ile His Ile His Lys Thr Ala Met Leu Leu Glu
            260                 265                 270

Cys Ser Val Val Cys Gly Ala Ile Ile Gly Gly Ala Ser Glu Ile Val
        275                 280                 285

Ile Glu Arg Ala Arg Arg Tyr Ala Arg Cys Val Gly Leu Leu Phe Gln
290                 295                 300

Val Val Asp Asp Ile Leu Asp Val Thr Lys Ser Ser Asp Glu Leu Gly
305                 310                 315                 320

Lys Thr Ala Gly Lys Asp Leu Ile Ser Asp Lys Ala Thr Tyr Pro Lys
                325                 330                 335

Leu Met Gly Leu Glu Lys Ala Lys Glu Phe Ser Asp Glu Leu Leu Asn
            340                 345                 350

Arg Ala Lys Gly Glu Leu Ser Cys Phe Asp Pro Val Lys Ala Ala Pro
        355                 360                 365

Leu Leu Gly Leu Ala Asp Tyr Val Ala Phe Arg Gln Asn
370                 375                 380

<210> SEQ ID NO 32
<211> LENGTH: 299
<212> TYPE: PRT
<213> ORGANISM: Cannabis sativa

<400> SEQUENCE: 32

Met Asp Phe Pro Gln Gln Leu Glu Ala Cys Val Lys Gln Ala Asn Gln
  1               5                  10                  15

Ala Leu Ser Arg Phe Ile Ala Pro Leu Pro Phe Gln Asn Thr Pro Val
             20                  25                  30
```

```
Val Glu Thr Met Gln Tyr Gly Ala Leu Leu Gly Lys Arg Leu Arg
         35                  40                  45

Pro Phe Leu Val Tyr Ala Thr Gly His Met Phe Gly Ile Ser Thr Asn
 50                  55                  60

Thr Leu Asp Ala Pro Ala Ala Val Glu Cys Ile His Ala Tyr Ser
 65                  70                  75                  80

Leu Ile His Asp Asp Leu Pro Ala Met Asp Asp Asp Leu Arg Arg
                 85                  90                  95

Gly Leu Pro Thr Cys His Val Lys Phe Gly Glu Ala Asn Ala Ile Leu
                100                 105                 110

Ala Gly Asp Ala Leu Gln Thr Leu Ala Phe Ser Ile Leu Ser Asp Ala
                115                 120                 125

Asp Met Pro Glu Val Ser Asp Arg Asp Arg Ile Ser Met Ile Ser Glu
130                 135                 140

Leu Ala Ser Ala Ser Gly Ile Ala Gly Met Cys Gly Gly Gln Ala Leu
145                 150                 155                 160

Asp Leu Asp Ala Glu Gly Lys His Val Pro Leu Asp Ala Leu Glu Arg
                165                 170                 175

Ile His Arg His Lys Thr Gly Ala Leu Ile Arg Ala Ala Val Arg Leu
                180                 185                 190

Gly Ala Leu Ser Ala Gly Asp Lys Gly Arg Arg Ala Leu Pro Val Leu
                195                 200                 205

Asp Lys Tyr Ala Glu Ser Ile Gly Leu Ala Phe Gln Val Gln Asp Asp
                210                 215                 220

Ile Leu Asp Val Val Gly Asp Thr Ala Thr Leu Gly Lys Arg Gln Gly
225                 230                 235                 240

Ala Asp Gln Gln Leu Gly Lys Ser Thr Tyr Pro Ala Leu Leu Gly Leu
                245                 250                 255

Glu Gln Ala Arg Lys Lys Ala Arg Asp Leu Ile Asp Asp Ala Arg Gln
                260                 265                 270

Ser Leu Lys Gln Leu Ala Glu Gln Ser Leu Asp Thr Ser Ala Leu Glu
                275                 280                 285

Ala Leu Ala Asp Tyr Ile Ile Gln Arg Asn Lys
                290                 295
```

<210> SEQ ID NO 33
<211> LENGTH: 398
<212> TYPE: PRT
<213> ORGANISM: Cannabis sativa

<400> SEQUENCE: 33

```
Met Lys Gln Leu Thr Ile Leu Gly Ser Thr Gly Ser Ile Gly Cys Ser
 1               5                  10                  15

Thr Leu Asp Val Val Arg His Asn Pro Glu His Phe Arg Val Val Ala
                 20                  25                  30

Leu Val Ala Gly Lys Asn Val Thr Arg Met Val Glu Gln Cys Leu Glu
                 35                  40                  45

Phe Ser Pro Arg Tyr Ala Val Met Asp Asp Glu Ala Ser Ala Lys Leu
 50                  55                  60

Leu Lys Thr Met Leu Gln Gln Gly Ser Arg Thr Glu Val Leu Ser
 65                  70                  75                  80

Gly Gln Gln Ala Ala Cys Asp Met Ala Ala Leu Glu Asp Val Asp Gln
                 85                  90                  95

Val Met Ala Ala Ile Val Gly Ala Ala Gly Leu Leu Pro Thr Leu Ala
                100                 105                 110
```

```
Ala Ile Arg Ala Gly Lys Thr Ile Leu Leu Ala Asn Lys Glu Ser Leu
            115                 120                 125

Val Thr Cys Gly Arg Leu Phe Met Asp Ala Val Lys Gln Ser Lys Ala
    130                 135                 140

Gln Leu Leu Pro Val Asp Ser Glu His Asn Ala Ile Phe Gln Ser Leu
145                 150                 155                 160

Pro Gln Pro Ile Gln His Asn Leu Gly Tyr Ala Asp Leu Glu Gln Asn
                165                 170                 175

Gly Val Val Ser Ile Leu Leu Thr Gly Ser Gly Pro Phe Arg Glu
                180                 185                 190

Thr Pro Leu Arg Asp Leu Ala Thr Met Thr Pro Asp Gln Ala Cys Arg
                195                 200                 205

His Pro Asn Trp Ser Met Gly Arg Lys Ile Ser Val Asp Ser Ala Thr
            210                 215                 220

Met Met Asn Lys Gly Leu Glu Tyr Ile Glu Ala Arg Trp Leu Phe Asn
225                 230                 235                 240

Ala Ser Ala Ser Gln Met Glu Val Leu Ile His Pro Gln Ser Val Ile
                245                 250                 255

His Ser Met Val Arg Tyr Gln Asp Gly Ser Val Leu Ala Gln Leu Gly
            260                 265                 270

Glu Pro Asp Met Arg Thr Pro Ile Ala His Thr Met Ala Trp Pro Asn
        275                 280                 285

Arg Val Asn Ser Gly Val Lys Pro Leu Asp Phe Cys Lys Leu Ser Ala
        290                 295                 300

Leu Thr Phe Ala Ala Pro Asp Tyr Asp Arg Tyr Pro Cys Leu Lys Leu
305                 310                 315                 320

Ala Met Glu Ala Phe Glu Gln Gly Gln Ala Ala Thr Thr Ala Leu Asn
                325                 330                 335

Ala Ala Asn Glu Ile Thr Val Ala Ala Phe Leu Ala Gln Gln Ile Arg
            340                 345                 350

Phe Thr Asp Ile Ala Ala Leu Asn Leu Ser Val Leu Glu Lys Met Asp
            355                 360                 365

Met Arg Glu Pro Gln Cys Val Asp Asp Val Leu Ser Val Asp Ala Asn
        370                 375                 380

Ala Arg Glu Val Ala Arg Lys Glu Val Met Arg Leu Ala Ser
385                 390                 395

<210> SEQ ID NO 34
<211> LENGTH: 283
<212> TYPE: PRT
<213> ORGANISM: Cannabis sativa

<400> SEQUENCE: 34

Met Arg Thr Gln Trp Pro Ser Pro Ala Lys Leu Asn Leu Phe Leu Tyr
1               5                   10                  15

Ile Thr Gly Gln Arg Ala Asp Gly Tyr His Thr Leu Gln Thr Leu Phe
            20                  25                  30

Gln Phe Leu Asp Tyr Gly Asp Thr Ile Ser Ile Glu Leu Arg Asp Asp
        35                  40                  45

Gly Asp Ile Arg Leu Leu Thr Pro Val Glu Gly Val Glu His Glu Asp
    50                  55                  60

Asn Leu Ile Val Arg Ala Ala Arg Leu Leu Ile Lys Thr Ala Ala Asp
65                  70                  75                  80

Ser Gly Arg Leu Pro Thr Gly Ser Gly Ala Asn Ile Ser Ile Asp Lys
```

```
                    85                  90                  95
Arg Leu Pro Met Gly Gly Leu Gly Gly Ser Ser Asn Ala Ala
            100                 105                 110

Thr Val Leu Val Ala Leu Asn Tyr Leu Trp Gln Cys Gly Leu Ser Met
            115                 120                 125

Asp Glu Leu Ala Glu Met Gly Leu Thr Leu Gly Ala Asp Val Pro Val
            130                 135                 140

Phe Val Arg Gly His Ala Ala Phe Ala Glu Val Gly Glu Ile Leu
145                 150                 155                 160

Thr Pro Val Asp Pro Glu Lys Trp Tyr Leu Val Ala His Pro Gly
                165                 170                 175

Val Ser Ile Pro Thr Pro Val Ile Phe Lys Asp Pro Glu Leu Pro Arg
            180                 185                 190

Asn Thr Pro Lys Arg Ser Ile Glu Thr Leu Leu Lys Cys Glu Phe Ser
            195                 200                 205

Asn Asp Cys Glu Val Ile Ala Arg Lys Arg Phe Arg Glu Val Asp Ala
            210                 215                 220

Val Leu Ser Trp Leu Leu Glu Tyr Ala Pro Ser Arg Leu Thr Gly Thr
225                 230                 235                 240

Gly Ala Cys Val Phe Ala Glu Phe Asp Thr Glu Ser Glu Ala Arg Gln
                245                 250                 255

Val Leu Glu Gln Ala Pro Glu Trp Leu Asn Gly Phe Val Ala Lys Gly
            260                 265                 270

Val Asn Leu Ser Pro Leu His Arg Ala Met Leu
            275                 280

<210> SEQ ID NO 35
<211> LENGTH: 372
<212> TYPE: PRT
<213> ORGANISM: Cannabis sativa

<400> SEQUENCE: 35

Met His Asn Gln Ala Pro Ile Gln Arg Arg Lys Ser Thr Arg Ile Tyr
1               5                   10                  15

Val Gly Asn Val Pro Ile Gly Asp Gly Ala Pro Ile Ala Val Gln Ser
            20                  25                  30

Met Thr Asn Thr Arg Thr Thr Asp Val Glu Ala Thr Val Asn Gln Ile
        35                  40                  45

Lys Ala Leu Glu Arg Val Gly Ala Asp Ile Val Arg Val Ser Val Pro
50                  55                  60

Thr Met Asp Ala Ala Glu Ala Phe Lys Leu Ile Lys Gln Gln Val Asn
65                  70                  75                  80

Val Pro Leu Val Ala Asp Ile His Phe Asp Tyr Arg Ile Ala Leu Lys
                85                  90                  95

Val Ala Glu Tyr Gly Val Asp Cys Leu Arg Ile Asn Pro Gly Asn Ile
            100                 105                 110

Gly Asn Glu Glu Arg Ile Arg Met Val Val Asp Cys Ala Arg Asp Lys
        115                 120                 125

Asn Ile Pro Ile Arg Ile Gly Val Asn Ala Gly Ser Leu Glu Lys Asp
        130                 135                 140

Leu Gln Glu Lys Tyr Gly Glu Pro Thr Pro Gln Ala Leu Leu Glu Ser
145                 150                 155                 160

Ala Met Arg His Val Asp His Leu Asp Arg Leu Asn Phe Asp Gln Phe
                165                 170                 175
```

```
Lys Val Ser Val Lys Ala Ser Asp Val Phe Leu Ala Val Glu Ser Tyr
            180                 185                 190

Arg Leu Leu Ala Lys Gln Ile Asp Gln Pro Leu His Leu Gly Ile Thr
        195                 200                 205

Glu Ala Gly Gly Ala Arg Ser Gly Ala Val Lys Ser Ala Ile Gly Leu
    210                 215                 220

Gly Leu Leu Leu Ser Glu Gly Ile Gly Asp Thr Leu Arg Val Ser Leu
225                 230                 235                 240

Ala Ala Asp Pro Val Glu Glu Ile Lys Val Gly Phe Asp Ile Leu Lys
                245                 250                 255

Ser Leu Arg Ile Arg Ser Arg Gly Ile Asn Phe Ile Ala Cys Pro Thr
            260                 265                 270

Cys Ser Arg Gln Glu Phe Asp Val Ile Gly Thr Val Asn Ala Leu Glu
        275                 280                 285

Gln Arg Leu Glu Asp Ile Ile Thr Pro Met Asp Val Ser Ile Ile Gly
    290                 295                 300

Cys Val Val Asn Gly Pro Gly Glu Ala Leu Val Ser Thr Leu Gly Val
305                 310                 315                 320

Thr Gly Gly Asn Lys Lys Ser Gly Leu Tyr Glu Asp Gly Val Arg Lys
                325                 330                 335

Asp Arg Leu Asp Asn Asn Asp Met Ile Asp Gln Leu Glu Ala Arg Ile
            340                 345                 350

Arg Ala Lys Ala Ser Gln Leu Asp Glu Ala Arg Arg Ile Asp Val Gln
        355                 360                 365

Gln Val Glu Lys
    370

<210> SEQ ID NO 36
<211> LENGTH: 316
<212> TYPE: PRT
<213> ORGANISM: Cannabis sativa

<400> SEQUENCE: 36

Met Gln Ile Leu Leu Ala Asn Pro Arg Gly Phe Cys Ala Gly Val Asp
1               5                   10                  15

Arg Ala Ile Ser Ile Val Glu Asn Ala Leu Ala Ile Tyr Gly Ala Pro
            20                  25                  30

Ile Tyr Val Arg His Glu Val Val His Asn Arg Tyr Val Val Asp Ser
        35                  40                  45

Leu Arg Glu Arg Gly Ala Ile Phe Ile Glu Gln Ile Ser Glu Val Pro
    50                  55                  60

Asp Gly Ala Ile Leu Ile Phe Ser Ala His Gly Val Ser Gln Ala Val
65                  70                  75                  80

Arg Asn Glu Ala Lys Ser Arg Asp Leu Thr Val Phe Asp Ala Thr Cys
                85                  90                  95

Pro Leu Val Thr Lys Val His Met Glu Val Ala Arg Ala Ser Arg Arg
            100                 105                 110

Gly Glu Glu Ser Ile Leu Ile Gly His Ala Gly His Pro Glu Val Glu
        115                 120                 125

Gly Thr Met Gly Gln Tyr Ser Asn Pro Glu Gly Gly Met Tyr Leu Val
    130                 135                 140

Glu Ser Pro Asp Asp Val Trp Lys Leu Thr Val Lys Asn Glu Glu Lys
145                 150                 155                 160

Leu Ser Phe Met Thr Gln Thr Thr Leu Ser Val Asp Asp Thr Ser Asp
                165                 170                 175
```

```
Val Ile Asp Ala Leu Arg Lys Arg Phe Pro Lys Ile Val Gly Pro Arg
                180                 185                 190

Lys Asp Asp Ile Cys Tyr Ala Thr Thr Asn Arg Gln Glu Ala Val Arg
            195                 200                 205

Ala Leu Ala Glu Gln Ala Glu Val Val Leu Val Gly Ser Lys Asn
210                 215                 220

Ser Ser Asn Ser Asn Arg Leu Ala Glu Leu Ala Gln Arg Met Gly Lys
225                 230                 235                 240

Arg Ala Phe Leu Ile Asp Asp Ala Lys Asp Ile Gln Glu Glu Trp Val
                245                 250                 255

Lys Glu Val Lys Cys Val Gly Val Thr Ala Gly Ala Ser Ala Pro Asp
            260                 265                 270

Ile Leu Val Gln Asn Val Val Ala Arg Leu Gln Gln Leu Gly Gly Gly
            275                 280                 285

Glu Ala Ile Pro Leu Glu Gly Arg Glu Glu Asn Ile Val Phe Glu Val
            290                 295                 300

Pro Lys Glu Leu Arg Val Asp Ile Arg Glu Val Asp
305                 310                 315

<210> SEQ ID NO 37
<211> LENGTH: 307
<212> TYPE: PRT
<213> ORGANISM: Cannabis sativa

<400> SEQUENCE: 37

Met Val Ser Gly Ser Lys Ala Gly Val Ser Pro His Arg Glu Ile Glu
1               5                   10                  15

Val Met Arg Gln Ser Ile Asp Asp His Leu Ala Gly Leu Leu Pro Glu
            20                  25                  30

Thr Asp Ser Gln Asp Ile Val Ser Leu Ala Met Arg Glu Gly Val Met
        35                  40                  45

Ala Pro Gly Lys Arg Ile Arg Pro Leu Leu Met Leu Leu Ala Ala Arg
    50                  55                  60

Asp Leu Arg Tyr Gln Gly Ser Met Pro Thr Leu Leu Asp Leu Ala Cys
65                  70                  75                  80

Ala Val Glu Leu Thr His Thr Ala Ser Leu Met Leu Asp Asp Met Pro
                85                  90                  95

Cys Met Asp Asn Ala Glu Leu Arg Arg Gly Gln Pro Thr Thr His Lys
            100                 105                 110

Lys Phe Gly Glu Ser Val Ala Ile Leu Ala Ser Val Gly Leu Leu Ser
        115                 120                 125

Lys Ala Phe Gly Leu Ile Ala Ala Thr Gly Asp Leu Pro Gly Glu Arg
130                 135                 140

Arg Ala Gln Ala Val Asn Glu Leu Ser Thr Ala Val Gly Val Gln Gly
145                 150                 155                 160

Leu Val Leu Gly Gln Phe Arg Asp Leu Asn Asp Ala Ala Leu Asp Arg
                165                 170                 175

Thr Pro Asp Ala Ile Leu Ser Thr Asn His Leu Lys Thr Gly Ile Leu
            180                 185                 190

Phe Ser Ala Met Leu Gln Ile Val Ala Ile Ala Ser Ala Ser Ser Pro
        195                 200                 205

Ser Thr Arg Glu Thr Leu His Ala Phe Ala Leu Asp Phe Gly Gln Ala
    210                 215                 220

Phe Gln Leu Leu Asp Asp Leu Arg Asp Asp His Pro Glu Thr Gly Lys
```

```
225                 230                 235                 240

Asp Arg Asn Lys Asp Ala Gly Lys Ser Thr Leu Val Asn Arg Leu Gly
                245                 250                 255

Ala Asp Ala Ala Arg Gln Lys Leu Arg Glu His Ile Asp Ser Ala Asp
            260                 265                 270

Lys His Leu Thr Phe Ala Cys Pro Gln Gly Gly Ala Ile Arg Gln Phe
        275                 280                 285

Met His Leu Trp Phe Gly His His Leu Ala Asp Trp Ser Pro Val Met
    290                 295                 300

Lys Ile Ala
305

<210> SEQ ID NO 38
<211> LENGTH: 492
<212> TYPE: PRT
<213> ORGANISM: Cannabis sativa

<400> SEQUENCE: 38

Met Lys Lys Thr Val Val Ile Gly Ala Gly Phe Gly Gly Leu Ala Leu
1               5                   10                  15

Ala Ile Arg Leu Gln Ala Ala Gly Ile Pro Thr Val Leu Leu Glu Gln
            20                  25                  30

Arg Asp Lys Pro Gly Gly Arg Ala Tyr Val Trp His Asp Gln Gly Phe
        35                  40                  45

Thr Phe Asp Ala Gly Pro Thr Val Ile Thr Asp Pro Thr Ala Leu Glu
    50                  55                  60

Ala Leu Phe Thr Leu Ala Gly Arg Arg Met Glu Asp Tyr Val Arg Leu
65                  70                  75                  80

Leu Pro Val Lys Pro Phe Tyr Arg Leu Cys Trp Glu Ser Gly Lys Thr
                85                  90                  95

Leu Asp Tyr Ala Asn Asp Ser Ala Glu Leu Glu Ala Gln Ile Thr Gln
            100                 105                 110

Phe Asn Pro Arg Asp Val Glu Gly Tyr Arg Arg Phe Leu Ala Tyr Ser
        115                 120                 125

Gln Ala Val Phe Gln Glu Gly Tyr Leu Arg Leu Gly Ser Val Pro Phe
    130                 135                 140

Leu Ser Phe Arg Asp Met Leu Arg Ala Gly Pro Gln Leu Leu Lys Leu
145                 150                 155                 160

Gln Ala Trp Gln Ser Val Tyr Gln Ser Val Ser Arg Phe Ile Glu Asp
                165                 170                 175

Glu His Leu Arg Gln Ala Phe Ser Phe His Ser Leu Leu Val Gly Gly
            180                 185                 190

Asn Pro Phe Thr Thr Ser Ser Ile Tyr Thr Leu Ile His Ala Leu Glu
        195                 200                 205

Arg Glu Trp Gly Val Trp Phe Pro Glu Gly Gly Thr Gly Ala Leu Val
    210                 215                 220

Asn Gly Met Val Lys Leu Phe Thr Asp Leu Gly Gly Glu Ile Glu Leu
225                 230                 235                 240

Asn Ala Arg Val Glu Glu Leu Val Val Ala Asp Asn Arg Val Ser Gln
                245                 250                 255

Val Arg Leu Ala Asp Gly Arg Ile Phe Asp Thr Asp Ala Val Ala Ser
            260                 265                 270

Asn Ala Asp Val Val Asn Thr Tyr Lys Lys Leu Leu Gly His His Pro
        275                 280                 285
```

-continued

```
Val Gly Gln Lys Arg Ala Ala Leu Glu Arg Lys Ser Met Ser Asn
    290                 295                 300

Ser Leu Phe Val Leu Tyr Phe Gly Leu Asn Gln Pro His Ser Gln Leu
305                 310                 315                 320

Ala His His Thr Ile Cys Phe Gly Pro Arg Tyr Arg Glu Leu Ile Asp
                    325                 330                 335

Glu Ile Phe Thr Gly Ser Ala Leu Ala Asp Asp Phe Ser Leu Tyr Leu
                340                 345                 350

His Ser Pro Cys Val Thr Asp Pro Ser Leu Ala Pro Gly Cys Ala
            355                 360                 365

Ser Phe Tyr Val Leu Ala Pro Val Pro His Leu Gly Asn Ala Pro Leu
370                 375                 380

Asp Trp Ala Gln Glu Gly Pro Lys Leu Arg Asp Arg Ile Phe Asp Tyr
385                 390                 395                 400

Leu Glu Glu Arg Tyr Met Pro Gly Leu Arg Ser Gln Leu Val Thr Gln
                405                 410                 415

Arg Ile Phe Thr Pro Ala Asp Phe His Asp Thr Leu Asp Ala His Leu
                420                 425                 430

Gly Ser Ala Phe Ser Ile Glu Pro Leu Leu Thr Gln Ser Ala Trp Phe
            435                 440                 445

Arg Pro His Asn Arg Asp Ser Asp Ile Ala Asn Leu Tyr Leu Val Gly
450                 455                 460

Ala Gly Thr His Pro Gly Ala Gly Ile Pro Gly Val Val Ala Ser Ala
465                 470                 475                 480

Lys Ala Thr Ala Ser Leu Met Ile Glu Asp Leu Gln
                485                 490

<210> SEQ ID NO 39
<211> LENGTH: 309
<212> TYPE: PRT
<213> ORGANISM: Cannabis sativa

<400> SEQUENCE: 39

Met Ser Gln Pro Pro Leu Leu Asp His Ala Thr Gln Thr Met Ala Asn
1               5                   10                  15

Gly Ser Lys Ser Phe Ala Thr Ala Ala Lys Leu Phe Asp Pro Ala Thr
                20                  25                  30

Arg Arg Ser Val Leu Met Leu Tyr Thr Trp Cys Arg His Cys Asp Asp
            35                  40                  45

Val Ile Asp Asp Gln Thr His Gly Phe Ala Ser Glu Ala Ala Ala Glu
50                  55                  60

Glu Glu Ala Thr Gln Arg Leu Ala Arg Leu Arg Thr Leu Thr Leu Ala
65                  70                  75                  80

Ala Phe Glu Gly Ala Glu Met Gln Asp Pro Ala Phe Ala Ala Phe Gln
                85                  90                  95

Glu Val Ala Leu Thr His Gly Ile Thr Pro Arg Met Ala Leu Asp His
                100                 105                 110

Leu Asp Gly Phe Ala Met Asp Val Ala Gln Thr Arg Tyr Val Thr Phe
            115                 120                 125

Glu Asp Thr Leu Arg Tyr Cys Tyr His Val Ala Gly Val Val Gly Leu
            130                 135                 140

Met Met Ala Arg Val Met Gly Val Arg Asp Glu Arg Val Leu Asp Arg
145                 150                 155                 160

Ala Cys Asp Leu Gly Leu Ala Phe Gln Leu Thr Asn Ile Ala Arg Asp
                165                 170                 175
```

Ile Ile Asp Asp Ala Ala Ile Asp Arg Cys Tyr Leu Pro Ala Glu Trp
            180                 185                 190

Leu Gln Asp Ala Gly Leu Thr Pro Glu Asn Tyr Ala Ala Arg Glu Asn
        195                 200                 205

Arg Ala Ala Leu Ala Arg Val Ala Glu Arg Leu Ile Asp Ala Ala Glu
210                 215                 220

Pro Tyr Tyr Ile Ser Ser Gln Ala Gly Leu His Asp Leu Pro Pro Arg
225                 230                 235                 240

Cys Ala Trp Ala Ile Ala Thr Ala Arg Ser Val Tyr Arg Glu Ile Gly
                245                 250                 255

Ile Lys Val Lys Ala Ala Gly Gly Ser Ala Trp Asp Arg Arg Gln His
            260                 265                 270

Thr Ser Lys Gly Glu Lys Ile Ala Met Leu Met Ala Ala Pro Gly Gln
        275                 280                 285

Val Ile Arg Ala Lys Thr Thr Arg Val Thr Pro Arg Pro Ala Gly Leu
    290                 295                 300

Trp Gln Arg Pro Val
305

<210> SEQ ID NO 40
<211> LENGTH: 595
<212> TYPE: PRT
<213> ORGANISM: Cannabis sativa

<400> SEQUENCE: 40

Met Ala Thr Glu Leu Leu Cys Leu His Arg Pro Ile Ser Leu Thr His
1               5                   10                  15

Lys Leu Phe Arg Asn Pro Leu Pro Lys Val Ile Gln Ala Thr Pro Leu
            20                  25                  30

Thr Leu Lys Leu Arg Cys Ser Val Ser Thr Glu Asn Val Ser Phe Thr
        35                  40                  45

Glu Thr Glu Thr Glu Ala Arg Arg Ser Ala Asn Tyr Glu Pro Asn Ser
    50                  55                  60

Trp Asp Tyr Asp Tyr Leu Leu Ser Ser Asp Thr Asp Glu Ser Ile Glu
65                  70                  75                  80

Val Tyr Lys Asp Lys Ala Lys Lys Leu Glu Ala Glu Val Arg Arg Glu
                85                  90                  95

Ile Asn Asn Glu Lys Ala Glu Phe Leu Thr Leu Leu Glu Leu Ile Asp
            100                 105                 110

Asn Val Gln Arg Leu Gly Leu Gly Tyr Arg Phe Glu Ser Asp Ile Arg
        115                 120                 125

Gly Ala Leu Asp Arg Phe Val Ser Ser Gly Gly Phe Asp Ala Val Thr
    130                 135                 140

Lys Thr Ser Leu His Gly Thr Ala Leu Ser Phe Arg Leu Leu Arg Gln
145                 150                 155                 160

His Gly Phe Glu Val Ser Gln Glu Ala Phe Ser Gly Phe Lys Asp Gln
                165                 170                 175

Asn Gly Asn Phe Leu Glu Asn Leu Lys Glu Asp Ile Lys Ala Ile Leu
            180                 185                 190

Ser Leu Tyr Glu Ala Ser Phe Leu Ala Leu Glu Gly Glu Asn Ile Leu
        195                 200                 205

Asp Glu Ala Lys Val Phe Ala Ile Ser His Leu Lys Glu Leu Ser Glu
    210                 215                 220

Glu Lys Ile Gly Lys Glu Leu Ala Glu Gln Val Asn His Ala Leu Glu

-continued

```
            225                 230                 235                 240
Leu Pro Leu His Arg Arg Thr Gln Arg Leu Glu Ala Val Trp Ser Ile
                245                 250                 255

Glu Ala Tyr Arg Lys Lys Glu Asp Ala Asn Gln Val Leu Leu Glu Leu
            260                 265                 270

Ala Ile Leu Asp Tyr Asn Met Ile Gln Ser Val Tyr Gln Arg Asp Leu
        275                 280                 285

Arg Glu Thr Ser Arg Trp Trp Arg Arg Val Gly Leu Ala Thr Lys Leu
    290                 295                 300

His Phe Ala Arg Asp Arg Leu Ile Glu Ser Phe Tyr Trp Ala Val Gly
305                 310                 315                 320

Val Ala Phe Glu Pro Gln Tyr Ser Asp Cys Arg Asn Ser Val Ala Lys
                325                 330                 335

Met Phe Ser Phe Val Thr Ile Ile Asp Asp Ile Tyr Asp Val Tyr Gly
            340                 345                 350

Thr Leu Asp Glu Leu Glu Leu Phe Thr Asp Ala Val Glu Arg Trp Asp
        355                 360                 365

Val Asn Ala Ile Asn Asp Leu Pro Asp Tyr Met Lys Leu Cys Phe Leu
    370                 375                 380

Ala Leu Tyr Asn Thr Ile Asn Glu Ile Ala Tyr Asp Asn Leu Lys Asp
385                 390                 395                 400

Lys Gly Glu Asn Ile Leu Pro Tyr Leu Thr Lys Ala Trp Ala Asp Leu
                405                 410                 415

Cys Asn Ala Phe Leu Gln Glu Ala Lys Trp Leu Tyr Asn Lys Ser Thr
            420                 425                 430

Pro Thr Phe Asp Asp Tyr Phe Gly Asn Ala Trp Lys Ser Ser Ser Gly
        435                 440                 445

Pro Leu Gln Leu Val Phe Ala Tyr Phe Ala Val Val Gln Asn Ile Lys
    450                 455                 460

Lys Glu Glu Ile Glu Asn Leu Gln Lys Tyr His Asp Thr Ile Ser Arg
465                 470                 475                 480

Pro Ser His Ile Phe Arg Leu Cys Asn Asp Leu Ala Ser Ala Ser Ala
                485                 490                 495

Glu Ile Ala Arg Gly Glu Thr Ala Asn Ser Val Ser Cys Tyr Met Arg
            500                 505                 510

Thr Lys Gly Ile Ser Glu Leu Ala Thr Glu Ser Val Met Asn Leu
        515                 520                 525

Ile Asp Glu Thr Trp Lys Lys Met Asn Lys Lys Leu Gly Gly Ser
    530                 535                 540

Leu Phe Ala Lys Pro Phe Val Glu Thr Ala Ile Asn Leu Ala Arg Gln
545                 550                 555                 560

Ser His Cys Thr Tyr His Asn Gly Asp Ala His Thr Ser Pro Asp Glu
                565                 570                 575

Leu Thr Arg Lys Arg Val Leu Ser Val Ile Thr Glu Pro Ile Leu Pro
            580                 585                 590

Phe Glu Arg
        595
```

<210> SEQ ID NO 41
<211> LENGTH: 371
<212> TYPE: PRT
<213> ORGANISM: Campylobacter jejuni

<400> SEQUENCE: 41

```
Met Ser Glu Met Ser Leu Ile Met Leu Ala Gly Asn Ser Thr Arg
1               5                   10                  15

Phe Asn Thr Lys Val Lys Lys Gln Phe Leu Arg Leu Gly Asn Asp Pro
            20                  25                  30

Leu Trp Leu Tyr Ala Thr Lys Asn Leu Ser Ser Phe Tyr Pro Phe Lys
            35                  40                  45

Lys Ile Val Val Thr Ser Ser Asn Ile Thr Tyr Met Lys Lys Phe Thr
        50                  55                  60

Lys Asn Tyr Glu Phe Ile Glu Gly Gly Asp Thr Arg Ala Glu Ser Leu
65                  70                  75                  80

Lys Lys Ala Leu Glu Leu Ile Asp Ser Glu Phe Val Met Val Ser Asp
                85                  90                  95

Val Ala Arg Val Leu Val Ser Lys Asn Leu Phe Asp Arg Leu Ile Glu
                100                 105                 110

Asn Leu Asp Lys Ala Asp Cys Ile Thr Pro Ala Leu Lys Val Ala Asp
            115                 120                 125

Thr Thr Leu Phe Asp Asn Glu Ala Leu Gln Arg Glu Lys Ile Lys Leu
        130                 135                 140

Ile Gln Thr Pro Gln Ile Ser Lys Thr Lys Leu Leu Lys Lys Ala Leu
145                 150                 155                 160

Asp Gln Asn Leu Glu Phe Thr Asp Asp Ser Thr Ala Ile Ala Ala Met
                165                 170                 175

Gly Gly Lys Ile Trp Phe Val Glu Gly Glu Asn Ala Arg Lys Leu
                180                 185                 190

Thr Phe Lys Glu Asp Leu Lys Lys Leu Asp Leu Pro Thr Pro Ser Phe
        195                 200                 205

Glu Ile Phe Thr Gly Asn Gly Phe Asp Val His Glu Phe Gly Glu Asn
        210                 215                 220

Arg Pro Leu Leu Leu Ala Gly Val Gln Ile His Pro Thr Met Gly Leu
225                 230                 235                 240

Lys Ala His Ser Asp Gly Asp Val Leu Ala His Ser Leu Thr Asp Ala
                245                 250                 255

Ile Leu Gly Ala Ala Gly Leu Gly Asp Ile Gly Glu Leu Tyr Pro Asp
                260                 265                 270

Thr Asp Met Lys Phe Lys Asn Ala Asn Ser Met Glu Leu Leu Lys Gln
        275                 280                 285

Ala Tyr Asp Lys Val Arg Glu Ile Gly Phe Glu Leu Ile Asn Ile Asp
        290                 295                 300

Ile Cys Val Met Ala Gln Ser Pro Lys Leu Lys Asp Phe Lys Gln Ala
305                 310                 315                 320

Met Gln Ser Asn Ile Ala His Thr Leu Asp Leu Asp Glu Phe Arg Ile
                325                 330                 335

Asn Val Lys Ala Thr Thr Thr Glu Lys Leu Gly Phe Ile Gly Arg Lys
                340                 345                 350

Glu Gly Met Ala Val Leu Ser Ser Val Asn Leu Lys Tyr Phe Asp Trp
            355                 360                 365

Thr Arg Leu
    370

<210> SEQ ID NO 42
<211> LENGTH: 395
<212> TYPE: PRT
<213> ORGANISM: Escherichia coli

<400> SEQUENCE: 42
```

```
Met Ala Thr Thr His Leu Asp Val Cys Ala Val Pro Ala Ala Gly
1               5                   10                  15

Phe Gly Arg Arg Met Gln Thr Glu Cys Pro Lys Gln Tyr Leu Ser Ile
            20                  25                  30

Gly Asn Gln Thr Ile Leu Glu His Ser Val His Ala Leu Leu Ala His
        35                  40                  45

Pro Arg Val Lys Arg Val Val Ile Ala Ile Ser Pro Gly Asp Ser Arg
50                  55                  60

Phe Ala Gln Leu Pro Leu Ala Asn His Pro Gln Ile Thr Val Val Asp
65                  70                  75                  80

Gly Gly Asp Glu Arg Ala Asp Ser Val Leu Ala Gly Leu Lys Ala Ala
                85                  90                  95

Gly Asp Ala Gln Trp Val Leu Val His Asp Ala Ala Arg Pro Cys Leu
                100                 105                 110

His Gln Asp Asp Leu Ala Arg Leu Leu Ala Leu Ser Glu Thr Ser Arg
            115                 120                 125

Thr Gly Gly Ile Leu Ala Ala Pro Val Arg Asp Thr Met Lys Arg Ala
130                 135                 140

Glu Pro Gly Lys Asn Ala Ile Ala His Thr Val Asp Arg Asn Gly Leu
145                 150                 155                 160

Trp His Ala Leu Thr Pro Gln Phe Phe Pro Arg Glu Leu Leu His Asp
                165                 170                 175

Cys Leu Thr Arg Ala Leu Asn Glu Gly Ala Thr Ile Thr Asp Glu Ala
            180                 185                 190

Ser Ala Leu Glu Tyr Cys Gly Phe His Pro Gln Leu Val Glu Gly Arg
            195                 200                 205

Ala Asp Asn Ile Lys Val Thr Arg Pro Glu Asp Leu Ala Leu Ala Glu
210                 215                 220

Phe Tyr Leu Thr Arg Thr Ile His Gln Glu Asn Thr Met Arg Ile Gly
225                 230                 235                 240

His Gly Phe Asp Val His Ala Phe Gly Gly Glu Gly Pro Ile Ile Ile
                245                 250                 255

Gly Gly Val Arg Ile Pro Tyr Glu Lys Gly Leu Leu Ala His Ser Asp
                260                 265                 270

Gly Asp Val Ala Leu His Ala Leu Thr Asp Ala Leu Leu Gly Ala Ala
            275                 280                 285

Ala Leu Gly Asp Ile Gly Lys Leu Phe Pro Asp Thr Asp Pro Ala Phe
290                 295                 300

Lys Gly Ala Asp Ser Arg Glu Leu Leu Arg Glu Ala Trp Arg Arg Ile
305                 310                 315                 320

Gln Ala Lys Gly Tyr Thr Leu Gly Asn Val Asp Val Thr Ile Ile Ala
            325                 330                 335

Gln Ala Pro Lys Met Leu Pro His Ile Pro Gln Met Arg Val Phe Ile
            340                 345                 350

Ala Glu Asp Leu Gly Cys His Met Asp Asp Val Asn Val Lys Ala Thr
            355                 360                 365

Thr Thr Glu Lys Leu Gly Phe Thr Gly Arg Gly Glu Gly Ile Ala Cys
370                 375                 380

Glu Ala Val Ala Leu Leu Ile Lys Ala Thr Lys
385                 390                 395

<210> SEQ ID NO 43
<211> LENGTH: 6
```

```
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 43

His His His His His His
1               5
```